(12) United States Patent
Klingemann et al.

(10) Patent No.: US 11,753,625 B2
(45) Date of Patent: *Sep. 12, 2023

(54) MODIFIED NK-92 HANK003 CELLS FOR THE CLINIC

(71) Applicant: NantKwest, Inc., San Diego, CA (US)

(72) Inventors: Hans Klingemann, Boston, MA (US); Laurent Boissel, Boston, MA (US); Patrick Soon-Shiong, Los Angeles, CA (US)

(73) Assignee: ImmunityBio, Inc., San Diego, CA (US)

( * ) Notice: Subject to any disclaimer, the term of this patent is extended or adjusted under 35 U.S.C. 154(b) by 521 days.

This patent is subject to a terminal disclaimer.

(21) Appl. No.: 16/937,370

(22) Filed: Jul. 23, 2020

(65) Prior Publication Data

US 2020/0347351 A1 Nov. 5, 2020

Related U.S. Application Data

(60) Continuation of application No. 16/424,201, filed on May 28, 2019, now Pat. No. 10,774,310, which is a division of application No. 15/914,665, filed on Mar. 7, 2018, now Pat. No. 10,801,013.

(60) Provisional application No. 62/468,890, filed on Mar. 8, 2017.

(51) Int. Cl.
*A61K 35/17* (2015.01)
*C12N 5/0783* (2010.01)
*C07K 14/55* (2006.01)
*C07K 14/735* (2006.01)
*C12N 15/85* (2006.01)
*A61K 48/00* (2006.01)

(52) U.S. Cl.
CPC ............ *C12N 5/0646* (2013.01); *A61K 48/00* (2013.01); *C07K 14/55* (2013.01); *C07K 14/70535* (2013.01); *C12N 15/85* (2013.01); *C12N 2510/00* (2013.01)

(58) Field of Classification Search
None
See application file for complete search history.

(56) References Cited

U.S. PATENT DOCUMENTS

| | | |
|---|---|---|
| 7,618,817 B2 | 11/2009 | Campbell |
| 8,034,332 B2 | 10/2011 | Klingemann |
| 8,313,943 B2 | 11/2012 | Campbell |
| 10,138,462 B2 | 11/2018 | Kilingemann |
| 10,456,420 B2 | 10/2019 | Lee |
| 2002/0068044 A1 | 6/2002 | Klingemann |
| 2004/0052770 A1 | 3/2004 | Klingemann |
| 2006/0292156 A1 | 12/2006 | Campbell |
| 2018/0193383 A1 | 7/2018 | Lee |

FOREIGN PATENT DOCUMENTS

| | | |
|---|---|---|
| CA | 2 289 915 A1 | 4/1998 |
| EP | 2 161 339 A1 | 3/2010 |
| WO | 98/49268 A1 | 11/1998 |
| WO | 2016/160602 A2 | 10/2016 |
| WO | 2016/201304 A1 | 12/2016 |

OTHER PUBLICATIONS

Rezvani and Rouce (Frontiers in Immunology vol. 6, article 578. Doi:10.3398/fimmu.2015.00578, pp. 1-13, 2015) (Year: 2015).*
European Application No. 18763512.3, Extended European Search Report, dated Dec. 1, 2020, 8 pages.
Carlsten, et al., "Genetic Manipulation of NK Cells for Cancer Immunotherapy: Techniques and Clinical Implications," Frontiers in Immunology, vol. 6, Jun. 2015, 9 pages.
Maki, et al., "Factors Regulating the Cytotoxic Activity of the Human Natural Killer Cell Line, NK-92," Journal of Hematotherapy and Stem Cell Research, vol. 10, No. 3, Jun. 2001, pp. 369-383.
Australian Patent Application No. 2021236511, First Examination Report, dated Oct. 29, 2021, 4 pages.
Australian Patent Application No. 2021236511, Second Examination Report, dated Nov. 11, 2021, 2 pages.
Australian PaentApplication No. 2021236511, Acceptance Fee Official Receipt, dated Dec. 12, 2021, 1 page.
Faibish et al., "A YKL-40 neutralizing antibody blocks tumor angiogenesis and progression: a potential therapeutic agent in cancers," Mol Cancer Ther., May 2011, 10(5): 742-751.
Gong et al., "Characterization of a Human Cell Line (NK-92) with Phenotypical and Functional Characteristics of Activated Natural Killer Cells," Leukemia, Apr. 1994, vol. 8., No. 4, pp. 652-658.
International Application No. PCT/US2018/021332, International Search Report dated Jun. 8, 2018, 5 pages.
Jing et al., "Identification of an ADAM17 Cleavage Region in Human CD16 (FcγRIII) and the Engineering of a Non-Cleavable Version of the Receptor in NK Cells," Mar. 27, 2015, PLOS One | DOI:10.1371/journal.pone.0121788.
Jochems et al., "An NK cell line (haNK) expressing high levels of granzyme and engineered to express the high affinity CD16 allele," Oncotarget, 2016, vol. 7, (No. 52), 86359-86373.
Klingemann et al., "Natural Killer Cells for Immunotherapy—Advantages of the NK-92 Cell Line over Blood NK Cells," Frontiers in Immunology, Mar. 2016, vol. 7, Article 91, 7 pages.
Tsang et al., Journal for ImmunoTherapy of Cancer (2016) vol. 4, Supp. Supplement 1, Abstract No. P20, Meeting Info: 31$^{st}$ Annual Meeting and Associated Programs of the Society for Immunotherapy of Cancer, SITC 2016, National Harbor, MD, United States, Nov. 9, 2016-Nov. 13, 2016.

(Continued)

*Primary Examiner* — Marcia S Noble
(74) *Attorney, Agent, or Firm* — Kilpatrick, Townsend & Stockton, LLP

(57) ABSTRACT

Provided herein are populations of modified NK-92 cells, compositions and kits comprising the cells, and methods of making and using the populations of cells.

18 Claims, 26 Drawing Sheets

Specification includes a Sequence Listing.

(56) References Cited

OTHER PUBLICATIONS

Boissel et al., Cancer Researh (2016) vol. 76, No. 14, Supp. Supplement, Abstract No. 2302, Meeting Info: 107$^{th}$ Annual Meeting of the American Association for Cancer Research, AACR 2016. New Orleans, LA, United States, Apr. 16, 2016-Apr. 20, 2016.
PCT/US2018/021332 , "International Preliminary Report on Patentability", dated Sep. 19, 2019, 8 pages.
Canadian Application No. 3,053,252, First Examiner'sReport, dated Apr. 7, 2021, 3 pages.
Australian Patent Application No. 2018231193, First Examination Report, dated May 25, 2021, 4 pages.
Korean Patent Application No. 10-2019-7028804, "Notice of Preliminary Rejection," dated Sep, 7, 2022, 7 pages.
Notice of Reasonsfor Rejection, Japanese Patent Application No. 2019-548664, dated Jan. 17, 2022, 7 pages.
Israel Patent Application No. 268617, Office Action dated Oct. 30, 2022, 7 pages.
Chinese Patent Application No. 201880016940.6, Office Action, dated Aug. 22, 2022, 19 pages.

* cited by examiner

SEQUENCE LISTING

```
<160> NUMBER OF SEQ ID NOS: 6

<210> SEQ ID NO 1
<211> LENGTH: 5491
<212> TYPE: DNA
<213> ORGANISM: artificial sequence
<220> FEATURE:
<223> OTHER INFORMATION: synthetic construct

<400> SEQUENCE: 1
tgtatttaga aaaataaaca aatagggtt ccgcgcacat tccccgaaa agtgccacct        60 gacgtcgacg gatcgggaga tctcccgatc ccctatggtg cactctcagt acaatctgct    120
ctgatgccgc atagttaagc cagtatctgc tccctgcttg tgtgttggag gtcgctgagt    180
agtgcgcgag caaaatttaa gctacaacaa ggcaaggctt gaccgacaat tgcatgaaga    240
atctgcttag ggttaggcgt tttgcgctgc ttcgggatcc gctgaccaaa agagcaccaa    300
aggcgccctg accttcagcc cctacctgcg ctccggtgcc cgtcagtggg cagagcgcac    360
atcgcccaca gtccccgaga agttgggggg aggggtcggc aattgaaccg gtgcctagag    420
aaggtggcgc ggggtaaact gggaaagtga tgtcgtgtac tggctccgcc tttttcccga    480
gggtggggga gaaccgtata taagtgcagt agtcgccgtg aacgttcttt tcgcaacgg    540 gtttgccgcc agaacacagg taagtgccgt gtgtggttcc cgcgggcctg gcctctttac    600
gggttatggc ccttgcgtgc cttgaattac ttccacctgg ctgcagtacg tgattcttga    660
tcccgagctt cggggttggaa gtgggtggga gagttcgagg ccttgcgctt aaggagcccc    720
ttcgcctcgt gcttgagttg aggcctggcc tgggcgctgg ggccgccgcg tgcgaatctg    780
gtggcacctt cgcgcctgtc tcgctgcttt cgataagtct ctagccattt aaaattttg    840 atgacctgct gcgacgcttt ttttctggca agatagtctt gtaaatgcgg gccaagatct    900
gcacactggt atttcggttt ttggggccgc gggcggcgac ggggcccgtg cgtcccagcg    960
cacatgttcg gcgaggcggg gcctgcgagc gcggccaccg agaatcggac gggggtagtc   1020
tcaagctggc cggcctgctc tggtgcctgg cctcgcgccg ccgtgtatcg ccccgccctg   1080
```

```
ggcggcaagg ctggcccggt cggcaccagt tgcgtgagcg aaagatggc cgcttcccgg    1140 ccctgctgca gggagctcaa aatggaggac gcggcgctcg ggagagcggg cgggtgagtc    1200
acccacacaa aggaaaaggg cctttccgtc ctcagccgtc gcttcatgtg actccacgga    1260
gtaccgggcg ccgtccaggc acctcgatta gttctcgagc ttttggagta cgtcgtcttt    1320
aggttggggg gaggggtttt atgcgatgga gtttccccac actgagtggg tggagactga    1380
agttaggcca gcttggcact tgatgtaatt ctccttggaa tttgcccttt ttgagtttgg    1440
atcttggttc attctcaagc ctcagacagt ggttcaaagt ttttttcttc catttcaggt    1500
gtcgtgataa tacgactcac tatagggaga cccaagctgg aattcgccac catgtggcag    1560
ctgctgctgc ctacagctct cctgctgctg gtgtccgccg gcatgagaac cgaggatctg    1620
cctaaggccg tggtgttcct ggaaccccag tggtacagag tgctggaaaa ggacagcgtg    1680
accctgaagt gccagggcgc ctacagcccc gaggacaata gcacccagtg gttccacaac    1740
gagagcctga tcagcagcca ggccagcagc tacttcatcg acgccgccac cgtggacgac    1800
agcggcgagt atagatgcca gaccaacctg agcacccctga gcgaccccgt gcagctggaa    1860
gtgcacatcg gatggctgct gctgcaggcc cccagatggg tgttcaaaga agaggaccccc    1920 atccacctga gatgccactc ttggaagaac accgccctgc acaaagtgac ctacctgcag    1980
aacggcaagg gcagaaagta cttccaccac aacagcgact tctacatccc caaggccacc    2040
ctgaaggact ccggctccta cttctgcaga ggcctcgtgg gcagcaagaa cgtgtccagc    2100
gagacagtga acatcaccat cacccagggc ctggccgtgt ctaccatcag cagcttttc    2160 ccacccggct accaggtgtc cttctgcctc gtgatggtgc tgctgttcgc cgtggacacc    2220
ggcctgtact tcagcgtgaa aacaaacatc agaagcagca cccgggactg gaaggaccac    2280
aagttcaagt ggcggaagga cccccaggac aagtgaaatt ccgcccctct cccccccccc    2340
cctctccctc ccccccccct aacgttactg gccgaagccg cttggaataa ggccggtgtg    2400
cgtttgtcta tatgttattt tccaccatat tgccgtcttt tggcaatgtg agggcccgga    2460
aacctggccc tgtcttcttg acgagcattc ctaggggtct ttcccctctc gccaaaggaa    2520
tgcaaggtct gttgaatgtc gtgaaggaag cagttcctct ggaagcttct tgaagacaaa    2580
caacgtctgt agcgaccctt gcaggcagc ggaaccccccc acctggcgac aggtgcctct    2640
gcggccaaaa gccacgtgta taagatacac ctgcaaaggc ggcacaaccc cagtgccacg    2700
ttgtgagttg gatagttgtg gaaagagtca aatggctctc ctcaagcgta ttcaacaagg    2760
ggctgaagga tgcccagaag gtaccccatt gtatgggatc tgatctgggg cctcggtgca    2820
catgctttac atgtgtttag tcgaggttaa aaaacgtct aggcccccg aaccacgggg    2880 acgtggtttt cctttgaaaa acacgataac cgccaccatg taccggatgc agctgctgag    2940
ctgtatcgcc ctgtctctgg ccctcgtgac caacagcgcc cctaccagca gcagcaccaa    3000
gaaaacccag ctgcagctgg aacatctgct gctggacctg cagatgatcc tgaacggcat    3060
caacaactac aagaaccccca gctgacccg gatgctgacc ttcaagttct acatgcccaa    3120
gaaggccacc gaactgaaac atctgcagtg cctggaagag gaactgaagc ccctggaaga    3180
agtgctgaac ctgcccccaga gcaagaactt ccacctgagg cccagggacc tgatcagcaa    3240
catcaacgtg atcgtgctgg aactgaaagg cagcgagaca accttcatgt gcgagtacgc    3300
cgacgagaca gctaccatcg tggaatttct gaaccgggtgg atcaccttct gccagagcat    3360
catcagcacc ctgaccggct ccgagaagga cgagctgtga gcggccgccc gctgatcagc    3420
```

```
ctcgaacgag atttcgattc caccgccgcc ttctatgaaa ggttgggctt cggaatcgtt      3480
ttccgggacg ccggctggat gatcctccag cgcggggatc tcatgctgga gttcttcgcc      3540
caccccaact tgtttattgc agcttataat ggttacaaat aaagcaatag catcacaaat      3600
ttcacaaata aagcattttt ttcactgcat tctagttgtg gtttgtccaa actcatcaat      3660
gtatcttatc atgtctgtgc ggtgggctct atggcttctg aggcggaaag aaccagctgg      3720
ggctctaggg ggtatcccog gatcctgagc aaaaggccag caaaaggcca ggaaccgtaa      3780
aaaggccgcg ttgctggcgt ttttccatag gctccgcccc cctgacgagc atcacaaaaa      3840
tcgacgctca agtcagaggt ggcgaaaccc gacaggacta aagatacc aggcgtttcc      3900 ccctggaagc tccctcgtgc gctctcctgt tccgaccctg ccgcttaccg gatacctgtc      3960
cgcctttctc ccttcgggaa gcgtggcgct ttctcatagc tcacgctgta ggtatctcag      4020
ttcggtgtag gtcgttcgct ccaagctggg ctgtgtgcac gaaccccccg ttcagcccga      4080
ccgctgcgcc ttatccggta actatcgtct tgagtccaac ccggtaagac acgacttatc      4140
gccactggca gcagccactg gtaacaggat tagcagagcg aggtatgtag gcggtgctac      4200
agagttcttg aagtggtggc ctaactacgg ctacactaga agaacagtat ttggtatctg      4260
cgctctgctg aagccagtta ccttcggaaa aagagttggt agctcttgat ccggcaaaca      4320
aaccaccgct ggtagcggtg gttttttttgt ttgcaagcag cagattacgc gcagaaaaaa      4380
aggatctcaa gaagatcctt tgatcttttc tacggggtct gacgctcagt ggaacgaaaa      4440
ctcacgttaa gggattttgg tcatgagatt atcaaaaagg atcttcacct agatcctttt      4500
aaattaaaaa tgaagtttta aatcaatcta agtatatat gagtaaactt ggtctgacag      4560
ttaccaatgc ttaatcagtg aggcacctat ctcagcgatc tgtctatttc gttcatccat      4620
agttgcctga ctccccgtcg tgtagataac tacgatacgg gagggcttac catctggccc      4680
cagtgctgca atgataccgc gagaaccacg ctcaccggct ccagatttat cagcaataaa      4740
ccagccagcc ggaagggccg agcgcagaag tggtcctgca actttatccg cctccatcca      4800
gtctattaat tgttgccggg aagctagagt aagtagttcg ccagttaata gtttgcgcaa      4860
cgttgttgcc attgctacag gcatcgtggt gtcacgctcg tcgtttggta tggcttcatt      4920
cagctccggt tcccaacgat caaggcgagt tacatgatcc cccatgttgt gcaaaaaagc      4980
ggttagctcc ttcggtcctc cgatcgttgt cagaagtaag ttggccgcag tgttatcact      5040
catggttatg gcagcactgc ataattctct tactgtcatg ccatccgtaa gatgcttttc      5100
tgtgactggt gagtactcaa ccaagtcatt ctgagaatag tgtatgcggc gaccgagttg      5160
ctcttgcccg gcgtcaatac gggataatac cgcgccacat agcagaactt taaaagtgct      5220
catcattgga aaacgttctt cggggcgaaa actctcaagg atcttaccgc tgttgagatc      5280
cagttcgatg taacccactc gtgcacccaa ctgatcttca gcatctttta ctttcaccag      5340
cgtttctggg tgagcaaaaa caggaaggca aaatgccgca aaaaagggaa taagggcgac      5400
acggaaatgt tgaatactca tactcttcct ttttcaatat tattgaagca tttatcaggg      5460
ttattgtctc atgagcggat acatatttga a                                     5491
```

<210> SEQ ID NO 2
<211> LENGTH: 1872
<212> TYPE: DNA
<213> ORGANISM: artificial sequence
<220> FEATURE:
<223> OTHER INFORMATION: synthetic construct

<400> SEQUENCE: 2

```
gaattcgcca ccatgtggca gctgctgctg cctacagctc tcctgctgct ggtgtccgcc    60
ggcatgagaa ccgaggatct gcctaaggcc gtggtgttcc tggaacccca gtggtacaga   120
gtgctggaaa aggacagcgt gaccctgaag tgccagggcg cctacagccc cgaggacaat   180
agcacccagt ggttccacaa cgagagcctg atcagcagcc aggccagcag ctacttcatc   240
gacgccgcca ccgtggacga cagcggcgag tatagatgcc agaccaacct gagcaccctg   300
agcgaccccg tgcagctgga agtgcacatc ggatggctgc tgctgcaggc ccccagatgg   360
gtgttcaaag aagaggaccc catccacctg agatgccact cttggaagaa caccgccctg   420
cacaaagtga cctacctgca gaacggcaag gcagaaagt acttccacca acagcgac     480 ttctacatcc ccaaggccac cctgaaggac tccggctcct acttctgcag aggcctcgtg   540
ggcagcaaga acgtgtccag cgagacagtg aacatcacca tcacccaggg cctggccgtg   600
tctaccatca gcagctttt cccacccggc taccaggtgt ccttctgcct cgtgatggtg   660
ctgctgttcg ccgtggacac cggcctgtac ttcagcgtga aaacaaacat cagaagcagc   720
acccgggact ggaaggacca caagttcaag tggcggaagg accccaggga caagtgaaat   780 tccgccccte tccccccccc ccctctccct cccccccccc taacgttact ggccgaagcc   840
gcttggaata aggccggtgt gcgtttgtct atatgttatt ttccaccata ttgccgtctt   900
ttggcaatgt gagggcccgg aaacctggcc ctgtcttctt gacgagcatt cctaggggtc   960
tttcccctct cgccaaagga atgcaaggtc tgttgaatgt cgtgaaggaa gcagttcctc  1020
tggaagcttc ttgaagacaa acaacgtctg tagcgaccct ttgcaggcag cggaaccccc  1080
cacctggcga caggtgcctc tgcggccaaa agccacgtgt ataagataca cctgcaaagg  1140
cggcacaacc ccagtgccac gttgtgagtt ggatagttgt ggaaagagtc aaatggctct  1200
cctcaagcgt attcaacaag ggctgaagg atgcccagaa ggtaccccat tgtatgggat  1260
ctgatctggg gcctcggtgc acatgcttta catgtgttta gtcgaggtta aaaaaacgtc  1320 taggccccc gaaccacggg gacgtggttt tcctttgaaa aacacgataa ccgccaccat  1380
gtaccggatg cagctgctga gctgtatcgc cctgtctctg gccctcgtga ccaacagcgc  1440
ccctaccagc agcagcacca gaaaaaccca gctgcagctg gaacatctgc tgctggacct  1500
gcagatgatc ctgaacggca tcaacaacta caagaacccc aagctgaccc ggatgctgac  1560
cttcaagttc tacatgccca gaaggccac cgaactgaaa catctgcagt gcctggaaga  1620
ggaactgaag cccctggaag aagtgctgaa cctggcccag agcaagaact tccacctgag  1680
gcccagggac ctgatcagca acatcaacgt gatcgtgctg gaactgaaag cagcgagac  1740 aaccttcatg tgcgagtacg ccgacgagac agctaccatc gtggaatttc tgaaccggtg  1800
gatcaccttc tgccagagca tcatcagcac cctgaccggc tccgagaagg acgagctgtg  1860
agcggccgcc cg                                                       1872
```

<210> SEQ ID NO 3
<211> LENGTH: 765
<212> TYPE: DNA
<213> ORGANISM: artificial sequence
<220> FEATURE:
<223> OTHER INFORMATION: synthetic construct

<400> SEQUENCE: 3

```
atgtggcagc tgctgctgcc tacagctctc tgctgctgg tgtccgccgg catgagaacc    60
gaggatctgc ctaaggccgt ggtgttcctg aaccccagt ggtacagagt gctggaaaag   120
```

```
gacagcgtga ccctgaagtg ccagggcgcc tacagccccg aggacaatag cacccagtgg      180
ttccacaacg agagcctgat cagcagccag gccagcagct acttcatcga cgccgccacc      240
gtggacgaca gcggcgagta tagatgccag accaacctga gcaccctgag cgaccccgtg      300
cagctggaag tgcacatcgg atggctgctg ctgcaggccc ccagatgggt gttcaaagaa      360
gaggacccca tccacctgag atgccactct tggaagaaca ccgccctgca caaagtgacc      420
tacctgcaga acggcaaggg cagaaagtac ttccaccaca acagcgactt ctacatcccc      480
aaggccaccc tgaaggactc cggctcctac ttctgcagag gcctcgtggg cagcaagaac      540
gtgtccagcg agacagtgaa catcaccatc acccagggcc tggccgtgtc taccatcagc      600 agcttttttcc cacccggcta ccaggtgtcc ttctgcctcg tgatggtgct gctgttcgcc      660
gtggacaccg gcctgtactt cagcgtgaaa acaaacatca gaagcagcac ccgggactgg      720
aaggaccaca gttcaagtg gcggaaggac ccccaggaca gtga                        765
```

<210> SEQ ID NO 4
<211> LENGTH: 254
<212> TYPE: PRT
<213> ORGANISM: artificial sequence
<220> FEATURE:
<223> OTHER INFORMATION: synthetic construct

<400> SEQUENCE: 4

```
Met Trp Gln Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250
```

<210> SEQ ID NO 5
<211> LENGTH: 483
<212> TYPE: DNA
<213> ORGANISM: artificial sequence
<220> FEATURE:
<223> OTHER INFORMATION: synthetic construct

<400> SEQUENCE: 5

```
atgtaccgga tgcagctgct gagctgtatc gccctgtctc tggccctcgt gaccaacagc      60
gcccctacca gcagcagcac caagaaaacc cagctgcagc tggaacatct gctgctggac     120
ctgcagatga tcctgaacgg catcaacaac tacaagaacc ccaagctgac ccggatgctg     180
accttcaagt tctacatgcc caagaaggcc accgaactga acatctgca gtgcctggaa      240
gaggaactga agcccctgga agaagtgctg aacctggccc agagcaagaa cttccacctg     300
aggcccaggg acctgatcag caacatcaac gtgatcgtgc tggaactgaa aggcagcgag     360
acaaccttca gtgcgagta cgccgacgag acagctacca tcgtggaatt tctgaaccgg     420
tggatcacct tctgccagag catcatcagc accctgaccg gctccgagaa ggacgagctg     480
tga                                                                    483
```

<210> SEQ ID NO 6
<211> LENGTH: 160
<212> TYPE: PRT
<213> ORGANISM: artificial sequence
<220> FEATURE:
<223> OTHER INFORMATION: synthetic construct

<400> SEQUENCE: 6

```
Met Tyr Arg Met Gln Leu Leu Ser Cys Ile Ala Leu Ser Leu Ala Leu
  1               5                  10                  15

Val Thr Asn Ser Ala Pro Thr Ser Ser Ser Thr Lys Lys Thr Gln Leu
             20                  25                  30

Gln Leu Glu His Leu Leu Leu Asp Leu Gln Met Ile Leu Asn Gly Ile
         35                  40                  45

Asn Asn Tyr Lys Asn Pro Lys Leu Thr Arg Met Leu Thr Phe Lys Phe
     50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr Gly Ser Glu Lys Asp Glu Leu
145                 150                 155                 160
```

MODIFIED NK-92 HANK003 CELLS FOR THE CLINIC

CROSS-REFERENCE TO RELATED APPLICATIONS

The present application is a continuation of U.S. application Ser. No. 16/424,201, filed May 28, 2019, which is a divisional of U.S. application Ser. No. 15/914,665, filed Mar. 7, 2018, which claims priority to U.S. Provisional Application No. 62/468,890, filed Mar. 8, 2017, the contents of which are herein incorporated by reference in their entirety for all purposes

BACKGROUND

Anticancer treatment with monoclonal antibodies (mAbs) has significantly improved the clinical outcome in patients with cancer. One of the major mechanisms of action of therapeutic antibodies is through antibody dependent cellular cytotoxicity (ADCC). Natural killer cells could be used as cytotoxic effector cells for cell-based immunotherapy since they are a major effector cell for ADCC.

NK-92 is a cytolytic cancer cell line which was discovered in the blood of a subject suffering from a non-Hodgkin's lymphoma and then immortalized ex vivo. NK-92 cells are derived from NK cells, but lack the major inhibitory receptors that are displayed by normal NK cells, while retaining the majority of the activating receptors. NK-92 cells do not, however, attack normal cells nor do they elicit an unacceptable immune rejection response in humans. Characterization of the NK-92 cell line is disclosed in WO 1998/49268 and U.S. Patent Application Publication No. 2002-0068044. NK-92 cells have also been evaluated as a potential therapeutic agent in the treatment of certain cancers.

Although NK-92 cells retain almost all of the activating receptors and cytolytic pathways associated with NK cells, they do not express CD16 on their cell surfaces. CD16 is an Fc receptor which recognizes and binds to the Fc portion of an antibody to activate NK cells for the ADCC effector mechanism. Because they lack CD16 receptors, unmodified NK-92 cells are unable to lyse target cells via the ADCC mechanism.

BRIEF SUMMARY

Provided herein are populations of modified NK-92 cells, compositions and kits comprising the cells, and methods of making and using the populations of cells.

BRIEF DESCRIPTION OF THE DRAWINGS

FIG. 27A shows flow cytometric analysis of CD16 expression level in haNK-003 after ADCC along with control (E:T=1:0). FIG. 27B shows median fluorescence intensity (MFI) of CD16 expression after ADCC and 24 hours after ADCC.

DETAILED DESCRIPTION

Figure 1A:
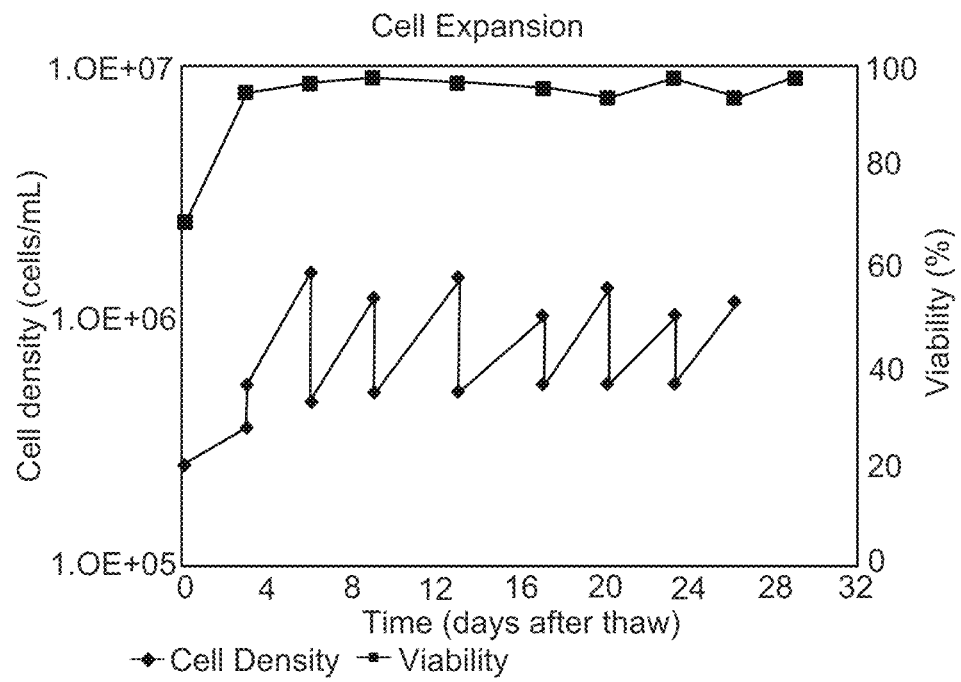
FIG. 1A is a graph showing haNK003 cell expansion.

Provided herein are modified NK-92 haNK003 cells. The cells express the Fc Receptor CD16 and an endoplasmic reticulum bound form of IL-2. Thus, the cells are not dependent on external IL-2 for growth. Further, the modified NK-92 cells have enhanced cytotoxic capabilities with the insertion of the high affinity variant of the CD16 receptor, and are therefore capable of CD16 targeted antibody-dependent cell-mediated cytotoxicity (ADCC). ADCC is mediated by recognition of the Fc fragment of the target-bound antibody (IgG) via the CD16 Fc receptor. Therefore, for oncological applications, ADCC by the modified cells is elicited by CD16 receptor binding to the Fc fragment of tumor cell-bound IgG, thus activating the modified NK-92 cells for targeted killing. As described herein, the provided modified NK-92 cells were created through stable transfection with a bicistronic plasmid based vector containing sequences for CD16, the high affinity Fc-gamma receptor (FcγRIIIa/CD16a), as well as IL-2 that is targeted to the endoplasmic reticulum. The cells contain a plasmid sequence that was inserted at a single location on Chromosome 17 at position 15,654,977 on the + strand. The modified NK-92 cells produce endogenous IL-2 and are phenotypically CD56+, CD3−, and CD16+. The modified NK-92 haNK003 cells provided in the present application are sometimes referred to herein as simply haNK003 cells.

As described in more detail in the examples below, NK-92 cells were transformed with the pNEUKv1_FcRIL2 plasmid (SEQ ID NO:1). The pNEUKv1_FcRIL2 plasmid is a bicistronic construct expressing a modified CD16 that contains a valine at amino acid 176 (when referring to the full length CD16 peptide) and IL-2 with an endoplasmic reticulum retention signal. Whole genome sequencing (WGS) of the cells were performed, resulting in identification of one plasmid insertion site at Chromosome 17. WGS confirmed that the integration of the bicistronic plasmid in the haNK003 cell line is in a region of the genome that is distant from any gene with oncogenic potential. The nearest 5' gene TBC1D26 is 10,722 bp upstream, and the nearest 3' gene ADORA2B is 186,828 bp downstream. The modified NK-92 cells grow consistently when passaged every 3 to 4 days and seeded at a density of approximately $0.3-0.5\times10^6$ cells/mL. The mean doubling time was 65 (48-95) hours from day 3 to day 29. Analysis of flow cytometry data shows that modified NK-92 cells express CD54, CD56, NKG2D, NKp30, and CD16 surface marker proteins and lack CD3. The modified NK-92 cells are capable of growing without supplementation of IL-2 in the culture media. Further, it was determined that the modified NK-92 cells expressing IL-2 release low levels of IL-2 into culture media. Non-irradiated haNK003 cells alone secrete on average approximately 276.1 pg/mL per 1,000,000 cells at 6 hours and up to 1403.3 pg/mL per 1,000,000 cells at 48 hours in culture. The provided modified NK-92 cells are naturally cytotoxic to several cancer cell lines and are capable of enhanced specific lysis via ADCC when combined with antibodies.

The NK-92 cell line was discovered to proliferate in the presence of interleukin 2 (IL-2). Gong et al., *Leukemia* 8:652-658 (1994). These cells have high cytolytic activity against a variety of cancers. The NK-92 cell line is a homogeneous NK cell population having broad anti-tumor cytotoxicity with predictable yield after expansion. Phase I clinical trials have confirmed its safety profile. NK-92 was discovered in the blood of a subject suffering from a non-Hodgkin's lymphoma and then immortalized ex vivo. NK-92 cells are derived from NK cells, but lack the major inhibitory receptors that are displayed by normal NK cells, while retaining the majority of the activating receptors. NK-92 cells do not, however, attack normal cells nor do they elicit an unacceptable immune rejection response in humans. Characterization of the NK-92 cell line is disclosed in WO 1998/49268 and U.S. Patent Application Publication No. 2002-0068044.

NK-92 cells are known and include, but are not limited to, those described in, e.g., U.S. Pat. Nos. 7,618,817, 8,034,332, and 8,313,943, US Patent Application Publication No. 2013/0040386, all of which are incorporated herein by reference in their entireties, such as wild type NK-92, NK-92-CD16, NK-92-CD16-γ, NK-92-CD16-ζ, NK-92-CD16(F176V), NK-92MI and NK-92CI.

Provided herein is a population of modified NK-92 haNK003 cells having antibody-dependent cell-mediated cytotoxicity (ADCC) comprising nucleic acid molecules comprising both CD16 (SEQ ID NO:3) and IL-2 (SEQ ID NO:5), wherein greater than 90% of the cells in the population of cells express CD56, CD16, CD54, and NKp30 and less than 5% of the cells in the population of cells express CD3. Optionally, the nucleic acid molecules are mRNA molecules. Optionally, the mRNA molecules comprise from 5' to 3' a sequence encoding CD16, an IRES sequence, and a sequence encoding IL-2. Optionally, the cells comprise SEQ ID NO:1 on chromosome 17. Optionally, the mean doubling time of the cells is between 55 and 70 hours. Optionally, the population of cells maintains the mean doubling time from 1, 2, 3, 4, 5, 10, 15, 20, 25 or more days. Optionally, the population of cells can be passaged for 1, 2, 3, 4 or more days. Optionally, the cells secrete IL-2 at a concentration of 10 to 40 pg/hour per million cells. Optionally, the cells are irradiated cells.

In response to certain stimuli, CD16 is cleaved close to the cell membrane resulting in release of the extracellular portion of the receptor and down regulation of expression following activation (See, Jing, et al., PLOS one, 10(3): e0121788 DOI:10.1371/journal.pone.0121788 (2015)). Under normal conditions, this mechanism helps to control NK cell cytotoxicity, but in the tumor environment, this can reduce ADCC potency and cancer cell killing. Advantageously, the provided haNK003 cells have enhanced ADCC activity against cancer cells. Without being bound by theory, this is believed to be due to the stable expression of CD16 in haNK003 cells even after ADCC. As shown in the examples below, after activation with phorbol-12-myristate 13-acetate or stimulation with K562 cells, expression of CD16 remained high as compared to control cells. Further, CD16 expression remained high in haNK003 cells even after ADCC. Therefore, the provided haNK003 cells have reduced downregulation of expression of CD16 compared to a control. Further, the haNK003 cells have increased levels of CD16 after ADCC compared to a control. Stated another way, the cells maintain higher levels of CD16 after ADCC compared to a control. Thus, haNK003 cells have more stable expression of CD16 compared to a control, e.g., normal NK cells.

Natural Killer (NK) cell lytic activity is suppressed in hypoxic environments in vitro (1% $O_2$) and is associated with downregulation of NKG2D, perforin and granzyme. There is some variability with NK sensitivity to hypoxia (1% $O_2$) from normal donors. However, NK cell lytic activity can be partially rescued by exogenous IL-2 activation in vitro (16 h, 1000 IU/ml). Further, NK cells retain ADCC capacity at under 1% oxygen conditions. As described in more detail in the examples below, genes associated with hypoxia show no change in expression in haNK cells between 20% oxygen conditions and 0% oxygen (hypoxic) conditions. However, these same genes associated with hypoxia are shown to have reduced expression in normal NK cells.

As noted above, the modified NK-92 cells express the Fc receptor CD16. As used herein, the term "Fc receptor" refers to a protein found on the surface of certain cells (e.g., natural killer cells) that contribute to the protective functions of the immune cells by binding to part of an antibody known as the Fc region. Binding of the Fc region of an antibody to the Fc receptor (FcR) of a cell stimulates phagocytic or cytotoxic activity of a cell via antibody-mediated phagocytosis or antibody-dependent cell-mediated cytotoxicity (ADCC). FcRs are classified by the type of antibody they recognize. For example, Fc-gamma receptors (FCγR) bind to the IgG class of antibodies. FCγRIII-A (also called CD16) is a low affinity Fc receptor that binds to IgG antibodies and activates ADCC. FCγRIII-A are typically found on NK cells. A representative amino acid sequence encoding CD16 is shown in SEQ ID NO:3. A representative polynucleotide sequence encoding CD16 is shown in SEQ ID NO:4. The complete sequences of CD16 can be found in the SwissProt database as entry P08637.

Optionally, the modified NK-92 cells comprise a nucleic acid sequence with 70%, 80%, 90%, or 95% identity to SEQ ID NO:3. Optionally, the modified NK-92 cells comprise a nucleic acid sequence with 90%, 91%, 92%, 93%, 94%, 95%, 96%, 97%, 98% or 99% identity to SEQ ID NO:3. Optionally, the modified NK-92 cells comprise a polypeptide with 70%, 80%, 90%, or 95% identity to SEQ ID NO:4. Optionally, the modified NK-92 cells comprise a polypeptide with 90%, 91%, 92%, 93%, 94%, 95%, 96%, 97%, 98% or 99% identity to SEQ ID NO:4.

The cytotoxicity of NK-92 cells is dependent on the presence of cytokines (e.g., interleukin-2 (IL-2)). The cost of using exogenously added IL-2 needed to maintain and expand NK-92 cells in commercial scale culture is significant. The administration of IL-2 to human subjects in sufficient quantity to continue activation of NK-92 cells would cause adverse side effects. Optionally, the IL-2 is expressed with a signal sequence that directs the IL-2 to the endoplasmic reticulum. Directing the IL-2 to the endoplasmic reticulum permits expression of IL-2 at levels sufficient for autocrine activation and without releasing substantial amounts of IL-2 extracellularly. See Konstantinidis et al "Targeting IL-2 to the endoplasmic reticulum confines autocrine growth stimulation to NK-92 cells" Exp Hematol. 2005 February; 33(2):159-64. A representative nucleic acid encoding IL-2 is shown in SEQ ID NO:5 and a representative polypeptide of IL-2 is shown in SEQ ID NO:6.

Optionally, the modified NK-92 cells comprise a nucleic acid sequence with 70%, 80%, 90%, or 95% identity to SEQ ID NO:5. Optionally, the modified NK-92 cells comprise a nucleic acid sequence with 90%, 91%, 92%, 93%, 94%, 95%, 96%, 97%, 98% or 99% identity to SEQ ID NO:5. Optionally, the modified NK-92 cells comprise a polypeptide with 70%, 80%, 90%, or 95% identity to SEQ ID NO:6. Optionally, the modified NK-92 cells comprise a polypeptide with 90%, 91%, 92%, 93%, 94%, 95%, 96%, 97%, 98% or 99% identity to SEQ ID NO:6. The provided modified NK-92 cells advantageously are capable of being maintained in the absence of IL-2 without secreting IL-2 in an amount to cause a clinical adverse effect.

Nucleic acid, as used herein, refers to deoxyribonucleotides or ribonucleotides and polymers and complements thereof. The term includes deoxyribonucleotides or ribonucleotides in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). Unless otherwise indicated, conservatively modified variants of nucleic acid sequences (e.g., degenerate codon substitutions) and complementary sequences can be used in place of a particular nucleic acid sequence recited herein. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); Rossolini et al., Mol. Cell. Probes 8:91-98 (1994)). The term nucleic acid is used interchangeably with gene, cDNA, mRNA, oligonucleotide, and polynucleotide.

A nucleic acid is operably linked when it is placed into a functional relationship with another nucleic acid sequence. For example, DNA that encodes a presequence or secretory leader is operably linked to DNA that encodes a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are near each other, and, in the case of a secretory leader, contiguous and in reading phase. However, enhancers do not have to be contiguous. For example, a nucleic acid sequence that is operably linked to a second nucleic acid sequence is covalently linked, either directly or indirectly, to such second sequence, although any effective three-dimensional association is acceptable. A single nucleic acid sequence can be operably linked to multiple other sequences. For example, a single promoter can direct transcription of multiple RNA species. Linking can be accomplished by ligation at convenient restriction sites. If such sites do not exist, the synthetic oligonucleotide adaptors or linkers are used in accordance with conventional practice.

The terms identical or percent identity, in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be substantially identical. This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer; subsequence coordinates are designated, if necessary; and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A comparison window, as used herein, includes reference to a segment of any one of the number of contiguous positions selected from the group consisting of from 20 to 600, usually about 50 to about 200, more usually about 100 to about 150, in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, Adv. Appl. Math. 2:482 (1981); by the homology alignment algorithm of Needleman & Wunsch, J. Mol. Biol. 48:443 (1970); by the search for similarity method of Pearson & Lipman, Proc. Nat'l. Acad. Sci. USA 85:2444 (1988); by computerized implementations of these algorithms (GAP, BESTFIT, FASTA, and TFASTA in the Wisconsin Genetics Software Package, Genetics Computer Group, 575 Science Dr., Madison, Wis.); or by manual alignment and visual inspection (see, e.g., Current Protocols in Molecular Biology (Ausubel et al., eds. 1995 supplement)).

A preferred example of an algorithm that is suitable for determining percent sequence identity and sequence similarity are the BLAST and BLAST 2.0 algorithms, which are described in Altschul et al., Nuc. Acids Res. 25:3389-3402 (1977), and Altschul et al., J. Mol. Biol. 215:403-410 (1990), respectively. BLAST and BLAST 2.0 are used, with the parameters described herein, to determine percent sequence identity for nucleic acids or proteins. Software for performing BLAST analyses is publicly available through the National Center for Biotechnology Information, as known in the art. This algorithm involves first identifying high scoring sequence pairs (HSPs) by identifying short words of a selected length (W) in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated for nucleotide sequences using the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The Expectation value (E) represents the number of different alignments with scores equivalent to or better than what is expected to occur in a database search by chance. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, expectation (E) of 10, and the BLOSUM62 scoring matrix (see Henikoff & Henikoff, Proc. Natl. Acad. Sci. USA 89:10915 (1989)), alignments (B) of 50, expectation (E) of 10, M=5, N=−4, and a comparison of both strands.

The term polypeptide, as used herein, generally has its art-recognized meaning of a polymer of at least three amino acids and is intended to include peptides and proteins. However, the term is also used to refer to specific functional classes of polypeptides, such as, for example, desaturases, elongases, etc. For each such class, the present disclosure provides several examples of known sequences of such polypeptides. Those of ordinary skill in the art will appreciate, however, that the term polypeptide is intended to be sufficiently general as to encompass not only polypeptides having the complete sequence recited herein (or in a reference or database specifically mentioned herein), but also to encompass polypeptides that represent functional fragments (i.e., fragments retaining at least one activity) of such complete polypeptides. Moreover, those in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term polypeptide as used herein. Those in the art can determine other regions of similarity and/or identity by analysis of the sequences of various polypeptides described herein. As is known by those in the art, a variety of strategies are known and tools are available for performing comparisons of amino acid or nucleotide sequences to assess degrees of identity and/or similarity. These strategies include, for example, manual alignment, computer assisted sequence alignment and combinations thereof. A number of algorithms (which are generally computer implemented) for performing sequence alignment are widely available, or can be produced by one of skill in the art. Representative algorithms include, e.g., the local homology algorithm of Smith and Waterman (Adv. Appl. Math., 1981, 2: 482); the homology alignment algorithm of Needleman and Wunsch (J. Mol. Biol., 1970, 48: 443); the search for similarity method of Pearson and Lipman (Proc. Natl. Acad. Sci. (USA), 1988, 85: 2444); and/or by computerized implementations of these algorithms (e.g., GAP, BESTFIT, FASTA, and TFASTA in the Wisconsin Genetics Software Package Release 7.0, Genetics Computer Group, 575 Science Dr., Madison, Wis.). Readily available computer programs incorporating such algorithms include, for example, BLASTN, BLASTP, Gapped BLAST, PILEUP, CLUSTALW, etc. When utilizing BLAST and Gapped BLAST programs, default parameters of the respective programs may be used. Alternatively, the practitioner may use non-default parameters depending on his or her experimental and/or other requirements (see for example, the Web site having URL www.ncbi.nlm.nih.gov).

As used herein, the terms promoter, promoter element, and regulatory sequence refer to a polynucleotide that regulates expression of a selected polynucleotide sequence operably linked to the promoter, and that effects expression of the selected polynucleotide sequence in cells.

The term transformation as used herein refers to a process by which an exogenous or heterologous nucleic acid molecule (e.g., a vector or recombinant nucleic acid molecule) is introduced into a recipient cell or microorganism. The exogenous or heterologous nucleic acid molecule may or may not be integrated into (i.e., covalently linked to) chromosomal DNA making up the genome of the host cell or microorganism. For example, the exogenous or heterologous polynucleotide may be maintained on an episomal element, such as a plasmid. Alternatively or additionally, the exogenous or heterologous polynucleotide may become integrated into a chromosome so that it is inherited by daughter cells through chromosomal replication. Methods for transformation include, but are not limited to, calcium phosphate precipitation; fusion of recipient cells with bacterial protoplasts containing the recombinant nucleic acid; treatment of the recipient cells with liposomes containing the recombinant nucleic acid; DEAE dextran; fusion using polyethylene glycol (PEG); electroporation; magnetoporation; biolistic delivery; retroviral infection; lipofection; and micro-injection of DNA directly into cells.

The term transformed, as used in reference to cells, refers to cells that have undergone transformation as described herein such that the cells carry exogenous or heterologous genetic material (e.g., a recombinant nucleic acid). The term transformed can also or alternatively be used to refer to microorganisms, strains of microorganisms, tissues, organisms, etc. that contain exogenous or heterologous genetic material.

The terms modified and recombinant when used with reference to a cell, nucleic acid, polypeptide, vector, or the like indicates that the cell, nucleic acid, polypeptide, vector or the like has been modified by or is the result of laboratory methods and is non-naturally occurring. Thus, for example, modified cells include cells produced by or modified by laboratory methods, e.g., transformation methods for introducing nucleic acids into the cell. Modified cells can include nucleic acid sequences not found within the native (non-recombinant) form of the cells or can include nucleic acid sequences that have been altered, e.g., linked to a non-native promoter.

As described herein, a control or standard control refers to a sample, measurement, or value that serves as a reference, usually a known reference, for comparison to a test sample, measurement, or value. For example, a test cell, e.g., a cell transformed with nucleic acid sequences encoding genes for an Fc Receptor can be compared to a known normal (wild-type) cell (e.g., a standard control cell). A standard control can also represent an average measurement or value gathered from a population of cells (e.g., standard control microorganisms) that do not express the Fc Receptor or that do not have or have minimal levels of Fc Receptor activity. One of skill will recognize that standard controls can be designed for assessment of any number of parameters (e.g., RNA levels, polypeptide levels, specific cell types, and the like).

As used herein, the term "antibody" refers to an immunoglobulin or fragment thereof. The antibody may be of any type (e.g., IgG, IgA, IgM, IgE or IgD). Preferably, the antibody is IgG. An antibody may be non-human (e.g., from mouse, goat, or any other animal), fully human, humanized, or chimeric. An antibody may be polyclonal or monoclonal. Optionally, the antibody is monoclonal.

The term "monoclonal antibody" as used herein, refers to a pure, target-specific antibody produced from a single clone of cells grown in culture and that is capable of indefinitely proliferating. Monoclonal antibodies that may be used include naked antibodies, that attach to and block antigens on cancerous cells. Optionally, the naked monoclonal antibody is alemtuzumab, which binds to the CD52 antigen in lymphocytes. Also included in the monoclonal antibodies that may be used are conjugated monoclonal antibodies, such as tagged, labeled, or loaded antibodies. Specifically, the antibodies may be tagged or loaded with a drug or a toxin, or radioactively labeled. Examples of such antibodies include, but are not limited to, ibritumomab, which targets the CD20 antigen; brentuximab, which targets the CD30 antigen, and trastuzumab, which targets the HER2 protein. Other monoclonal antibodies that may be used are bispecific monoclonal antibodies, such as blinatunomab, which targets CD19 in lymphoma cells, and CD3 in T cells.

As used herein, the term "antibody fragment" refers to any portion of the antibody that recognizes an epitope. Antibody fragments may be glycosylated. By way of non-limiting example, the antibody fragment may be a Fab fragment, a Fab' fragment, a F(ab')2 fragment, a Fv fragment, an rIgG fragment, a functional antibody fragment, single chain recombinant forms of the foregoing, and the like. F(ab')2, Fab, Fab' and Fv are antigen-binding fragments that can be generated from the variable region of IgG and IgM. They vary in size, valency, and Fc content. The fragments may be generated by any method, including expression of the constituents (e.g., heavy and light chain portions) by a cell or cell line, or multiple cells or cell lines. Preferably, the antibody fragment recognizes the epitope and contains a sufficient portion of an Fc region such that it is capable of binding an Fc receptor.

As used herein, the term "cancer" refers to all types of cancer, neoplasm, or malignant tumors found in mammals, including leukemia, carcinomas and sarcomas. Exemplary cancers include cancer of the brain, breast, cervix, colon, head & neck, liver, kidney, lung, non-small cell lung, melanoma, mesothelioma, ovary, sarcoma, stomach, uterus and medulloblastoma. Additional examples include, Hodgkin's Disease, Non-Hodgkin's Lymphoma, multiple myeloma, neuroblastoma, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine and exocrine pancreas, and prostate cancer.

Also provided are methods of treating subjects with modified NK-92 cells as described herein. Optionally, the subject is treated with the modified NK-92 cell and an antibody.

Modified NK-92 cells can be administered to a subject by absolute numbers of cells, e.g., said subject can be administered from about 1000 cells/injection to up to about 10 billion cells/injection, such as at about, at least about, or at most about, $1\times10^{10}$, $1\times10^{9}$, $1\times10^{8}$, $1\times10^{7}$, $5\times10^{7}$, $1\times10^{6}$, $5\times10^{6}$, $1\times10^{5}$, $5\times10^{5}$, $1\times10^{4}$, $5\times10^{4}$, $1\times10^{3}$, $5\times10^{3}$ (and so forth) NK-92 cells per injection, or any ranges between any two of the numbers, end points inclusive. Optionally, from $1\times10^{8}$ to $1\times10^{10}$ cells are administered to the subject. Optionally, the cells are administered one or more times weekly for one or more weeks. Optionally, the cells are administered once or twice weekly for 1, 2, 3, 4, 5, 6, 7, 8, 9, 10 or more weeks.

Optionally, subject are administered from about 1000 cells/injection/$m^2$ to up to about 10 billion cells/injection/$m^2$, such as at about, at least about, or at most about, $1\times10^{8}/m^2$, $1\times10^{7}/m^2$, $5\times10^{7}/m^2$, $1\times10^{6}/m^2$, $5\times10^{6}/m^2$, $1\times10^{5}/m^2$, $5\times10^{5}/m^2$, $1\times10^{4}/m^2$, $5\times10^{4}/m^2$, $1\times10^{3}/m^2$, $5\times10^{3}/m^2$ (and so forth) NK-92 cells per injection, or any ranges between any two of the numbers, end points inclusive.

Optionally, NK-92 cells can be administered to such individual by relative numbers of cells, e.g., said individual can be administered about 1000 cells to up to about 10 billion cells per kilogram of the individual, such as at about, at least about, or at most about, $1\times10^{8}$, $1\times10^{7}$, $5\times10^{7}$, $1\times10^{6}$, $5\times10^{6}$, $1\times10^{5}$, $5\times10^{5}$, $1\times10^{4}$, $5\times10^{4}$, $1\times10^{3}$, $5\times10^{3}$ (and so forth) NK-92 cells per kilogram of the individual, or any ranges between any two of the numbers, end points inclusive.

Optionally, the total dose may calculated by $m^2$ of body surface area, including about $1\times10^{11}$, $1\times10^{10}$, $1\times10^{9}$, $1\times10^{8}$, $1\times10^{7}$, per $m^2$, or any ranges between any two of the numbers, end points inclusive. Optionally, between about 1 billion and about 3 billion NK-92 cells are administered to a patient. Optionally, the amount of NK-92 cells injected per dose may calculated by m2 of body surface area, including $1\times10^{11}$, $1\times10^{10}$, $1\times10^{9}$, $1\times10^{8}$, $1\times10^{7}$, per $m^2$.

The NK-92 cells, and optionally other anti-cancer agents can be administered once to a patient with cancer can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

Optionally, NK-92 cells are administered in a composition comprising NK-92 cells and a medium, such as human serum or an equivalent thereof. Optionally, the medium comprises human serum albumin. Optionally, the medium comprises human plasma. Optionally, the medium comprises about 1% to about 15% human serum or human serum equivalent.

Optionally, the medium comprises about 1% to about 10% human serum or human serum equivalent. Optionally, the medium comprises about 1% to about 5% human serum or human serum equivalent. Optionally, the medium comprises about 2.5% human serum or human serum equivalent. Optionally, the serum is human AB serum. Optionally, a serum substitute that is acceptable for use in human therapeutics is used instead of human serum. Such serum substitutes may be known in the art. Optionally, NK-92 cells are administered in a composition comprising NK-92 cells and an isotonic liquid solution that supports cell viability. Optionally, NK-92 cells are administered in a composition that has been reconstituted from a cryopreserved sample.

According to the methods provided herein, the subject is administered an effective amount of one or more of the agents provided herein. The terms effective amount and effective dosage are used interchangeably. The term effective amount is defined as any amount necessary to produce a desired physiologic response (e.g., reduction of inflammation). Effective amounts and schedules for administering the agent may be determined empirically by one skilled in the art. The dosage ranges for administration are those large enough to produce the desired effect in which one or more symptoms of the disease or disorder are affected (e.g., reduced or delayed). The dosage should not be so large as to cause substantial adverse side effects, such as unwanted cross-reactions, anaphylactic reactions, and the like. Generally, the dosage will vary with the age, condition, sex, type of disease, the extent of the disease or disorder, route of administration, or whether other drugs are included in the regimen, and can be determined by one of skill in the art. The dosage can be adjusted by the individual physician in the event of any contraindications. Dosages can vary and can be administered in one or more dose administrations daily, for one or several days. Guidance can be found in the literature for appropriate dosages for given classes of pharmaceutical products. For example, for the given parameter, an effective amount will show an increase or decrease of at least 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least a 1.2-fold, 1.5-fold, 2-fold, 5-fold, or more effect over a control. The exact dose and formulation will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Remington: The Science and Practice of Pharmacy, 22nd Edition, Gennaro, Editor (2012), and Pickar, Dosage Calculations (1999)).

Pharmaceutically acceptable compositions can include a variety of carriers and excipients. A variety of aqueous carriers can be used, e.g., buffered saline and the like. These solutions are sterile and generally free of undesirable matter. Suitable carriers and excipients and their formulations are described in Remington: The Science and Practice of Pharmacy, 21st Edition, David B. Troy, ed., Lippicott Williams & Wilkins (2005). By pharmaceutically acceptable carrier is meant a material that is not biologically or otherwise undesirable, i.e., the material is administered to a subject without causing undesirable biological effects or interacting in a deleterious manner with the other components of the pharmaceutical composition in which it is contained. If administered to a subject, the carrier is optionally selected to minimize degradation of the active ingredient and to minimize adverse side effects in the subject. As used herein, the term pharmaceutically acceptable is used synonymously with physiologically acceptable and pharmacologically acceptable. A pharmaceutical composition will generally comprise agents for buffering and preservation in storage and can include buffers and carriers for appropriate delivery, depending on the route of administration.

The compositions may contain acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of cells in these formulations and/or other agents can vary and will be selected primarily based on fluid volumes, viscosities, body weight and the like in accordance with the particular mode of administration selected and the subject's needs.

Optionally, the NK-92 cells are administered to the subject in conjunction with one or more other treatments for the cancer being treated. Without being bound by theory, it is believed that co-treatment of a subject with NK-92 cells and another therapy for the cancer will allow the NK-92 cells and the alternative therapy to give the endogenous immune system a chance to clear the cancer that heretofore had overwhelmed such endogenous action. Optionally, two or more other treatments for the cancer being treated includes, for example, an antibody, radiation, chemotherapeutic, stem cell transplantation, or hormone therapy.

Optionally, an antibody is administered to the patient in conjunction with the NK-92 cells. Optionally, the NK-92 cells and an antibody are administered to the subject together, e.g., in the same formulation; separately, e.g., in separate formulations, concurrently; or can be administered separately, e.g., on different dosing schedules or at different times of the day. When administered separately, the antibody can be administered in any suitable route, such as intravenous or oral administration.

Optionally, antibodies may be used to target cancerous cells or cells that express cancer-associated markers. A number of antibodies have been approved for the treatment of cancer, alone.

TABLE 2

Example FDA approved therapeutic monoclonal antibodies

| Antibody | Brand name | Company | Target | Indication (Targeted disease) |
|---|---|---|---|---|
| Alemtuzumab | Campath ® | Genzyme | CD52 | Chronic lymphocytic leukemia |
| Brentuximab vedotin | Adcetris ® | | CD30 | Anaplastic large cell lymphoma (ALCL) and Hodgkin lymphoma |
| Cetuximab | Erbitux ® | Bristol-Myers Squibb/Eli Lilly/Merck KGaA | epidermal growth factor receptor | Colorectal cancer, Head and neck cancer |
| Gemtuzumab | Mylotarg ® | Wyeth | CD33 | Acute myelogenous leukemia (with calicheamicin) |

TABLE 2-continued

Example FDA approved therapeutic monoclonal antibodies

| Antibody | Brand name | Company | Target | Indication (Targeted disease) |
|---|---|---|---|---|
| Ibritumomab tiuxetan | Zevalin ® | Spectrum Pharmaceuticals, Inc. | CD20 | Non-Hodgkin lymphoma (with yttrium-90 or indium-111) |
| Ipilimumab (MDX-101) | Yervoy ® | | blocks CTLA-4 | Melanoma |
| Ofatumumab | Arzerra ® | | CD20 | Chronic lymphocytic leukemia |
| Palivizumab | Synagis ® | MedImmune | an epitope of the RSV F protein | Respiratory Syncytial Virus |
| Panitumumab | Vectibix ® | Amgen | epidermal growth factor receptor | Colorectal cancer |
| Rituximab | Rituxan ®, Mabthera ® | Biogen Idec/Genentech | CD20 | Non-Hodgkin lymphoma |
| Tositumomab | Bexxar ® | GlaxoSmithKline | CD20 | Non-Hodgkin lymphoma |
| Trastuzumab | Herceptin ® | Genentech | ErbB2 | Breast cancer |
| Blinatunomab | | | bispecific CD19-directed CD3 T-cell engager | Philadelphia chromosome-negative relapsed or refractory B cell precursor acute lymphoblastic leukemia (ALL) |
| Avelumamab | | | anti-PD-L1 | Non-small cell lung cancer, metastatic Merkel cell carcinoma; gastic cancer, breast cancer, ovarian cancer, bladder cancer, melanoma, meothelioma, including metastatic or locally advanced solid tumors |
| Daratumumab | | | CD38 | Multiple myeloma |
| Elotuzumab | | | a SLAMF7-directed (also known as CD 319) immunostimulatory antibody | Multiple myeloma |

Antibodies may treat cancer through a number of mechanisms. ADCC occurs when immune cells, such as NK cells, bind to antibodies that are bound to target cells through Fc receptors, such as CD16.

Accordingly, NK-92 cells that express CD16 are administered to a subject along with an effective amount of at least one monoclonal antibody directed against a specific cancer-associated protein, for example, alemtuzumab, bevacizumab, ibritumomab tiuxetan, ofatumumab, rituximab, and trastuzumab. Optionally, the monoclonal antibody is a naked monoclonal antibody, a conjugated monoclonal antibody or a bispecific monoclonal antibody. Optionally, a bispecific antibody can be used that binds the cancer cell and also binds a cell-surface protein present on the surface of NK-92 cells.

Cancer-specific antibodies bind to particular protein antigens that are expressed on the surfaces of cancer cells. NK-92 cells can be modified such that an antibody is associated with the NK-92 cell surface. Optionally, the antibody is specific for the cancer. In this way, the NK-92 cell can be specifically targeted to the cancer. Neutralizing antibodies may also be isolated. For example, a secreted glycoprotein, YKL-40, is elevated in multiple types of advanced human cancers. It is contemplated that an antibody to YKL-40 could be used to restrain tumor growth, angiogenesis and/or metastasis. See Faibish et al., (2011) Mol. Cancer Ther. 10(5):742-751.

Antibodies to cancer can be purchased from commercially available sources or can be produced by any method known in the art. For example, antibodies can be produced by obtaining B cells, bone marrow, or other samples from previously one or more patients who were infected by the cancer and recovered or were recovering when the sample was taken. Methods of identifying, screening, and growing antibodies (e.g., monoclonal antibodies) from these samples are known. For example, a phage display library can be made by isolating RNA from the sample or cells of interest, preparing cDNA from the isolated RNA, enriching the cDNA for heavy-chain and/or light-chain cDNA, and creating libraries using a phage display vector. Libraries can be prepared and screened as described, for example, in Maruyama, et al., which is incorporated herein by reference in its entirety. Antibodies can be made by recombinant methods or any other method. Isolation, screening, characterization, and production of human monoclonal antibodies are also described in Beerli, et al., PNAS (2008) 105(38): 14336-14341, which is incorporated herein by reference in its entirety.

Combinations of agents or compositions can be administered either concomitantly (e.g., as a mixture), separately but simultaneously (e.g., via separate intravenous lines) or sequentially (e.g., one agent is administered first followed by administration of the second agent). Thus, the term combination is used to refer to concomitant, simultaneous, or sequential administration of two or more agents or compositions. The course of treatment is best determined on an individual basis depending on the particular characteristics of the subject and the type of treatment selected. The treatment, such as those disclosed herein, can be administered to the subject on a daily, twice daily, bi-weekly, monthly, or any applicable basis that is therapeutically effective. The treatment can be administered alone or in combination with any other treatment disclosed herein or known in the art. The additional treatment can be administered simultaneously with the first treatment, at a different time, or on an entirely different therapeutic schedule (e.g., the first treatment can be daily, while the additional treatment is weekly).

Also disclosed are kits comprising the provided modified NK-92 cells. Optionally, the kits further include one or more additional agents such as antibodies. The components of the kit may be contained in one or different containers such as one or more vials. The antibody may be in liquid or solid form (e.g., after lyophilization) to enhance shelf-life. If in liquid form, the components may comprise additives such as stabilizers and/or preservatives such as proline, glycine, or sucrose or other additives that enhance shelf-life.

Optionally, the kit may contain additional compounds such as therapeutically active compounds or drugs that are to be administered before, at the same time, or after administration of the modified NK-92 cells or NK-92 cells and antibody. Examples of such compounds include vitamins, minerals, fludrocortisone, ibuprofen, lidocaine, quinidine, chemotherapeutic, and the like.

Optionally, instructions for use of the kits will include directions to use the kit components in the treatment of a cancer. The instructions may further contain information regarding how to prepare (e.g., dilute or reconstitute, in the case of freeze-dried protein) the antibody and the NK-92 cells (e.g., thawing and/or culturing). The instructions may further include guidance regarding the dosage and frequency of administration.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed while, specific references to each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

The examples below are intended to further illustrate certain aspects of the methods and compositions described herein, and are not intended to limit the scope of the claims.

EXAMPLES

Example 1. Structural and Functional Characteristics of haNK003

NK-92 [CD16.176V, ER IL-2] (haNK003) was generated through the modification of NK-92 cells. NK-92 cells were originally isolated in 1992 from a 50-year-old male patient with rapidly progressive non-Hodgkin's lymphoma (Gong, et al., Leukemia, 8(4):652-8 (1994)). The NK-92 cell line was subsequently characterized and shown to be phenotypically CD56+, CD3−, and CD16−, as well as IL-2 dependent. haNK003 is an allogeneic cell line that was created through stable transfection by electroporation of NK-92 cells with a bicistronic plasmid-based vector containing sequences for CD16 and IL-2. The transfected plasmid is shown in FIG. 1 and was constructed by GeneArt AG. The CD16 sequence codes for a valine at amino acid 176 (176V), which allows for increased potential for antibody-dependent cell-mediated cytotoxicity (ADCC). The IL-2 sequence is tagged with the endoplasmic reticulum retention signal, KDEL, to prevent IL-2 protein secretion from the endoplasmic reticulum (ER). Inclusion of the IL-2 sequence allows haNK™ to be IL-2 independent.

EUFETS GmbH (Regensburg, Germany) conducted the transfection by electroporation and selected multiple clones by one round of limiting dilution. A single clone from EUFETS was sent to BioReliance in order to establish a GMP master cell bank, haNK003. Whole genome sequencing on the selected clone confirmed that the plasmid insertion site is at a single location on Chromosome 17 at position 15,654,977-15,661,403.

Transfection Plasmid

A plasmid was constructed by GeneArt AG based on provided specifications. The synthetic gene pNEUKv1_FcRIL2 was assembled from synthetic oligonucleotides and PCR products. The fragment was cloned into the pNEUKv1_O059 vector backbone using EcoRI and NotI restriction sites. The pNEUKv1_O059 is a synthetic vector, containing an ampicillin resistance cassette. The promoter used for expression of the transgene is EF-1alpha with an SV40 polyadenylation sequence. The resulting plasmid is 5,491 base pairs (bp) in length and contains human origin sequences for CD16 and IL-2. Neither CD16 nor IL-2 have any transforming properties. The plasmid DNA was purified from transformed bacteria and its concentration was determined by UV spectroscopy. The final construct was verified by sequencing. The sequence congruence within the used restriction sites was 100%. The plasmid was made under TSE-free production conditions.

The full nucleotide sequence of the pNEUKv1_FcRIL2 plasmid (SEQ ID NO:1) is shown here:

```
  1 TGTATTTAGA AAAATAAACA AATAGGGGTT CCGCGCACAT TTCCCCGAAA AGTGCCACCT
 61 GACGTCGACG GATCGGGAGA TCTCCCGATC CCCTATGGTG CACTCTCAGT ACAATCTGCT
121 CTGATGCCGC ATAGTTAAGC CAGTATCTGC TCCCTGCTTG TGTGTTGGAG GTCGCTGAGT
181 AGTGCGCGAG CAAAATTTAA GCTACAACAA GGCAAGGCTT GACCGACAAT TGCATGAAGA
```

-continued

```
 241 ATCTGCTTAG GGTTAGGCGT TTTGCGCTGC TTCGGGATCC GCTGACCAAA AGAGCACCAA
 301 AGGCGCCCTG ACCTTCAGCC CCTACCTGCG CTCCGGTGCC CGTCAGTGGG CAGAGCGCAC
 361 ATCGCCCACA GTCCCCGAGA AGTTGGGGGG AGGGGTCGGC AATTGAACCG GTGCCTAGAG
 421 AAGGTGGCGC GGGGTAAACT GGGAAAGTGA TGTCGTGTAC TGGCTCCGCC TTTTTCCCGA
 481 GGGTGGGGGA GAACCGTATA TAAGTGCAGT AGTCGCCGTG AACGTTCTTT TTCGCAACGG
 541 GTTTGCCGCC AGAACACAGG TAAGTGCCGT GTGTGGTTCC CGCGGGCCTG GCCTCTTTAC
 601 GGGTTATGGC CCTTGCGTGC CTTGAATTAC TTCCACCTGG CTGCAGTACG TGATTCTTGA
 661 TCCCGAGCTT CGGGTTGGAA GTGGGTGGGA GAGTTCGAGG CCTTGCGCTT AAGGAGCCCC
 721 TTCGCCTCGT GCTTGAGTTG AGGCCTGGCC TGGGCGCTGG GGCCGCCGCG TGCGAATCTG
 781 GTGGCACCTT CGCGCCTGTC TCGCTGCTTT CGATAAGTCT CTAGCCATTT AAAATTTTTG
 841 ATGACCTGCT GCGACGCTTT TTTTCTGGCA AGATAGTCTT GTAAATGCGG GCCAAGATCT
 901 GCACACTGGT ATTTCGGTTT TTGGGGCCGC GGGCGGCGAC GGGGCCCGTG CGTCCCAGCG
 961 CACATGTTCG GCGAGGCGGG GCCTGCGAGC GCGGCCACCG AGAATCGGAC GGGGGTAGTC
1021 TCAAGCTGGC CGGCCTGCTC TGGTGCCTGG CCTCGCGCCG CCGTGTATCG CCCCGCCCTG
1081 GGCGGCAAGG CTGGCCCGGT CGGCACCAGT TGCGTGAGCG GAAAGATGGC CGCTTCCCGG
1141 CCCTGCTGCA GGGAGCTCAA AATGGAGGAC GCGGCGCTCG GGAGAGCGGG CGGGTGAGTC
1201 ACCCACACAA AGGAAAAGGG CCTTTCCGTC CTCAGCCGTC GCTTCATGTG ACTCCACGGA
1261 GTACCGGGCG CCGTCCAGGC ACCTCGATTA GTTCTCGAGC TTTTGGAGTA CGTCGTCTTT
1321 AGGTTGGGGG GAGGGGTTTT ATGCGATGGA GTTTCCCCAC ACTGAGTGGG TGGAGACTGA
1381 AGTTAGGCCA GCTTGGCACT TGATGTAATT CTCCTTGGAA TTTGCCCTTT TTGAGTTTGG
1441 ATCTTGGTTC ATTCTCAAGC CTCAGACAGT GGTTCAAAGT TTTTTTCTTC CATTTCAGGT
1501 GTCGTGATAA TACGACTCAC TATAGGGAGA CCCAAGCTGG AATTCGCCAC CATGTGGCAG
1561 CTGCTGCTGC CTACAGCTCT CCTGCTGCTG GTGTCCGCCG GCATGAGAAC CGAGGATCTG
1621 CCTAAGGCCG TGGTGTTCCT GGAACCCCAG TGGTACAGAG TGCTGGAAAA GGACAGCGTG
1681 ACCCTGAAGT GCCAGGGCGC CTACAGCCCC GAGGACAATA GCACCCAGTG GTTCCACAAC
1741 GAGAGCCTGA TCAGCAGCCA GGCCAGCAGC TACTTCATCG ACGCCGCCAC CGTGGACGAC
1801 AGCGGCGAGT ATAGATGCCA GACCAACCTG AGCACCCTGA GCGACCCCGT GCAGCTGGAA
1861 GTGCACATCG GATGGCTGCT GCTGCAGGCC CCCAGATGGG TGTTCAAAGA AGAGGACCCC
1921 ATCCACCTGA GATGCCACTC TTGGAAGAAC ACCGCCCTGC ACAAAGTGAC CTACCTGCAG
1981 AACGGCAAGG GCAGAAAGTA CTTCCACCAC AACAGCGACT TCTACATCCC CAAGGCCACC
2041 CTGAAGGACT CCGGCTCCTA CTTCTGCAGA GGCCTCGTGG GCAGCAAGAA CGTGTCCAGC
2101 GAGACAGTGA ACATCACCAT CACCCAGGGC CTGGCCGTGT CTACCATCAG CAGCTTTTTC
2161 CCACCCGGCT ACCAGGTGTC CTTCTGCCTC GTGATGGTGC TGCTGTTCGC CGTGGACACC
2221 GGCCTGTACT TCAGCGTGAA ACAAACATC AGAAGCAGCA CCCGGGACTG AAGGACCAC
2281 AAGTTCAAGT GGCGGAAGGA CCCCCAGGAC AAGTGAAATT CCGCCCCTCT CCCCCCCCCC
2341 CCTCTCCCTC CCCCCCCCCT AACGTTACTG GCCGAAGCCG CTTGGAATAA GGCCGGTGTG
2401 CGTTTGTCTA TATGTTATTT TCCACCATAT TGCCGTCTTT TGGCAATGTG AGGGCCCGGA
2461 AACCTGGCCC TGTCTTCTTG ACGAGCATTC CTAGGGGTCT TTCCCCTCTC GCCAAAGGAA
2521 TGCAAGGTCT GTTGAATGTC GTGAAGGAAG CAGTTCCTCT GGAAGCTTCT TGAAGACAAA
2581 CAACGTCTGT AGCGACCCTT TGCAGGCAGC GGAACCCCCC ACCTGGCGAC AGGTGCCTCT
2641 GCGGCCAAAA GCCACGTGTA TAAGATACAC CTGCAAAGGC GGCACAACCC CAGTGCCACG
```

```
2701  TTGTGAGTTG GATAGTTGTG GAAAGAGTCA AATGGCTCTC CTCAAGCGTA TTCAACAAGG
2761  GGCTGAAGGA TGCCCAGAAG GTACCCCATT GTATGGGATC TGATCTGGGG CCTCGGTGCA
2821  CATGCTTTAC ATGTGTTTAG TCGAGGTTAA AAAAACGTCT AGGCCCCCCG AACCACGGGG
2881  ACGTGGTTTT CCTTTGAAAA ACACGATAAC CGCCACCATG TACCGGATGC AGCTGCTGAG
2941  CTGTATCGCC CTGTCTCTGG CCCTCGTGAC CAACAGCGCC CCTACCAGCA GCAGCACCAA
3001  GAAAACCCAG CTGCAGCTGG AACATCTGCT GCTGGACCTG CAGATGATCC TGAACGGCAT
3061  CAACAACTAC AAGAACCCCA AGCTGACCCG GATGCTGACC TTCAAGTTCT ACATGCCCAA
3121  GAAGGCCACC GAACTGAAAC ATCTGCAGTG CCTGGAAGAG GAACTGAAGC CCCTGGAAGA
3181  AGTGCTGAAC CTGGCCCAGA GCAAGAACTT CCACCTGAGG CCCAGGGACC TGATCAGCAA
3241  CATCAACGTG ATCGTGCTGG AACTGAAAGG CAGCGAGACA ACCTTCATGT GCGAGTACGC
3301  CGACGAGACA GCTACCATCG TGGAATTTCT GAACCGGTGG ATCACCTTCT GCCAGAGCAT
3361  CATCAGCACC CTGACCGGCT CCGAGAAGGA CGAGCTGTGA GCGGCCGCCC GCTGATCAGC
3421  CTCGAACGAG ATTTCGATTC CACCGCCGCC TTCTATGAAA GGTTGGGCTT CGGAATCGTT
3481  TTCCGGGACG CCGGCTGGAT GATCCTCCAG CGCGGGGATC TCATGCTGGA GTTCTTCGCC
3541  CACCCCAACT TGTTTATTGC AGCTTATAAT GGTTACAAAT AAAGCAATAG CATCACAAAT
3601  TTCACAAATA AAGCATTTTT TCACTGCAT TCTAGTTGTG GTTTGTCCAA ACTCATCAAT
3661  GTATCTTATC ATGTCTGTGC GGTGGGCTCT ATGGCTTCTG AGGCGGAAAG AACCAGCTGG
3721  GGCTCTAGGG GGTATCCCCG GATCCTGAGC AAAAGGCCAG CAAAAGGCCA GGAACCGTAA
3781  AAAGGCCGCG TTGCTGGCGT TTTTCCATAG GCTCCGCCCC CCTGACGAGC ATCACAAAAA
3841  TCGACGCTCA AGTCAGAGGT GGCGAAACCC GACAGGACTA TAAAGATACC AGGCGTTTCC
3901  CCCTGGAAGC TCCCTCGTGC GCTCTCCTGT TCCGACCCTG CCGCTTACCG GATACCTGTC
3961  CGCCTTTCTC CCTTCGGGAA GCGTGGCGCT TTCTCATAGC TCACGCTGTA GGTATCTCAG
4021  TTCGGTGTAG GTCGTTCGCT CCAAGCTGGG CTGTGTGCAC GAACCCCCCG TTCAGCCCGA
4081  CCGCTGCGCC TTATCCGGTA ACTATCGTCT TGAGTCCAAC CCGGTAAGAC ACGACTTATC
4141  GCCACTGGCA GCAGCCACTG GTAACAGGAT TAGCAGAGCG AGGTATGTAG GCGGTGCTAC
4201  AGAGTTCTTG AAGTGGTGGC CTAACTACGG CTACACTAGA AGAACAGTAT TTGGTATCTG
4261  CGCTCTGCTG AAGCCAGTTA CCTTCGGAAA AAGAGTTGGT AGCTCTTGAT CCGGCAAACA
4321  AACCACCGCT GGTAGCGGTG GTTTTTTTGT TTGCAAGCAG CAGATTACGC GCAGAAAAAA
4381  AGGATCTCAA GAAGATCCTT TGATCTTTTC TACGGGGTCT GACGCTCAGT GGAACGAAAA
4441  CTCACGTTAA GGGATTTTGG TCATGAGATT ATCAAAAAGG ATCTTCACCT AGATCCTTTT
4501  AAATTAAAAA TGAAGTTTTA AATCAATCTA AAGTATATAT GAGTAAACTT GGTCTGACAG
4561  TTACCAATGC TTAATCAGTG AGGCACCTAT CTCAGCGATC TGTCTATTTC GTTCATCCAT
4621  AGTTGCCTGA CTCCCCGTCG TGTAGATAAC TACGATACGG GAGGGCTTAC CATCTGGCCC
4681  CAGTGCTGCA ATGATACCGC GAGAACCACG CTCACCGGCT CCAGATTTAT CAGCAATAAA
4741  CCAGCCAGCC GGAAGGGCCG AGCGCAGAAG TGGTCCTGCA ACTTTATCCG CCTCCATCCA
4801  GTCTATTAAT TGTTGCCGGG AAGCTAGAGT AAGTAGTTCG CCAGTTAATA GTTTGCGCAA
4861  CGTTGTTGCC ATTGCTACAG GCATCGTGGT GTCACGCTCG TCGTTTGGTA TGGCTTCATT
4921  CAGCTCCGGT TCCCAACGAT CAAGGCGAGT TACATGATCC CCCATGTTGT GCAAAAAAGC
4981  GGTTAGCTCC TTCGGTCCTC CGATCGTTGT CAGAAGTAAG TTGGCCGCAG TGTTATCACT
5041  CATGGTTATG GCAGCACTGC ATAATTCTCT TACTGTCATG CCATCCGTAA GATGCTTTTC
```

```
-continued
5101 TGTGACTGGT GAGTACTCAA CCAAGTCATT CTGAGAATAG TGTATGCGGC GACCGAGTTG

5161 CTCTTGCCCG GCGTCAATAC GGGATAATAC CGCGCCACAT AGCAGAACTT TAAAAGTGCT

5221 CATCATTGGA AAACGTTCTT CGGGGCGAAA ACTCTCAAGG ATCTTACCGC TGTTGAGATC

5281 CAGTTCGATG TAACCCACTC GTGCACCCAA CTGATCTTCA GCATCTTTTA CTTTCACCAG

5341 CGTTTCTGGG TGAGCAAAAA CAGGAAGGCA AAATGCCGCA AAAAAGGGAA TAAGGGCGAC

5401 ACGGAAATGT TGAATACTCA TACTCTTCCT TTTTCAATAT TATTGAAGCA TTTATCAGGG

5461 TTATTGTCTC ATGAGCGGAT ACATATTTGA A
```

To generate the haNK003 cell line, a vial of the NK-92 (aNK) Master Cell Bank (MCB) (aNK COA) and 250 mg of pNEUKv1_FcRIL2 plasmid were sent to EUFETS GmbH. EUFETS thawed the MCB vial and cultured the NK-92 cells to an adequate number for transfection with the plasmid. The transfected cells were grown in media with IL-2, X-Vivo 10, and 5% heat inactivated Human AB Serum for the first two days post transfection. After two days, IL-2 was no longer added to the growth media and any cells that were transfected and producing adequate amount of IL-2 continued to grow. Multiple clones were isolated by limiting dilution and preliminarily screened for phenotype and Fc Receptor expression. Six (6) clones that exhibited good viability (>70%), acceptable doubling time, expected phenotype and positive Fc Receptor expression were sent to the German Red Cross GMP Testing Laboratory (GRC) for more extensive screening and final selection of a single clone. At GRC, all clones were tested for phenotype (including Fc Receptor expression), ADCC, cytokine profile, growth characteristics, and radiation sensitivity. The selected cell line, haNK003, was used to generate the master cell bank.

NantKwest Master Cell Bank (MCB haNK003) was manufactured from the selected cell line and tested by BioReliance. The MCB was tested for purity, potency, identity, sterility and viral/adventitious agents. The MCB is cryopreserved in a formulation of 10% DMSO, 40% X-Vivo 10, 50% Human AB Serum, in aliquots of 1×107 cells/vial. The total number of vials produced from the cryopreservation for the MCB was 218.

Integration Site

DNA extract from haNK003 was provided to the CLIA/CAP certified NantOmics Sequencing Lab (Culver City, Calif.) for whole genome sequencing. Whole genome libraries were prepared for cell line samples using KAPA Hyper prep kit and sequenced on an Illumina HiSeq instrument to provide minimum coverage of 25×, completed for haNK003. DNA sequencing data was aligned to an augmented Genome Reference Consortium Human Build 37 (GRCh37, also known as hg19, originally obtained from the University of California, Santa Cruz Genome Browser—http://genome.ucsc.edu) containing the reported plasma sequence by bwa-mem, duplicate marked by samblaster, and indel realigned and base quality recalibrated by Genome Analysis Toolkit (GATK). Variant analysis was performed using the NantOmics Contraster analysis pipeline to determine variants, including single-nucleotide changes, small insertions or deletions (indels), copy-number changes, rearrangements, and integration sites. Integrated plasmid and resulting integration sites were visualized by the NantOmics Genome Browser and further comparison and visualization was done on the UCSC Genome Browser to identify any potential interactions with existing genomic elements.

haNK003 showed discordant read evidence of a mapping to chr17:15654977-15661403. The nearest 5' gene TBC1D26 (chr17:15,635,591-15,644,255) is 10,722 bp upstream, and the nearest 3' gene ADORA2B (chr17:15,848,231-15,871,210) is 186,828 bp downstream. Very little is known about TBC1D26, beyond being annotated as a GTPase-activating protein for Rab family protein(s) in UniProt. ADORA2B is annotated as a membrane protein that stimulates adenylate cyclase activity in the presence of adenosine (Strohmeier, et al., J. Biol. Chem. 270(5):2387-2394 (1995)). No coding variants were found in the two annotated ORFs for the coding sequence labeled pNEUKv1 FcRIL. UCSC Encode tracks and lincRNA shows evidence of a lincRNA transcript downstream of the insertion site (TCONS_12_00011108), however it is approximately 2,450 bp downstream of the 3' integration site, indicating this transcript is likely still intact. Investigation of a 100-way multiple alignment of vertebrate species indicates very little base-level conservation across the integration site, with negative log p-values ranging from −3.874 to 1.507 with a conservation mean of 0.01 and standard deviation of 0.58.

haNK003 contained no evidence of gene, transcript or regulatory breakage in the human genome integration site. Cell line haNK003's integration was at least 10 kbp away from any gene. The cell line is acceptable in that there is no evidence of disruption to any known genomic features in the target cell line human genomes.

Growth Characteristics

Figure 1B:
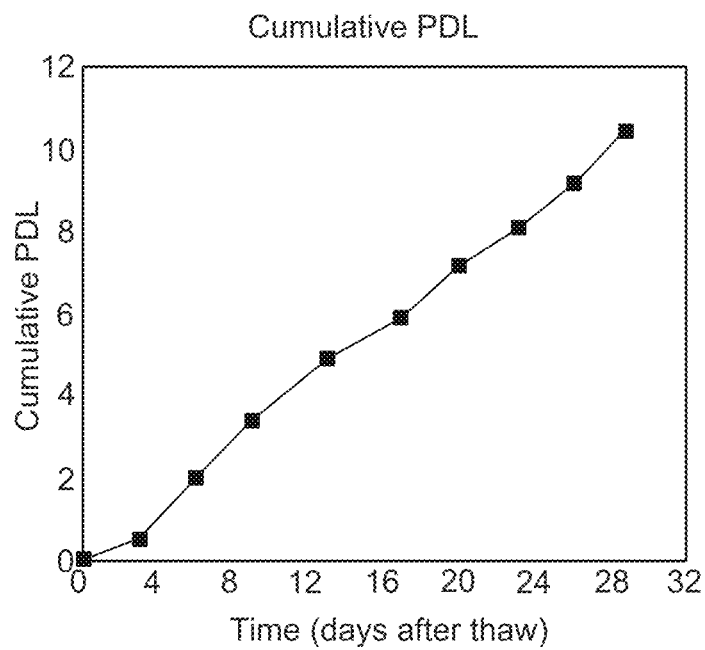
FIG. 1B is a graph showing population doubling level (PDL) of haNK003 cells. Viability (%), cell density (cells/mL), and cumulative PDL were monitored over the expansion period.

The growth characteristic of the clonal cell line haNK003 used to generate the MCB haNK003 is shown in FIGS. 1A and 1B. Data was analyzed from the cell culture history when growing cell line haNK003 for master cell bank cryopreservation. The mean doubling time was 65 (48-95) hours from day 3 to day 29. Comparable cell densities were achieved during passaging demonstrating that haNK003 cells grow consistently when passaged every 3 to 4 days and seeded at a density of approximately $0.3$-$0.5 \times 10^6$ cells/mL.

Phenotype

A study was conducted to quantify the expression of a panel of six protein markers on the surface of haNK003 cells and to compare the haNK003 profile to the profile of the parental cell line NK-92 (aNK). The panel of surface markers was selected to be representative of natural killer (NK) cells.

aNK cells express surface markers typical of an NK cell in an early differentiation stage, which express a number of activation receptors including NKG2D and NKp30 but lacking FcγRIIIa (CD16) and inhibitory KIRs (Killer Immunoglobulin like Receptors). This particular surface marker expression profile of aNK cells gives them their unique cytotoxic properties. Therefore, it was important to establish that the generation of the haNK003 cell line by stable transfection of a plasmid encoding the high-affinity FcγRIIIa and intracellularly retained IL-2 (ERIL-2) did not alter the expression profile of key surface markers of the parental aNK cell line. The surface markers CD54, CD56, NKG2D, NKp30, CD3, and CD16 were analyzed and the marker expression was determined by staining cells with specific fluorochrome-conjugated antibodies and detecting bound antibodies by flow cytometry.

Figure 2:
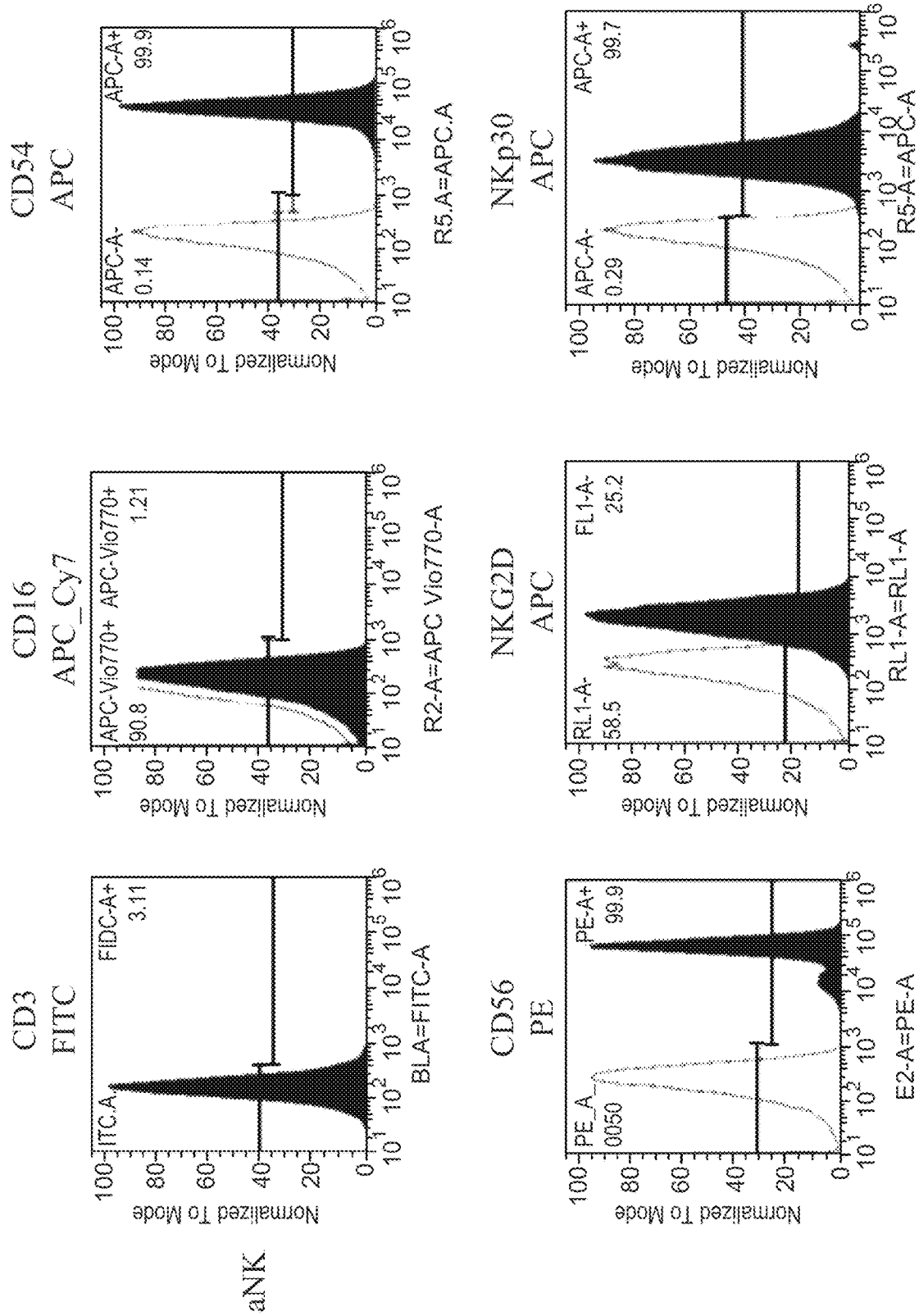
FIG. 2 shows representative histograms for the expression of surface markers in aNK and haNK003 cells.
Figure 2:
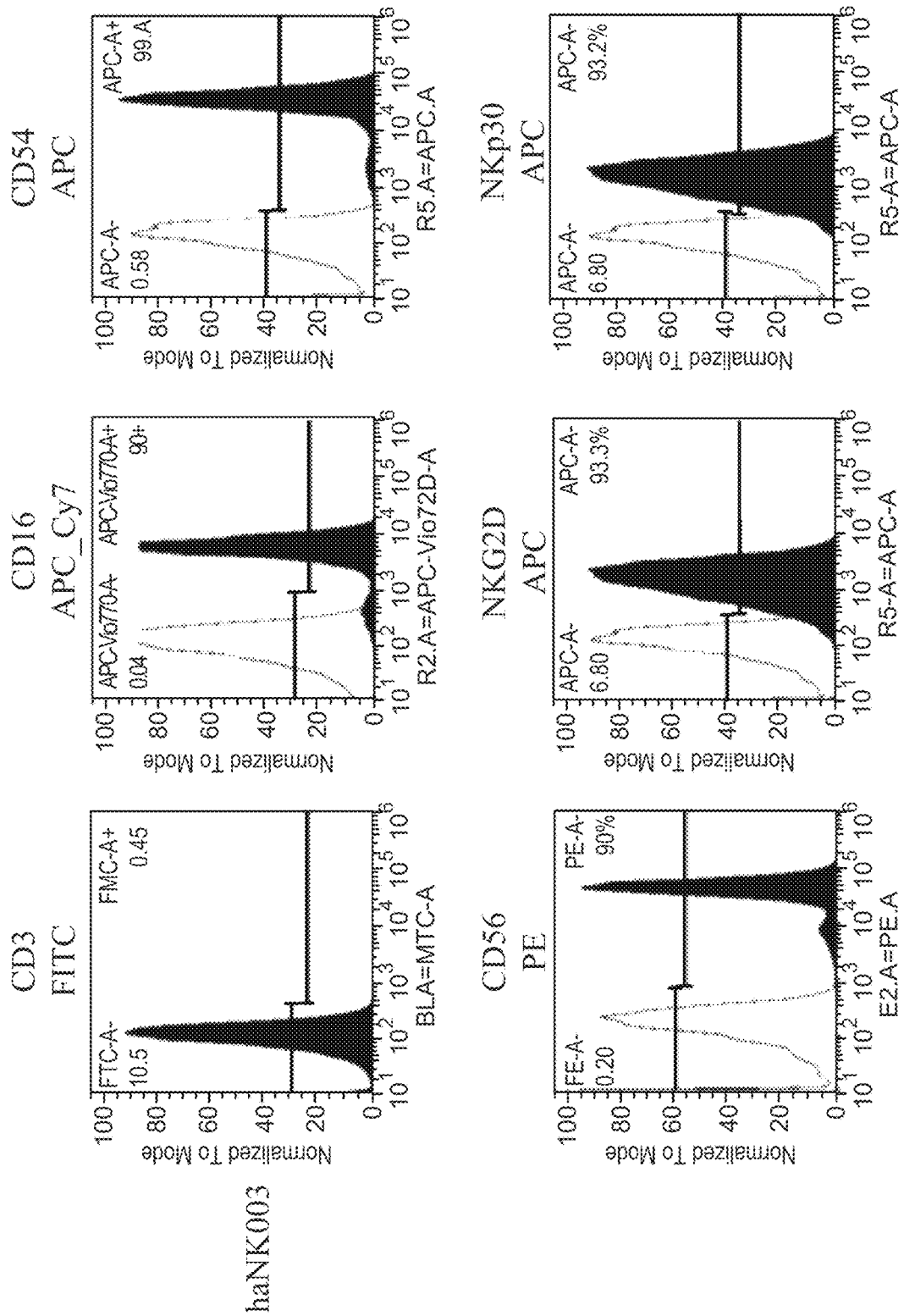
Figure 3A:
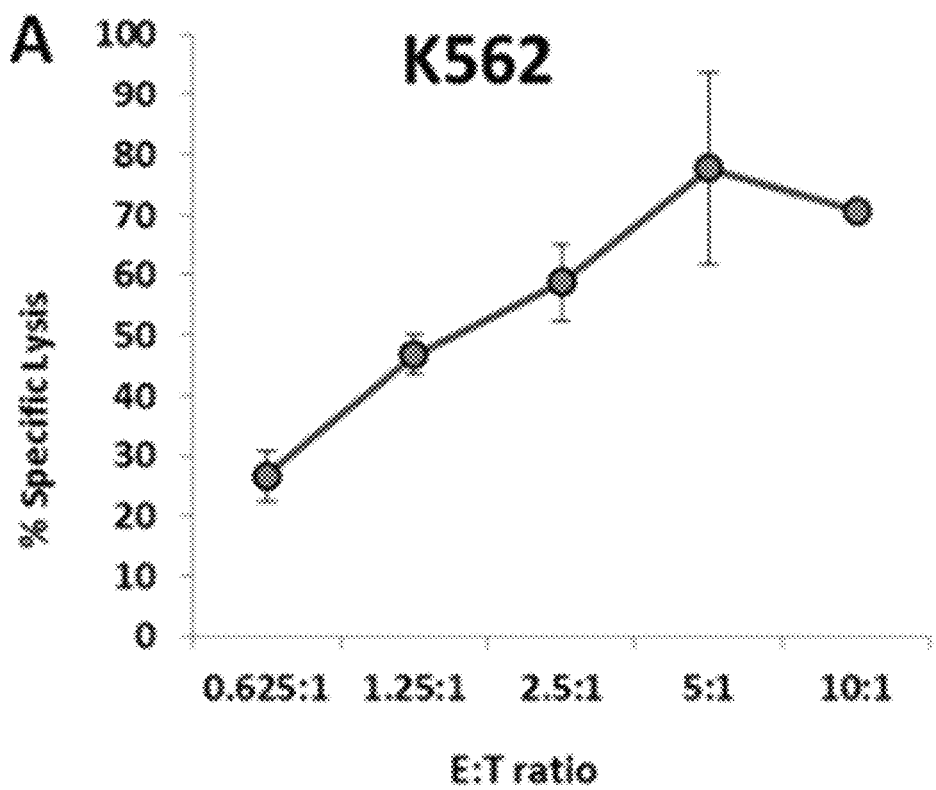
FIG. 3A is a graph showing natural cytotoxicity of haNK003 cells against K562 cells.
Figure 3B:
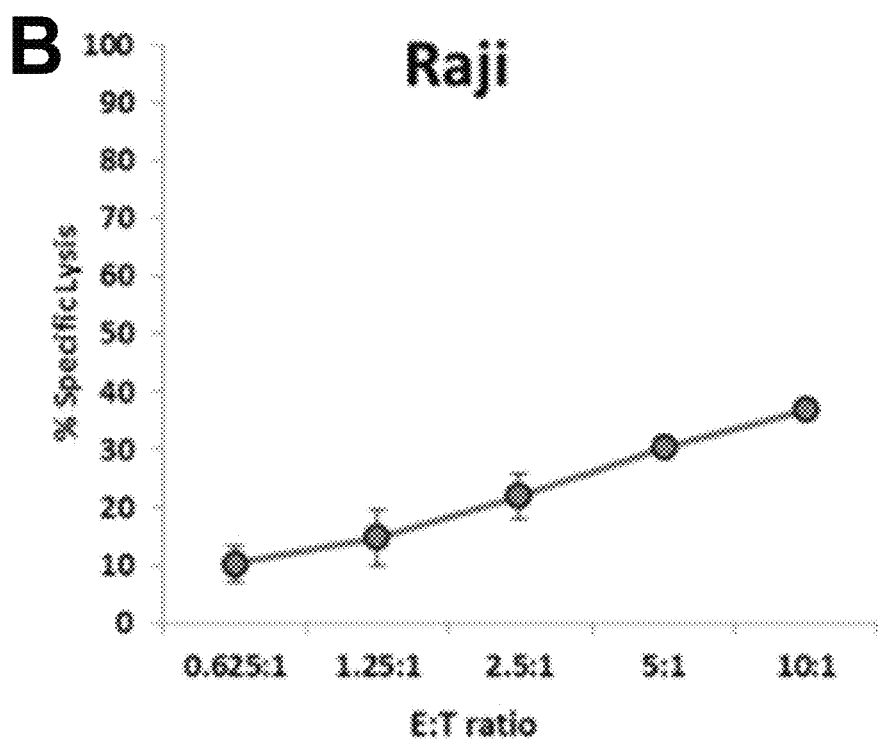
FIG. 3B is a graph showing natural cytotoxicity of haNK003 cells against Raji cells.
Figure 3C:
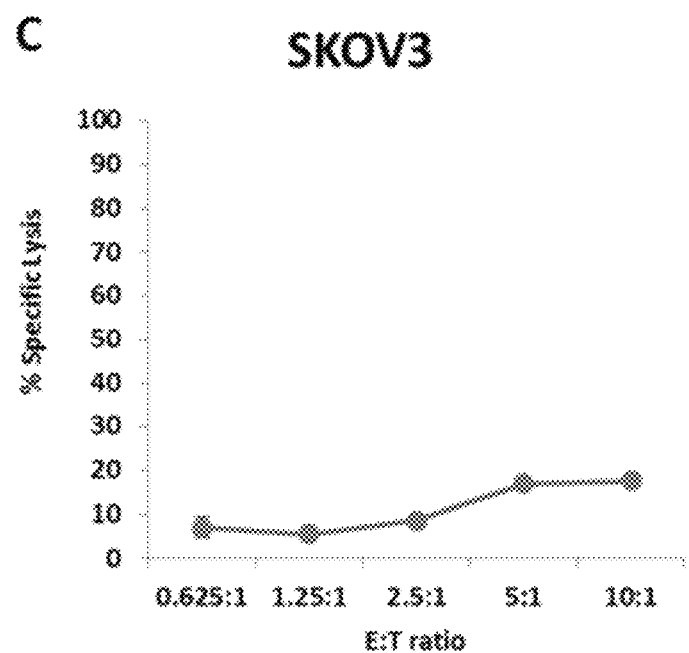
FIG. 3C is a graph showing natural cytotoxicity of haNK003 cells against SKOV3 cells.
Figure 3D:
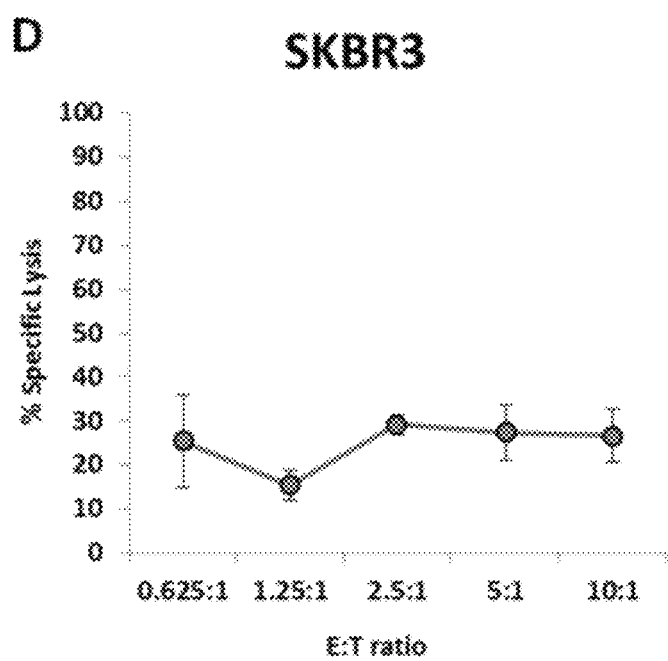
FIG. 3D is a graph showing natural cytotoxicity of haNK003 cells against SKBR3 cells.

The results of the flow cytometry analysis is summarized in Table 1 and representative histograms are provided in FIG. 2.

TABLE 1

Expression of surface markers.

|  |  | CD3 | CD16 | CD54 | CD56 | NKG2D | NKp30 |
|---|---|---|---|---|---|---|---|
| aNK | % | 0.62 ± 0.06 | 1.02 ± 0.64 | 99.01 ± 0.62 | 98.11 ± 2.00 | 82.88 ± 3.15 | 88.85 ± 7.77 |
| haNK003 | % | 0.02 ± 0.11 | 93.15 ± 4.00 | 96.42 ± 3.63 | 97.87 ± 2.60 | 81.95 ± 9.68 | 93.57 ± 2.06 |

% = percentage of cells positive for expression ± standard deviation haNK003 and aNK express comparable amounts of CD54, CD56, NKG2D and NKp30 as determined by median fluorescent intensity. In addition, the percentage of cells expressing these markers is equivalent. Neither haNK003 nor aNK express CD3 which is a T cell marker. As expected, haNK003 expresses the CD16 marker while aNK does not.

The generation of the haNK003 cell line has not altered the expression of key surface markers of the parental aNK cell line and has only added additional functionality in the form of the expression of CD16.

Cytotoxicity

Natural cytotoxicity of haNK003 cell line was evaluated against cell lines K562, Raji, SKOV3, and SKBR3 at various effector to target ratios (E:T). ADCC activity of haNK003 was also evaluated against cell lines Raji, SKOV3, and SKBR3 at various E:T ratios. The sensitivity of different target cell lines to haNK killing by natural cytotoxicity varies, with the K562 cell line being the most sensitive and the solid tumor cell lines (SKOV3 and SKBR3) being less sensitive (FIGS. 3A, 3B, 3C and 3D).

Figure 4A:
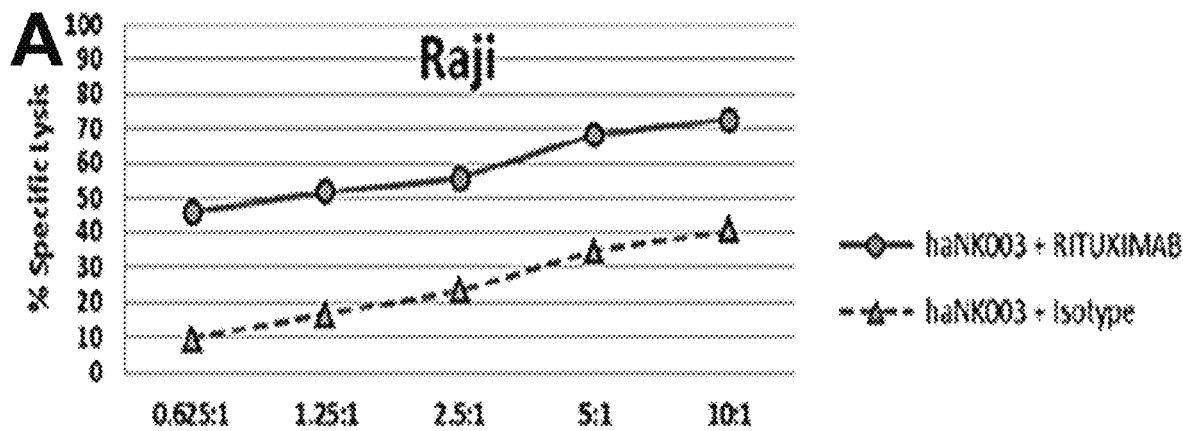
FIG. 4A is a graph showing ADCC of haNK003 cells against Raji cells.
Figure 4B:
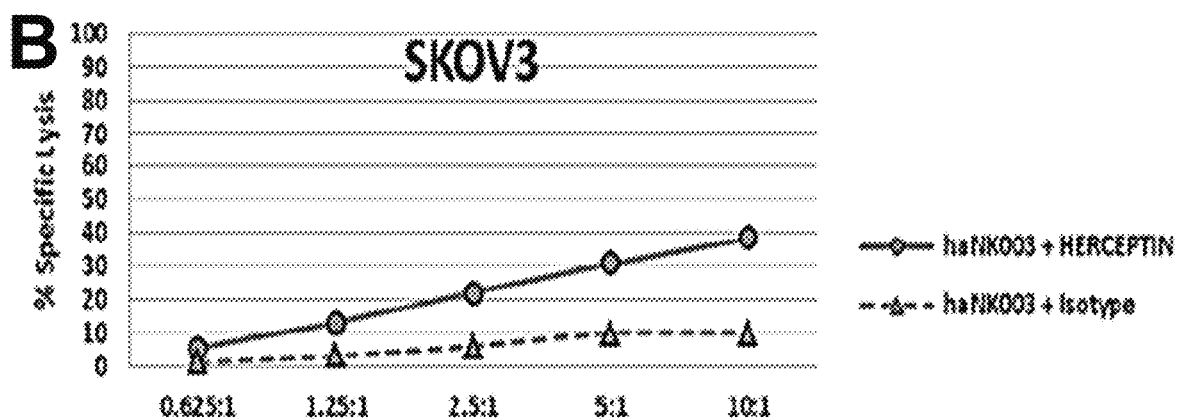
FIG. 4B is a graph showing ADCC of haNK003 cells against SKOV3 cells.
Figure 4C:
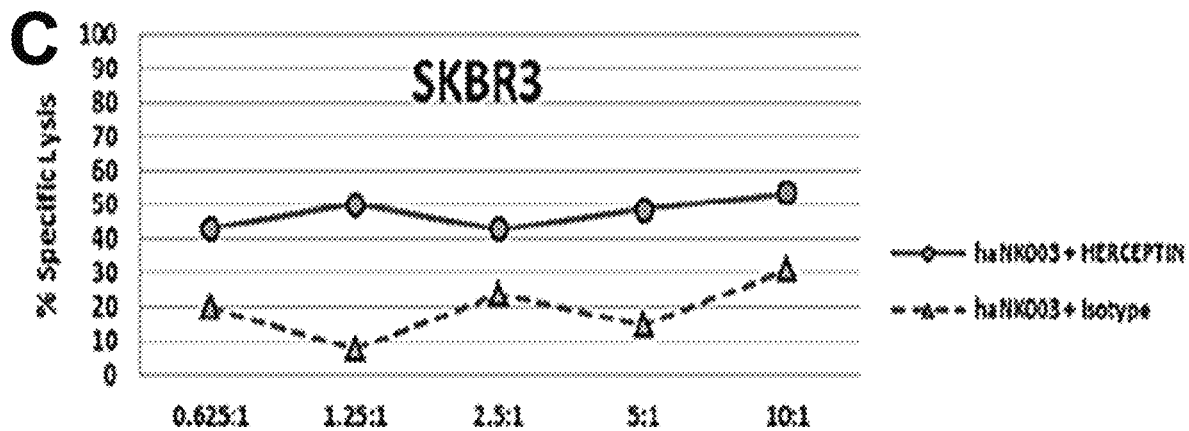
FIG. 4C is a graph showing ADCC of haNK003 cells against SKBR3 cells.

Some variation in haNK003 ADCC activity toward different target cell lines was also observed, with the highest specific lysis observed in Raji cells in combination with Rituximab (FIGS. 4A, 4B and 4C).

The results demonstrate that haNK003 cells exhibit natural cytotoxicity in the presence of several cancer cells, and are capable of enhanced specific lysis via ADCC with antibodies. The specifications and results for haNK™ MCB (haNK003) are provided in Table 2.

TABLE 2

Specifications of haNK003 cells.

| Test Description | Test Specification | haNK003 Results |
|---|---|---|
| Avg. Cell suspension volume/vial | ≥0.9 mL | 1.07 mL |
| Avg. Viability (post-bank thaw) | ≥85% | 89% |
| Avg. Viability (post-bank passaged) | ≥85% | 97% |
| Avg. Total Viable Cells/vial | Report result | $7.13 \times 10^6$ |
| Natural Killer (NK) cell assay & tumor target cell - ADCC assay with Herceptin and Rituxan | Report result - target greater than 50% at 20:1 E:T ratio | 5:1 E:T Ratio with Herceptin (3.3 µg/mL) vs SKOV3 71.1%; 1:1 E:T Ratio with Rituxan (3.3 µg/mL) vs DOHH2 52.8% |
| Identity by Fluorescent Monoclonal Antibody Staining for Surface Antigens | ≥90% CD56+ | 98.0% |
|  | ≥90% CD16+ | 92.7% |
|  | ≤5% CD3+ | 0.02% |
| CO1 Barcode Assay for Cell Line Identification | Cell line is of human Origin | Pass |
| Isolator Sterility Testing Using a Direct Inoculation Method | No bacterial or fungal Growth | Pass |
| Test for Presence of Agar-Cultivable and Non-agar Cultivable Mycoplasma | No mycoplasma Detected | Pass |
| In Vitro Assay for the Presence of Bovine Viruses According to 9 CFR Requirements | Negative for the presence of viral contaminants | Performed on aNK MCB (haNK003 starting material) Negative |
| 28-day In Vitro Assay for the Presence of Viral Contaminants | Negative for the presence of viral contaminants | Pass |
| Test for the Presence of Inapparent Viruses | Negative for the presence of adventitious viral contaminants | Pass |
| Transmission Electron Microscopic Examination of Cell Cultures (200 Cell profiles) | Report Result | No extraneous agents observed in the 200 cell profiles examined |
| Quantitative Product Enhanced Reverse Transcriptase (Q-PERT) Assay for the Detection of Retrovirus in Biological Samples | Report Result | The concentration of RT units in the sample is $<5.00 \times 10_{-7}$ units/mL |

TABLE 2-continued

Specifications of haNK003 cells.

| Test Description | Test Specification | haNK003 Results |
|---|---|---|
| Detection of 14 Viruses by Real Time Polymerase Chain Reaction Assays (Human Panel I) | Report Result | All virus negative except EBV$_a$ (detection limit = 10 copies) |
| Assessment of Production of Infectious Epstein Barr Virus (EBV) by NK-92 Cells | Does not actively produce EBV | Performed on aNK MCB (haNK003 starting material) NK-92 cells do not pose a risk for EBV infection[a] |

[a]Although EBV virus genome is detected, tests with NK-92 (aNK) determined that cells do not cause infection of EBV. Infectivity studies were conducted by co-culturing aNK cells (irradiated and non-irradiated) with B-lymphocytes to determine if the aNK cells release viral particles capable of infecting normal cells. Results showed no indication of proliferation or outgrowth of B-lymphocytes, indicating that aNK cells do not pose a risk for EBV infection.

Example 2. Effect of Irradiation on In Vitro Proliferative Capacity and Functionality haNK™ cells are irradiated to mitigate the risk of uninhibited proliferation. The effects of irradiation on in vitro proliferative capacity and functionality were evaluated. These studies demonstrate that irradiation at 10 Gy inhibits the proliferative capacity of at least 99.9% of haNK cells while still maintaining functional activity for at least 6 hours post-irradiation.

haNK003 cells exhibit both natural (direct) cytotoxicity and antibody-dependent cell-mediated cytotoxicity (ADCC). In both cases, target cell antigens are recognized by activating receptors on NK cells. For natural cytotoxicity, these target cell antigens are stress antigens characteristic of virally infected or transformed cells. For ADCC, the antigens are tumor specific antigens that are recognized by an antibody, which in turn binds to the NK cell activating receptor, FcγRIIIa (CD16), through its constant (Fc) region.

The interaction of the NK cell with target cell ligands (either through direct interaction or through an antibody-mediated interaction) results in the formation of a cellular junction and subsequent release of perforins and granzymes. This in turn induces an apoptotic process within the target cell leading to disintegration of the cell membrane and target cell death.

A study was conducted to determine the level of natural cytotoxicity and ADCC activity and the duration of that activity following gamma irradiation at 10 Gy on pre-formulated cells. For this study, 1.5×10$^7$ cells per flask were irradiated. Although the number of cells subjected to irradiation was not equivalent to that which will be used in manufacture of a clinical dose, assay of the functionality following irradiation will provide insight for manufacturing capabilities.

For the purposes of these experiments, haNK003 cells were irradiated at 10 Gy using an X-ray irradiator. Non-irradiated cells were subjected to the same manipulations without irradiation. Target cells were selected to represent sensitivities to different mechanisms of killing by NK cells. For example, K562 cells are highly sensitive to killing by natural cytotoxicity while DOHH is partially sensitive to killing through natural cytotoxicity, but sensitive to ADCC with the appropriate antibodies. Irradiated and non-irradiated cells were assayed side-by-side for specific cytotoxicity using a flow cytometry based assay that was developed in-house. Target cells were labeled with a green fluorescent dye with long aliphatic tails (PKH67) to stably incorporate the dye into lipid regions of the cell membrane. Cell lysis was monitored by propidium iodide staining.

Figure 5:
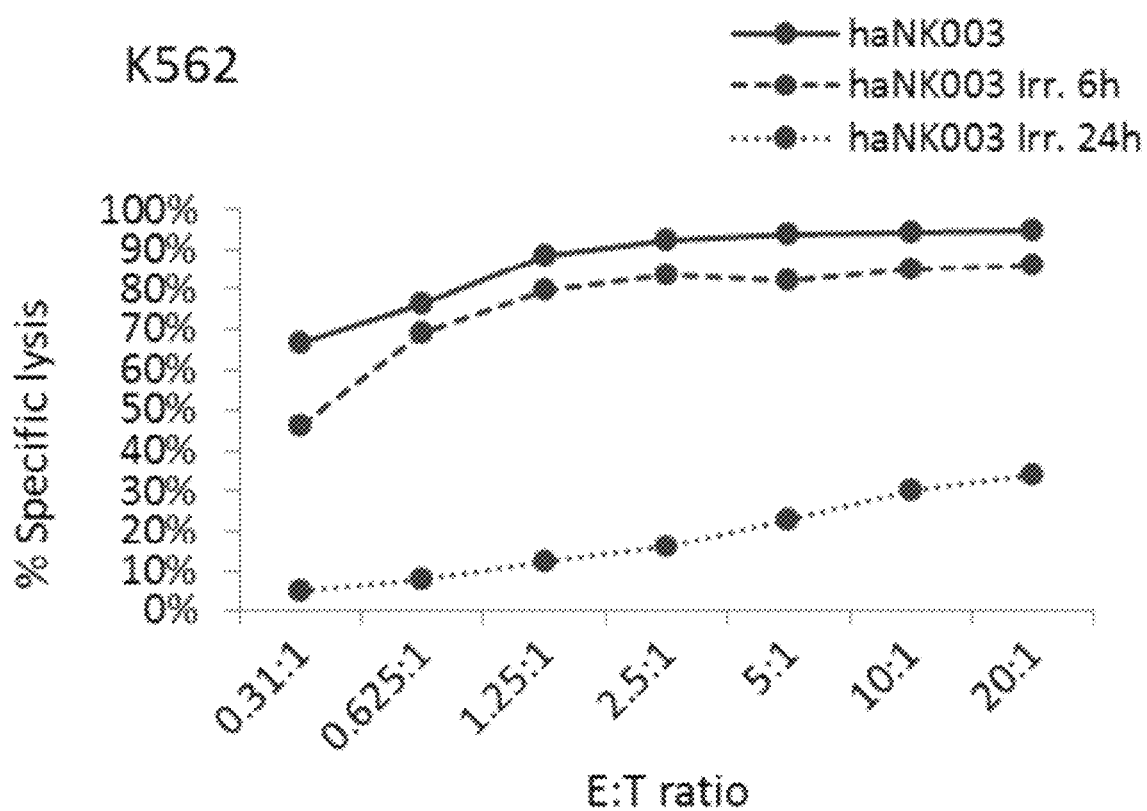
FIG. 5 is a graph showing natural cytotoxic activity of irradiated vs. non-irradiated haNK003 cells against K562 cells. haNK003 cells were mock-irradiated (solid line) or irradiated at 10 Gy. Cytotoxic activity of irradiated haNK003 against K562 cells was assayed at 6 hr (dashed line) or 24 hr (dotted line) post-irradiation.
Figure 6:
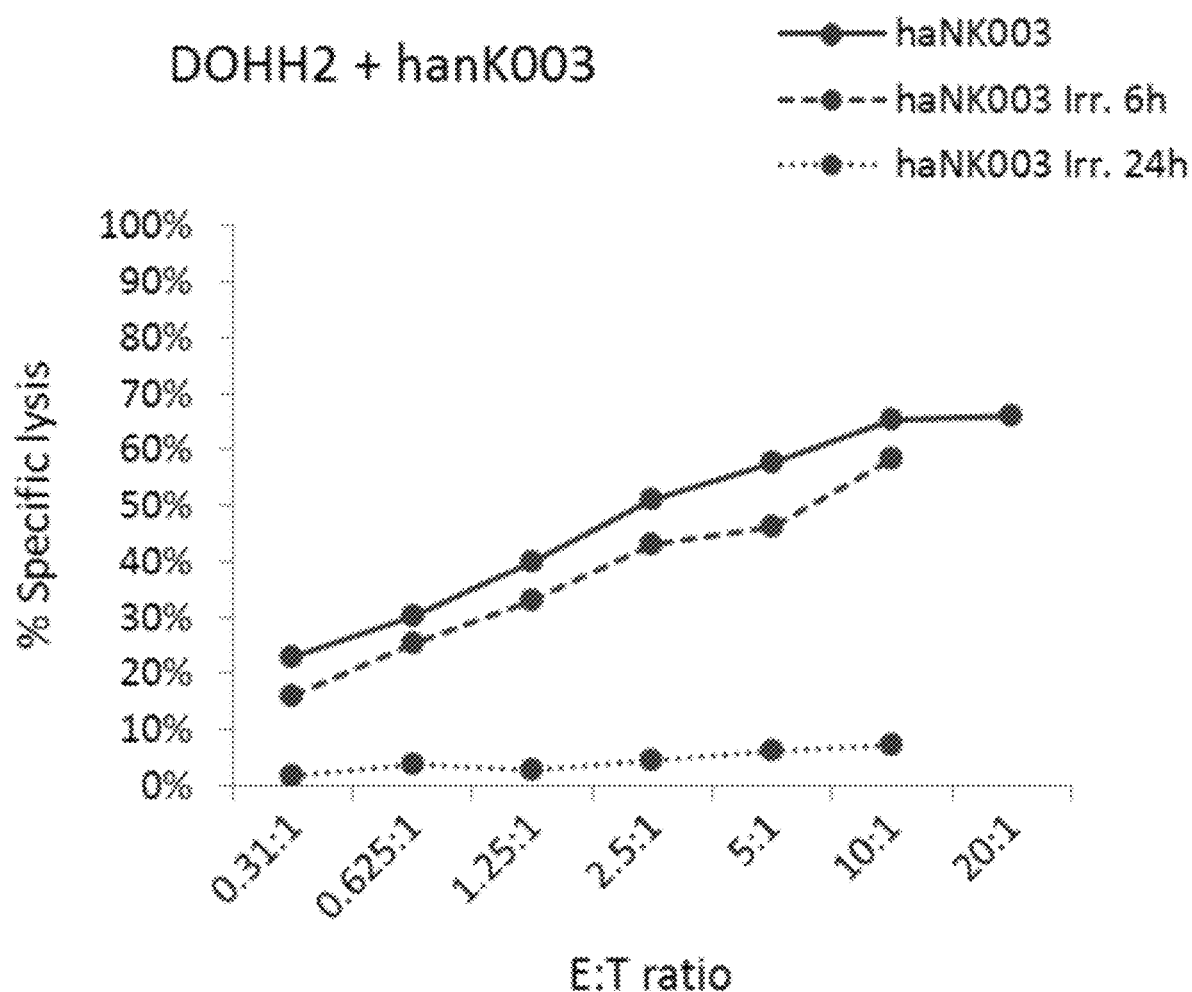
FIG. 6 is a graph showing natural cytotoxic activity of irradiated vs. non-irradiated haNK003 cells against DOHH2 cells. haNK003 cells were mock-irradiated (solid line) or irradiated at 10 Gy. Cytotoxic activity of irradiated haNK003 against DOHH2 cells was assayed at 6 hr (dashed line) or 24 hr (dotted line) post-irradiation. Note that data points for E:T ratios of 20:1 were not obtained for irradiated cells because cell death resulted in insufficient numbers of haNK003 cells.

Analysis of natural cytotoxic activity demonstrates that the impact of irradiation varies with the target cell and time post-irradiation. For sensitive cells such as K562, natural cytotoxic activity was maintained within 6 hours of irradiation but was reduced by 40% or more after 24 hours across all effector to target ratios (E:T) (FIG. 5). For DOHH2, natural cytotoxic activity was also retained at 6 hours post-irradiation but was reduced by 14% or more after 24 hours across all effector to target ratios and reduced by as much as 50% at a E:T ratio of 10:1 (FIG. 6).

Figure 7:
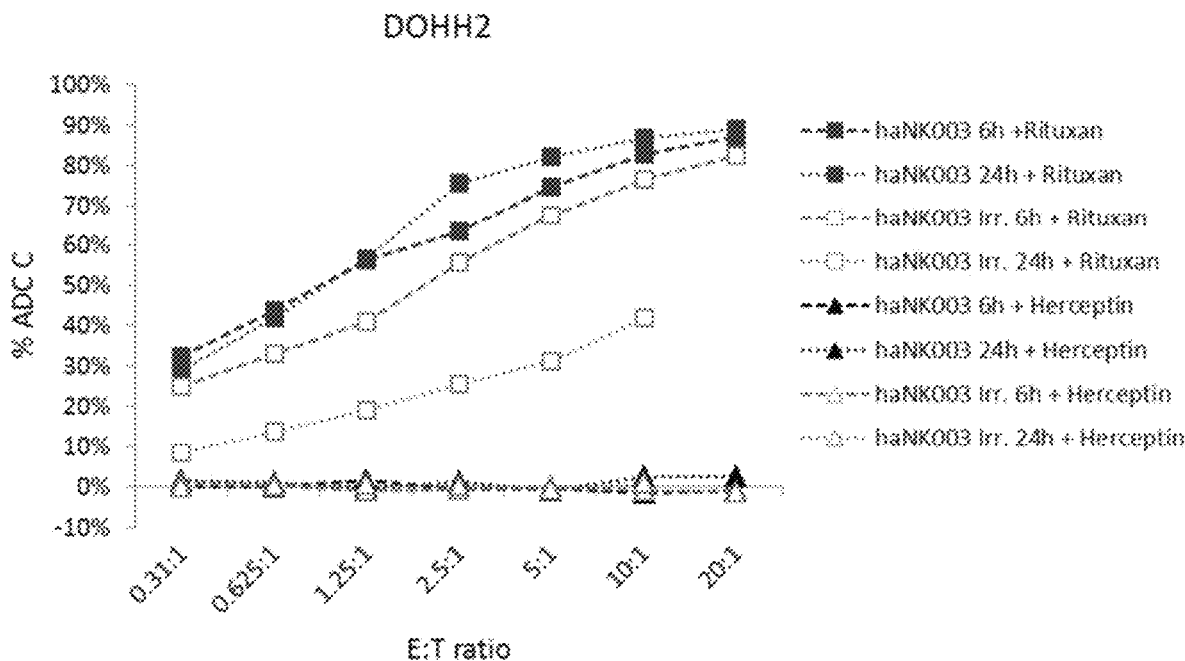
FIG. 7 is a graph showing ADCC activity of irradiated vs. non-irradiated haNK003 cells against DOHH2 cells. haNK003 cells were mock irradiated (solid symbols) or irradiated at 10 Gy (hollow symbols). ADCC activity of irradiated and non-irradiated haNK003 against DOHH2 cells was assayed at 6 hr (dashed lines) or 24 hr (dotted lines) post-irradiation, in combination with Rituxan (squares) or with Herceptin (triangles), which does not react with DOHH2 cells. Note that the data point for E:T ratio of 20:1 was not obtained for irradiated cells at the 24 hour time point because cell death resulted in insufficient numbers of haNK003 cells.
Figure 8A:
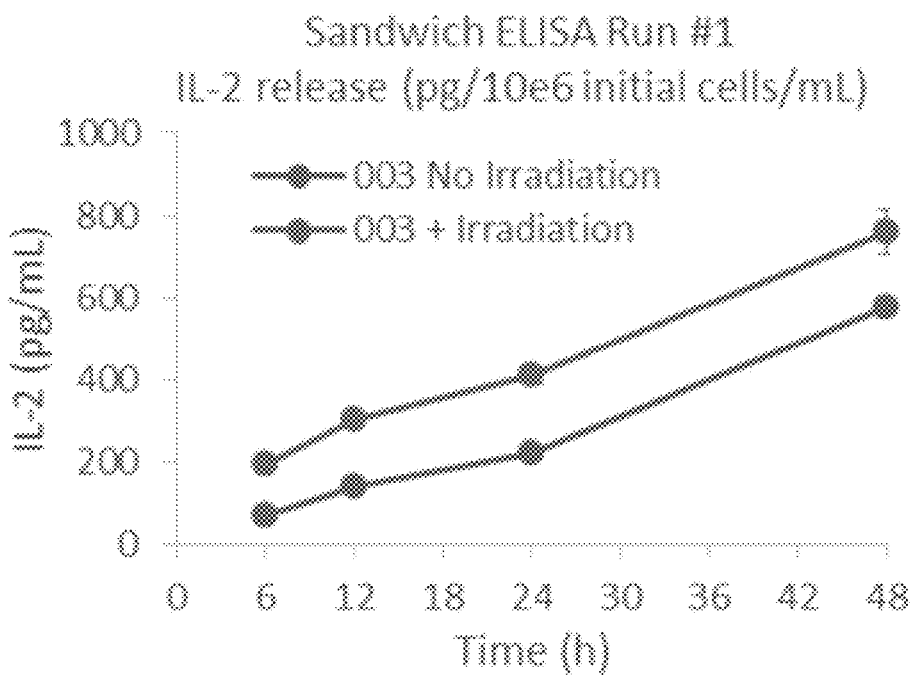
FIG. 8A is a graph showing IL-2 released (pg/mL) per $1 \times 10^6$ cells of irradiated vs. non-irradiated cells at 6, 12, 24 and 48 hours (h) as determined by sandwich ELISA run #1.
Figure 8B:
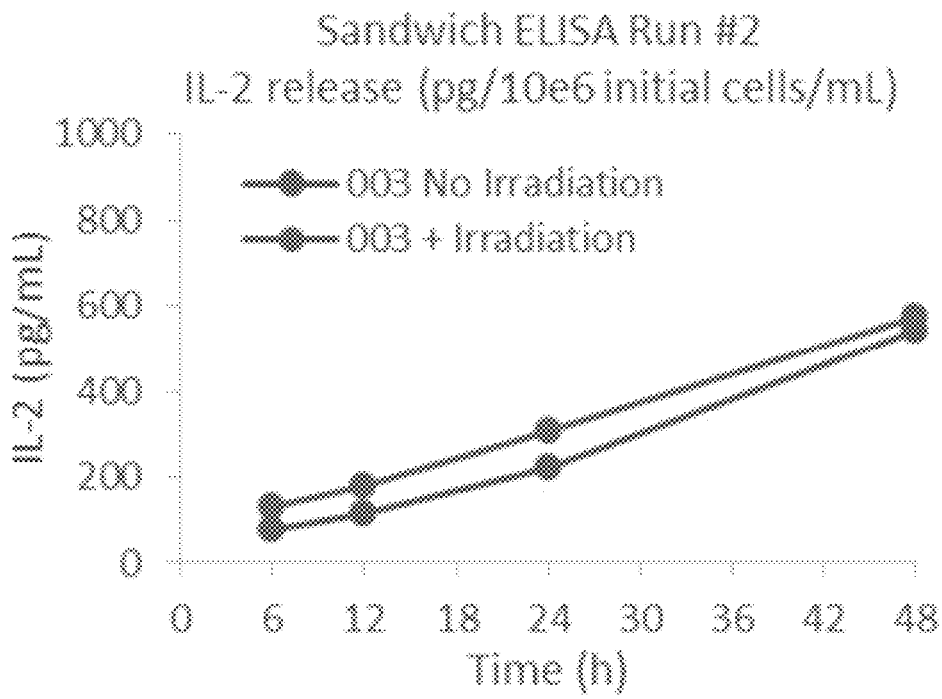
FIG. 8B is a graph showing IL-2 released (pg/mL) per $1 \times 10^6$ cells of irradiated vs. non-irradiated cells at 6, 12, 24 and 48 hours (h) as determined by sandwich ELISA run #2.
Figure 8C:
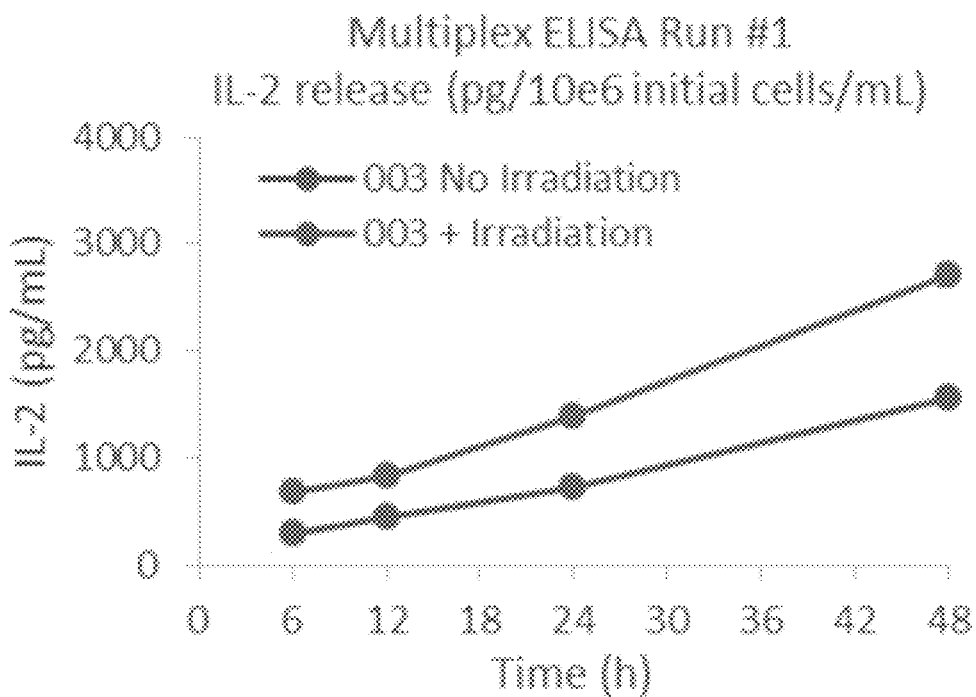
FIG. 8C is a graph showing IL-2 released (pg/mL) per $1 \times 10^6$ cells of irradiated vs. non-irradiated cells at 6, 12, 24 and 48 hours (h) as determined by multiplex ELISA run #1.
Figure 8D:
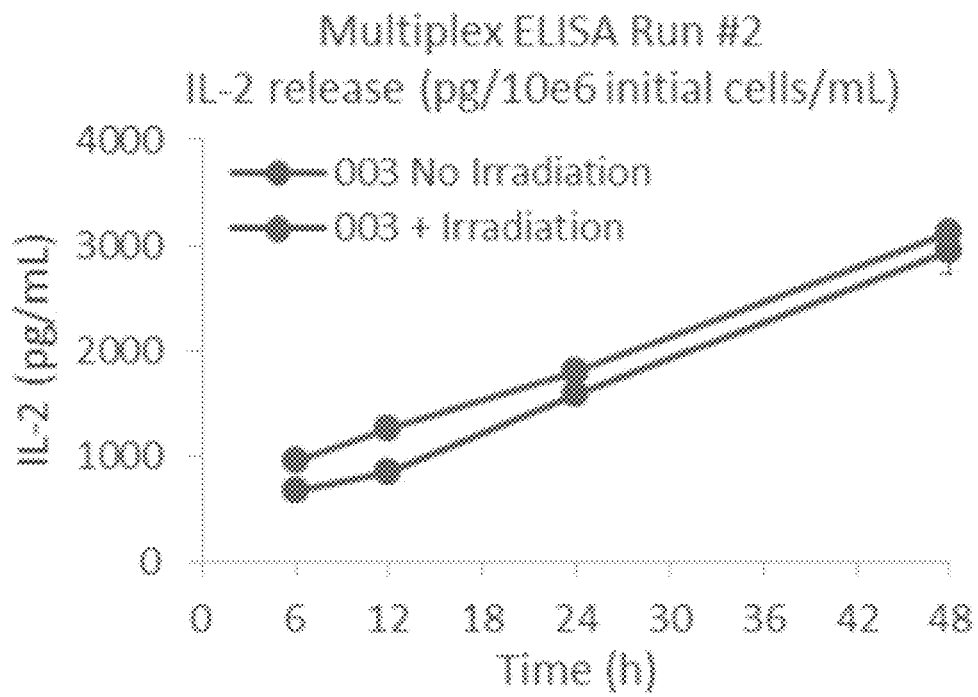
FIG. 8D is a graph showing IL-2 released (pg/mL) per $1 \times 10^6$ cells of irradiated vs. non-irradiated cells at 6, 12, 24 and 48 hours (h) as determined by multiplex ELISA run #2.
Figure 9A:
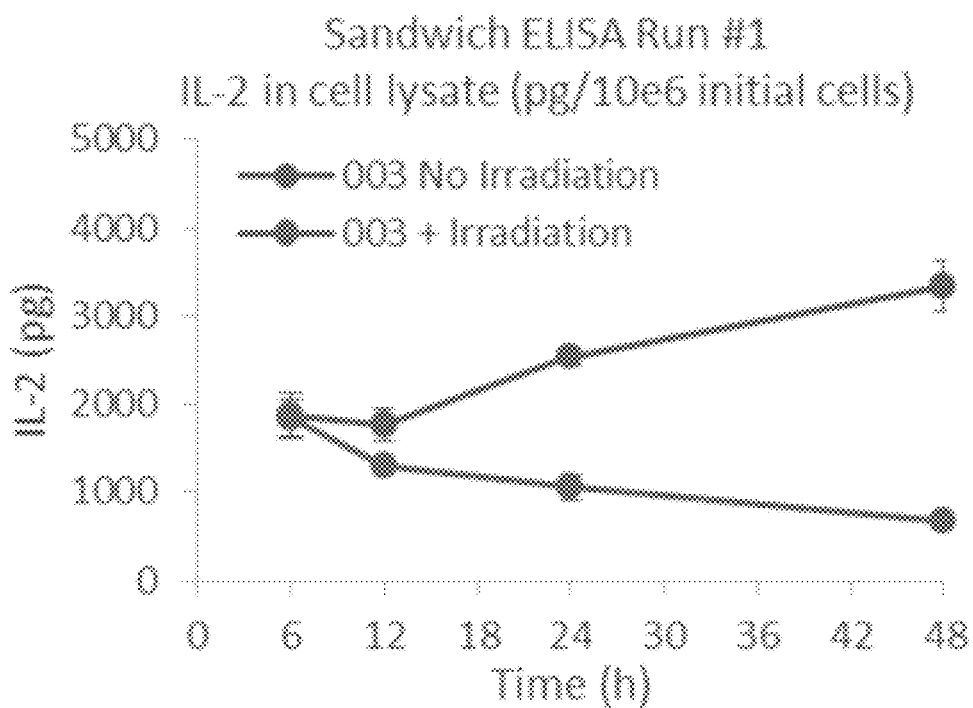
FIG. 9A is a graph showing total intracellular IL-2 content (pg) per $1 \times 10^6$ cells of irradiated vs. non-irradiated cells at 6, 12, 24 and 48 hours (h) as determined by sandwich ELISA run #1.
Figure 9B:
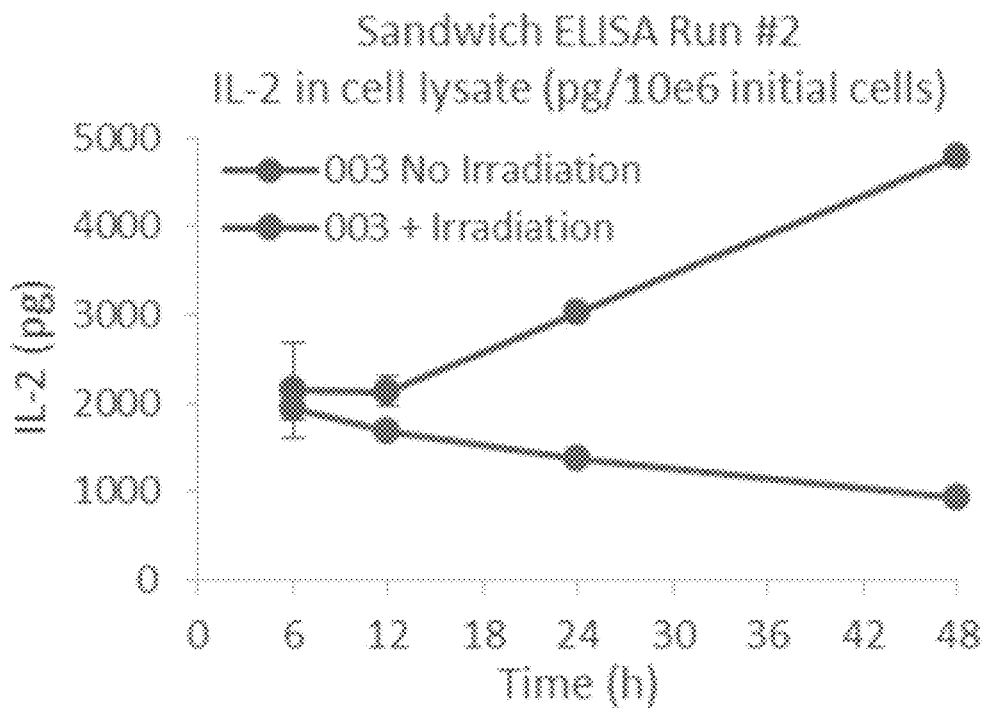
FIG. 9B is a graph showing total intracellular IL-2 content (pg) per $1 \times 10^6$ cells of irradiated vs. non-irradiated cells at 6, 12, 24 and 48 hours (h) as determined by sandwich ELISA run #2.
Figure 9C:
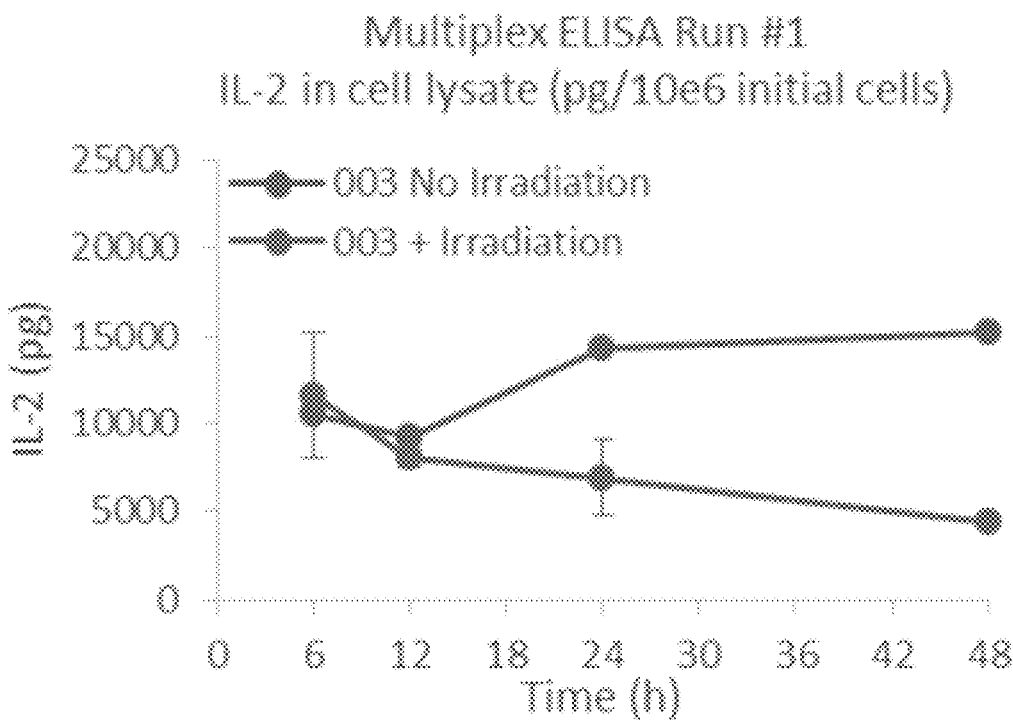
FIG. 9C is a graph showing total intracellular IL-2 content (pg) per $1 \times 10^6$ cells of irradiated vs. non-irradiated cells at 6, 12, 24 and 48 hours (h) as determined by multiplex ELISA run #1.
Figure 9D:
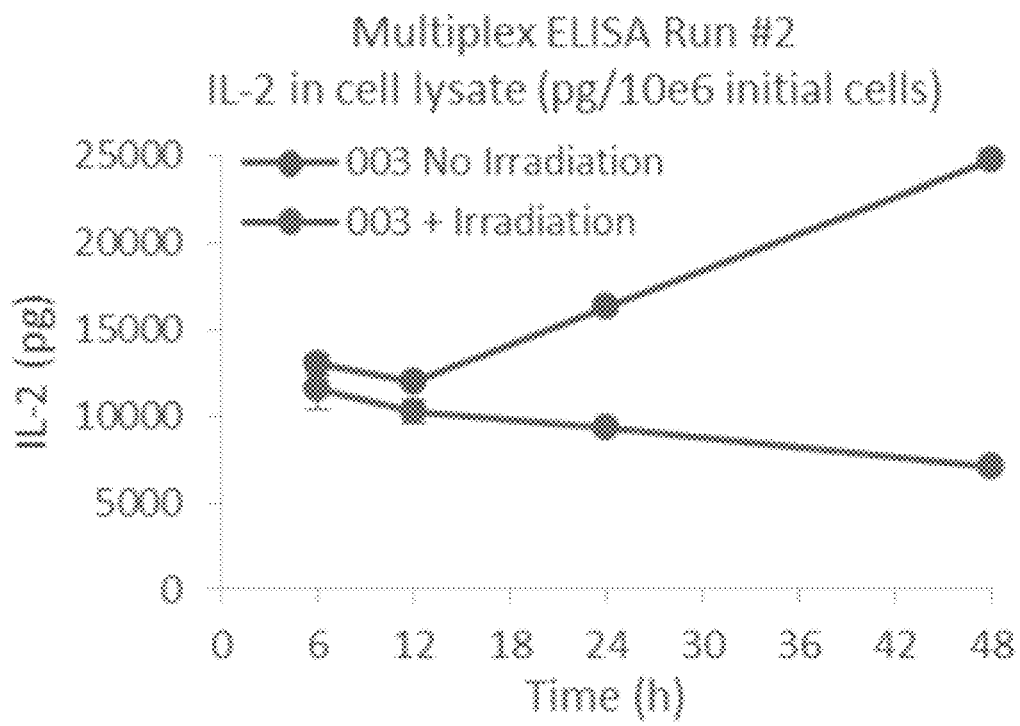
FIG. 9D is a graph showing total intracellular IL-2 content (pg) per $1 \times 10^6$ cells of irradiated vs. non-irradiated cells at 6, 12, 24 and 48 hours (h) as determined by multiplex ELISA run #2.

The level of rituximab-mediated ADCC activity with DOHH2 targets was also maintained by irradiated cells at 6 hours. However, rituximab-mediated ADCC activity for irradiated cells at 24 hours was reduced by about 16% or more from the activity seen with cells at 6 hours, and non-irradiated cells at 24 hours (FIG. 7). As expected, Herceptin (trastuzumab) did not induce any ADCC killing of DOHH2 target cells in combination with haNK003 (FIG. 4), nor did the antibodies alone (rituximab or trastuzumab) induce any DOHH2 target cell killing (data not shown).

Relevant levels of cytotoxic activity and ADCC activity are maintained for at least 6 hours after irradiation of pre-formulated haNK003 cells.

Example 3. Characterization of IL-2 Release

A study was conducted to analyze the amount of IL-2 released by haNK003 cells into the culture medium as well as the amount of intracellular-retained IL-2 in haNK003 cells at various time points. Amounts of IL-2 were measured in supernatants to determine IL-2 release by haNK003. Amounts of IL-2 were measured in cell pellet lysates to determine the total levels of intracellular IL-2 in haNK003. Samples were analyzed pre- and post-irradiation to determine the impact of irradiation on IL-2 release and intracellular IL-2 levels.

Two separate assays were performed (Run #1 and Run #2) where haNK003 cells were cultured in T-75 flasks and irradiated at 0 Gy (no irradiation) or 10 Gy (irradiation) using an X-ray irradiator. haNK003 cells (non-irradiated and irradiated) were then cultured in X-Vivo 10 with 5% heat-inactivated Human AB Serum for up to 48 hours. Samples from culture supernatants as well as cell pellets were collected for analysis at various time points. Cell pellets were lysed using a detergent-based solution to quantify total intracellular IL-2. The IL-2 concentration in culture supernatant and in cell lysate samples was measured independently at NantKwest or by AllCells, LLC using two different detection methods (sandwich ELISA or multiplex ELISA).

The IL-2 concentration values measured by the two different methods differ by a factor of five on average for the same samples. Both methods show a linear increase of IL-2 release over time for both irradiated and non-irradiated cells (Table 3 and FIGS. 8A, 8B, 8C, and 8D). IL-2 concentration in the culture supernatants of irradiated cells tends to be higher than non-irradiated cells at all time points, although the difference varied between assay runs #1 and #2.

TABLE 3

IL-2 Released (pg/mL) per 1 × 10⁶ Cells of Irradiated vs. Non-irradiated haNK003 at Different Time Points (average and standard deviation [StDev] for duplicate reads)

| | | Sandwich ELISA | | | | Multiplex ELISA | | | |
|---|---|---|---|---|---|---|---|---|---|
| | | Run#1 | | Run#2 | | Run#1 | | Run#2 | |
| Il-2 (pg/mL) | Time | Average | StDev | Average | StDev | Average | StDev | Average | StDev |
| No Irradiation | 6 h | 68.59 | 5.52 | 78.62 | 6.00 | 290.06 | 11.89 | 666.99 | 51.20 |
| | 12 h | 139.67 | 9.93 | 117.29 | 1.92 | 458.38 | 4.48 | 851.74 | 18.34 |
| | 24 h | 217.73 | 6.68 | 222.64 | 9.05 | 734.75 | 24.11 | 1578.50 | 8.80 |
| | 48 h | 575.66 | 28.84 | 544.32 | 9.88 | 1548.19 | 33.72 | 2944.94 | 207.54 |
| Irradiation 10 Gy | 6 h | 194.67 | 11.21 | 129.44 | 0.62 | 689.11 | 12.69 | 961.78 | 3.70 |
| | 12 h | 299.49 | 5.42 | 181.14 | 2.38 | 828.70 | 70.00 | 1254.33 | 8.17 |
| | 24 h | 407.17 | 20.92 | 305.67 | 13.46 | 1277.78 | 44.17 | 1804.96 | 59.97 |
| | 48 h | 760.03 | 52.77 | 575.04 | 8.03 | 2706.81 | 110.53 | 3116.85 | 67.10 | h—hours

The total intracellular IL-2 concentration values measured by the two different methods differ by a factor of five on average for the same samples (Table 4 and FIGS. 9A, 9B, 9C and 9D). Both methods show an increase of total intracellular IL-2 in non-irradiated cell lysates over time while the amount of total intracellular IL-2 in irradiated cell lysates decreases over time. At 6 hours in culture, levels of total intracellular IL-2 were comparable between irradiated and non-irradiated cells as measured by both methods. In irradiated cells, these levels decrease after 48 hours in culture.

TABLE 4

Total Intracellular IL-2 Content (pg) per 1 × 10⁶ Cells of Irradiated vs. Non-irradiated haNK003 at Different Time Points (average and standard deviation [StDev] for duplicate reads)

| | | Sandwich ELISA | | | | Multiplex ELISA | | | |
|---|---|---|---|---|---|---|---|---|---|
| | | Run#1 | | Run#2 | | Run#1 | | Run#2 | |
| Il-2 (pg) | Time | Average | StDev | Average | StDev | Average | StDev | Average | StDev |
| No Irradiation | 6 h | 1874.67 | 257.77 | 2147.01 | 545.61 | 10579.41 | 256.64 | 12918.29 | 617.75 |
| | 12 h | 1754.12 | 181.89 | 2129.07 | 161.22 | 9255.57 | 377.00 | 11974.20 | 179.42 |
| | 24 h | 2550.76 | 101.92 | 3014.07 | 16.52 | 14267.76 | 5.22 | 16275.56 | 321.19 |
| | 48 h | 3350.60 | 277.37 | 4788.39 | 50.06 | 15273.12 | 356.81 | 24701.64 | 103.56 |
| Irradiation 10 Gy | 6 h | 1851.47 | 208.93 | 1932.82 | 130.67 | 11614.02 | 3653.73 | 11588.93 | 1244.94 |
| | 12 h | 1297.41 | 56.05 | 1678.55 | 41.01 | 8007.80 | 429.63 | 10186.55 | 697.17 |
| | 24 h | 1053.23 | 140.84 | 1374.36 | 48.56 | 6902.43 | 2143.72 | 9241.67 | 75.20 |
| | 48 h | 666.46 | 54.55 | 930.67 | 44.93 | 4394.21 | 223.74 | 6985.23 | 36.66 | h—hours

Figure 10A:
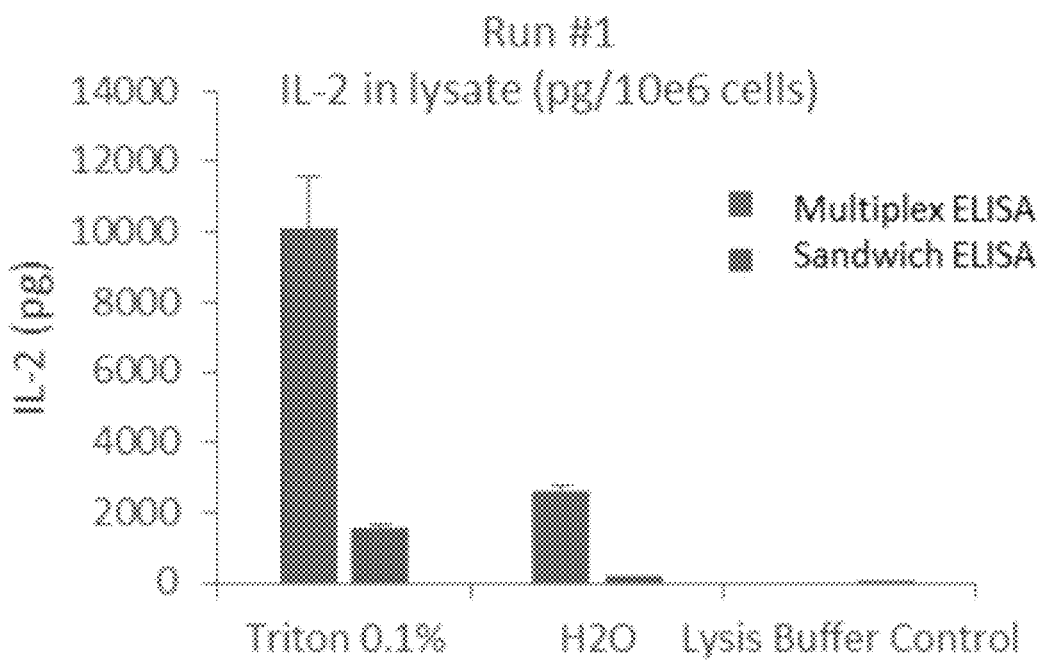
FIG. 10A is a graph showing the amount of solubilized IL-2 (pg) per $1 \times 10^6$ cells in run #1 as determined by multiplex and sandwich ELISA.
Figure 10B:
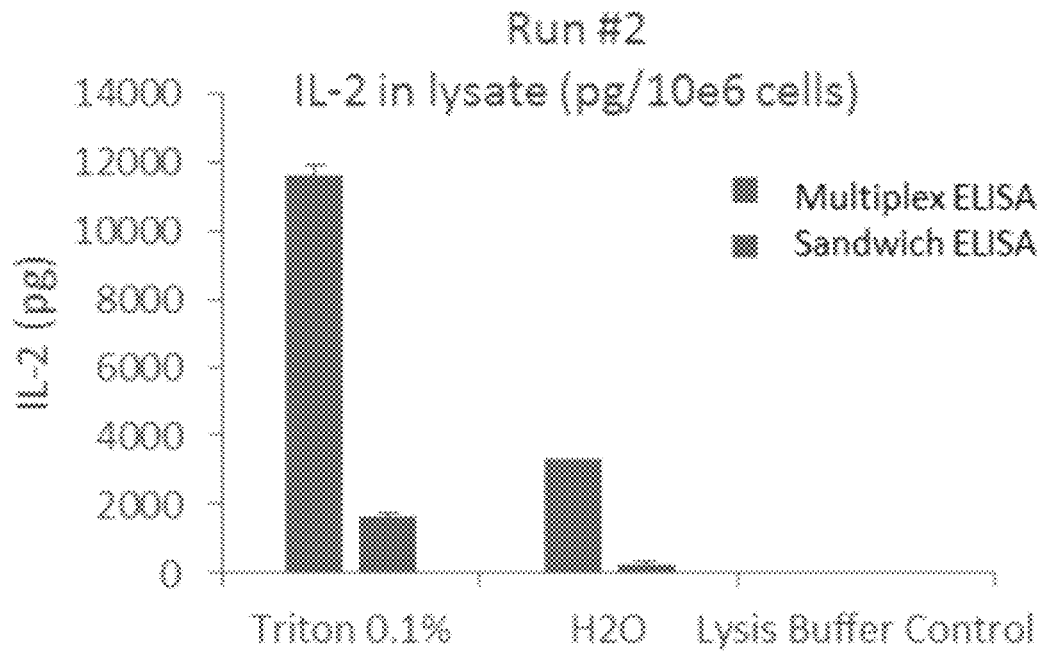
FIG. 10B is a graph showing the amount of solubilized IL-2 (pg) per $1 \times 10^6$ cells in run #2 as determined by multiplex and sandwich ELISA.

To simulate the release of IL-2 upon cell necrosis, cells were subjected to hypotonic shock. This level was compared to the total intracellular IL-2 concentration measured in cell lysates prepared using a detergent-based method. The solubilized IL-2 concentration values measured by the two methods (sandwich or multiplex ELISA) differ by a factor ~10 for the same samples (Table 5 and FIGS. 10A and 10B). IL-2 concentration in lysates from hypotonic shock was between 181.93-289.54 pg/106 cells (sandwich ELISA) and 2619.15-3301.02 pg/106 cells (multiplex ELISA), which represents on average between 14% (sandwich ELISA) and 27% (multiplex ELISA) of the total intracellular IL-2 concentration measured in cell lysates prepared using a detergent-based lysis.

TABLE 5

Amount of Solubilized IL-2 (pg) per $1 \times 10_6$ Cells of haNK003 Cells (average and standard deviation [StDev] for duplicate reads).

|  |  | Sandwich ELISA | | | | Multiplex ELISA | | | |
|---|---|---|---|---|---|---|---|---|---|
|  |  | Run#1 | | Run#2 | | Run#1 | | Run#2 | |
| Il-2 (pg) Sample | Lysis Solution | Average | StDeV | Average | StDeV | Average | StDev | Average | StDev |
| haNK003 | Detergent (Triton 0.1%) | 1604.17 | 65.86 | 1685.23 | 49.92 | 10095.68 | 1451.30 | 11636.49 | 311.54 |
|  | Hypotonic (H2O) | 181.93 | 21.80 | 289.54 | 40.03 | 2619.15 | 186.89 | 3301.02 | 14.85 |
| Controls | Detergent (Triton 0.1%) | 0.43 | 0.61 | 0.92 | 1.30 | 0.00 | 0.00 | 0.00 | 0.00 |

Multiplex ELISA IL-2 quantification values were between 5 and 10 times higher than data from sandwich ELISA method. Although there is variability in the absolute values from these two methods, the trends are consistent between both data sets and are summarized below. This data will be useful to allow NantKwest to continue characterizing IL-2 secretion and intracellular IL-2 levels from haNK003 cells as the product is further developed.

In summary, haNK003 cells release a detectable amount of IL-2 into the culture medium (10 to 40 pg/hour per million cells), and the amount of IL-2 released by live cells under steady state culture conditions represents on average less than 10% of the total intracellular IL-2 stock.

Irradiation of the haNK003 cells with a dose of 10 Gy increases the amount of released IL-2 over a period of 48 hours, likely reflecting the presence of dying cells. Furthermore, irradiation does not result in release of IL-2 all at once, but gradually, over time.

To simulate release of IL-2 upon necrotic cell death, haNK003 cells were subjected to hypotonic shock. The amount of IL-2 released under these conditions represents between 14 and 27% of the total intracellular IL-2 determined in Triton X-100 lysates (which solubilizes proteins from all intracellular compartments).

Overall, haNK003 cells secrete low levels of IL-2 (493.8 pg/mL for irradiated cells and 276.1 pg/mL for non-irradiated cells over 6 hours when averaged across all runs from both methods). Taken together, the low level of IL-2 secreted by haNK003 cells, the extremely short half-life of IL-2 in the plasma, and the lack of persistence of irradiated haNK003 cells in vivo, suggest that IL-2 release by infused haNK003 is unlikely to cause a clinical adverse effect.

The effects of irradiation on in vitro proliferative capacity and functionality, as tested in development studies with pre-formulated cells, demonstrate that haNK003 cells have limited proliferation (less than 0.1% of cells) in vitro and that levels of cytotoxic activity and ADCC activity are maintained for at least 6 hours after irradiation.

IL-2 secretion and intracellular IL-2 levels of haNK003 cells pre- and post-irradiation demonstrate that haNK003 cells secrete low levels of IL-2. haNK003 cells, irradiated or non-irradiated, do not release amounts of IL-2 that would be anticipated to have an adverse effect in humans.

Example 4. Tolerability and Tumorigenicity of Single-Dose haNK003 Cells Administered Intravenously Natural killer (NK) cells are potent cytotoxic effector cells for cancer therapy and potentially for viral infections. NantKwest has successfully established unique NK cell-based platforms to produce GMP-grade activated NK (aNK cells). aNK cells are actively being pursued in the clinic for cellular therapy of patients with a variety of advanced hematological malignancies and solid tumors. Recently a GMP-grade plasmid-transfected variant of NK-92 expressing the high-affinity CD16 receptor was developed utilizing a novel transfection vector containing the ER IL-2 gene, enabling the resulting haNK003 cells to grow independently of IL-2. Expression of the high-affinity CD16 receptor enables haNK003 cells display high antibody-dependent cell-mediated cytotoxicity (ADCC) in combination with rituximab and trastuzumab and daratumumab against target cell lines that were not killed by the parental NK-92 cells. One cell clone was selected to generate the Master Cell Bank, haNK003, which is in clinical development.

Materials and Methods

Eighteen (18) NOD.CB17-Prkdc$^{scid}$/J (NOD/SCID) mice (9 male and 9 female) were used to investigate tolerability and tumorigenicity of single-dose haNK003 cells administered intravenously in NOD/SCID mice. The mice were obtained from Jackson Laboratory (610 Main Street Bar Harbor, Me. 04609 US).

18 NOD/SCID mice were selected and randomly assigned to 3 groups with 6 mice (3 male and 3 female) per group based on animal body weight. Mice were intravenously administered with a single dose of PBS, non-irradiated or 10-Gy irradiated haNK003 cells, as indicated in Table 6. Animals were then monitored by daily observation and twice weekly animal body weight measurement. After 5 weeks, animals were euthanized and major organs were harvested and processed for further histopathological examination and immunohistochemistry analysis with anti-CD56 antibody.

TABLE 6

Study Design

| Group | Animal No. | Animal Sex | Treatment | Dose | Dosing Schedule | Route |
|---|---|---|---|---|---|---|
| A | 3 | M | PBS | / | Single Dose | IV |
|  | 3 | F | PBS | / | Single Dose | IV |
| B | 3 | M | Non-irradiated haNK003 | $1 \times 10^7$ cells | Single Dose | IV |
|  | 3 | F | Non-irradiated haNK003 | $1 \times 10^7$ cells | Single Dose | IV |

TABLE 6-continued

Study Design

| Group | Animal No. | Animal Sex | Treatment | Dose | Dosing Schedule | Route |
|---|---|---|---|---|---|---|
| C | 3 | M | Irradiated haNK003 | $1 \times 10^7$ cells | Single Dose | IV |
|   | 3 | F | Irradiated haNK003 | $1 \times 10^7$ cells | Single Dose | IV |

For cell culture, the haNK003 cells were cultured in X-Vivo10 medium (Cat #BE02-055Q) supplemented with 5% heat inactivated human AB serum (Cat #IPLA-SERAB-HI, Innovative Research), 100 U penicillin/ml and 100 µg/ml streptomycin (Corning, Cat #30-002-CI).

For irradiation, the haNK003 cells growing in an exponential growth phase were harvested and counted for viable cell number and viability. On the appropriate day, half of the haNK003 cells were irradiated with a dose of 1000 cGy using JL Shephard Mark 1 Model 68 $_{137}$Cs irradiator (service provided by the Department of Radiation Oncology, the University of California, Irvine, Calif. 92697).

For cell preparation for dosing, non-irradiated or irradiated haNK003 cells were kept on ice during transportation to the animal facility (1124 W. Carson Street, Torrance, Calif., 90502). Cells were washed twice with cold PBS, and then re-suspended in an appropriate amount of cold PBS and passed through a 40 µm cell strainer to make a single cell preparation with a final cell density of $5 \times 10_7$ viable cells/ml. Cell viability was determined with the Vi-CELL cell viability analyzer, and only cells with over 85% viability were used for this study. Then these non-irradiated or irradiated haNK003 cells were stored at room temperature for IV dosing animals in an appropriate Group, respectively.

18 NOD/SCID mice were selected and randomly assigned to 3 groups with 6 mice (3 male and 3 female) per group based on animal body weight.

On an appropriate day, each animal in Group A received a specific amount of PBS respectively. The dosing volume was 200 µl, regardless of individual animal body weight. The dosing route was IV injection via tail vein, and the dosing schedule was a single dose, as indicated in the study protocol. On an appropriate day, each animal in Groups B and C received $1 \times 10^7$ non-irradiated and irradiated haNK003 cells in 200 µl PBS, respectively. The dosing volume was 200 µl, the dosing route was IV injection via tail vein; and the dosing schedule was a single dose.

Animals were observed once daily for general appearance. Clinical observations were conducted twice daily and recorded. Animals were routinely monitored after treatment for effects on normal behavior such as mobility, food and water consumption (by visual estimation), and body weight (gain/loss).

Summary statistics, including mean and standard error of the mean (SEM), were provided for the animal body weight of each group at each time point. Statistical analyses of difference in animal body weight change among the groups were evaluated using two-way ANOVA with repeated measures followed by Bonferroni test. All the data were analyzed using GraphPad Prism software version 5. $p<0.05$ was considered to be statistically significant.

Results

Figure 11:
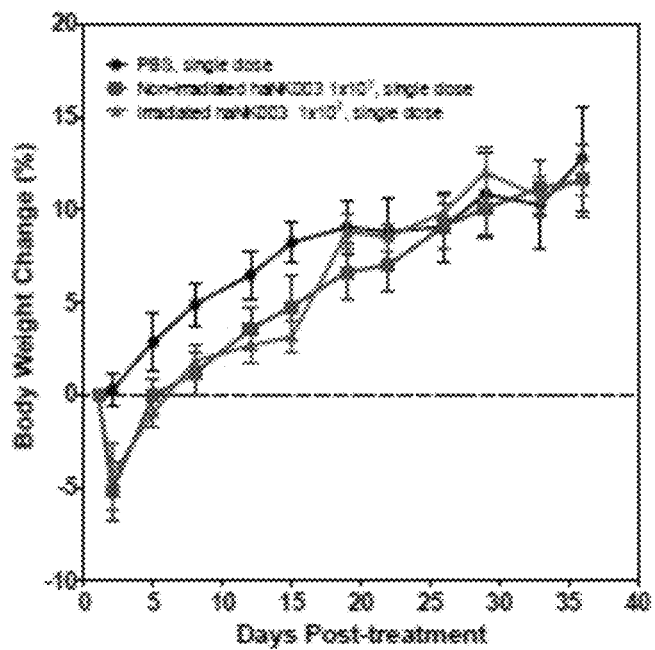
FIG. 11 is a graph showing the effect of haNK003 administered intravenously on animal body weight in NOD/SCID mice. NOD/SCID mice (3 male and 3 female per group) were treated by i.v. injection of PBS, non-irradiated or irradiated haNK003 cells at the dose of $1 \times 10^7$ cells as a single dose, respectively. Animal body weight was monitored twice weekly for 5 weeks. Values are mean±SEM, n=6.

Non-irradiated or irradiated haNK003 cells at the dose of $1 \times 10^7$ cells, administered intravenously as a single agent, were well-tolerated with a maximum average body weight loss of 5.2% and 4.4%, respectively. There was no significant body weight loss in NOD/SCID mice when administered with a single dose of either irradiated or non-irradiated haNK003 cells ($1 \times 10^7$), compared to PBS-treated control group, as indicated in Table 7, FIG. 11. There was not any treatment related mortality that occurred over 5-weeks of observation in all treatment groups, as shown in Table 7.

There were not any visible tumor masses in all the tissues and organs assessed, including brain, heart, liver, lung, kidney, spleen and thymus in all treatment groups, regardless of male or female mice. Results from histology analysis and IHC staining using anti-CD56 antibody confirmed that there were not any haNK003 cell-related lymphoid aggregates in tissues and organs, including brain, bone marrow, heart, liver, lung, kidney, spleen and thymus, suggesting that both non-irradiated and irradiated haNK003 cells have no tumorigenic potential in NOD/SCID mice.

Pathological examination of all the specimens obtained in the study, including brain, bone marrow, heart, liver, lung, kidney, spleen and thymus, indicated that there was not any significant haNK003 treatment related toxicities in either non-irradiated or irradiated haNK003 cells-treated group, compared to PBS treated group.

TABLE 7

Effect of haNK003 administered intravenously on animal body weight, mortality and tumorigenicity in NOD/SCID mice.

| Group | Treatment | Dose | Dosing Schedule | MWL[a] (%) | P value[b] | Mortality[c] (n/total) | Tumorigenicity |
|---|---|---|---|---|---|---|---|
| A | PBS | / | Single Dose | / | / | 0/6 | NO |
| B | Non-irradiated haNK003 | $1 \times 10^7$ cells | Single Dose | 5.2 | P > 0.05 | 0/6 | NO |
| C | Irradiated haNK003 | $1 \times 10^7$ cells | Single Dose | 4.4 | p > 0.05 | 0/6 | NO |

Note:
[a]MWL: maximum body weight loss;
[b]p-value (two-way ANOVA with repeated measures followed by Bonferroni test) vs. PBS treatment;
[c](n/total): number of treatment related animal deaths per total number of animals in an individual group.

Either Irradiated or non-irradiated haNK003 cells as a single agent administered intravenously at the dose of $1 \times 10^7$ cells were well-tolerated in both male and female NOD/SCID mice. There was no significant body weight loss associated with either irradiated or non-irradiated haNK003 treatment. There was not any treatment related mortality that occurred over 5-weeks of observation in all treatment groups. There were not any significant pathological changes in the major organs including brain, bone marrow, heart, liver, lung, kidney, spleen and thymus. Most importantly, there was no tumorigenic potential of irradiated or non-irradiated haNK003 cells in both male and female NOD/SCID mice.

Example 5. Tolerability and Tumorigenicity of Repeated-Dose haNK003 Cells Administered Intravenously Materials and Methods Eighteen (18) NOD.CB17-Prkdcscid/J (NOD/SCID) mice (9 male and 9 female) were used to investigate tolerability and tumorigenicity of single-dose haNK003 cells administered intravenously in NOD/SCID mice. The mice were obtained from Jackson Laboratory (610 Main Street Bar Harbor, Me. 04609 US).

18 NOD/SCID mice were selected and randomly assigned to 3 groups with 6 mice (3 male and 3 female) per group based on animal body weight. Mice were intravenously administered with repeated dose of PBS, non-irradiated or 10-Gy irradiated haNK003 cells once weekly for 4 weeks, respectively as indicated in Table 8. Animals were then monitored by daily observation and twice weekly animal body weight measurement. After 5 weeks, animals were euthanized and major organs were harvested and processed for further histopathological examination and immunohistochemistry (IHC) analysis with anti-CD56 antibody.

TABLE 8

Study Design.

| Group | Animal No. | Animal Sex | Treatment | Dose | Dosing Schedule | Route |
|---|---|---|---|---|---|---|
| A | 3 | M | PBS | / | QW × 4 | IV |
|   | 3 | F | PBS | / | QW × 4 | IV |
| B | 3 | M | Non-irradiated haNK003 | 1 × 10$^7$ cells | QW × 4 | IV |
|   | 3 | F | Non-irradiated haNK003 | 1 × 10$^7$ cells | QW × 4 | IV |
| C | 3 | M | Irradiated haNK003 | 1 × 10$^7$ cells | QW × 4 | IV |
|   | 3 | F | Irradiated haNK003 | 1 × 10$^7$ cells | QW × 4 | IV |

For cell culture, haNK003 cells were cultured in X-Vivo10 medium (Cat #BE02-055Q) supplemented with 5% heat inactivated human AB serum (Cat #IPLA-SERAB-HI, Innovative Research), 100 U penicillin/ml and 100 µg/ml streptomycin (Corning, Cat #30-002-CI).

For irradiation, haNK003 cells growing in an exponential growth phase were harvested and counted for viable cell number and viability. On the appropriate day, half of the haNK003 cells were irradiated with a dose of 1000 cGy using JL Shephard Mark 1 Model 68 $_{137}$Cs irradiator (service provided by the Department of Radiation Oncology, the University of California, Irvine, Calif. 92697).

For cell preparation for dosing, Non-irradiated or Irradiated haNK003 cells were kept on ice during the transportation to animal facility (1124 W. Carson Street, Torrance, Calif., 90502). Cells were washed twice with cold PBS, and then re-suspended in appropriate amount of cold PBS and passed through 40 µm cell strainer to make single cell preparation with a final cell density of 5×10$_7$ cells/ml. Cell viability was determined with Vi-CELL cell viability analyzer, and only cells with over 85% viability were used for this study. Then these non-irradiated or irradiated haNK003 cells were stored at RT for IV dosing animals in an appropriate group, respectively.

18 NOD/SCID mice were selected and randomly assigned to 3 groups with 6 mice (3 male and 3 female) per group based on animal body weight.

On an appropriate day, each animal in Group A received 200 µl of PBS, regardless of an individual animal body weight. The dosing route was IV injection via tail vein, and the dosing schedule was once weekly for total 4 weeks, as indicated in the study protocol (Appendix 1). Each animal in Groups B and C received 1×10$_7$ non-irradiated and irradiated haNK003 cells in 200 µl PBS, respectively. The dosing volume was 200 µl, the dosing route was IV injection via tail vein, and the dosing schedule was once weekly for total 4 weeks, as indicated in the study protocol.

Animals were observed once daily for general appearance. Clinical observations were conducted twice daily and recorded. Animals were routinely monitored after treatment for effects on normal behavior such as mobility, food and water consumption (by visual estimation), and body weight (gain/loss).

Summary statistics, including mean and standard error of the mean (SEM), were provided for the animal body weight of each group at each time point. Statistical analyses of difference in animal body weight change among the groups were evaluated using two-way ANOVA with repeated measures followed by Bonferroni test. All the data were analyzed using GraphPad Prism software version 5. $p<0.05$ was considered to be statistically significant.

Results

Figure 12:
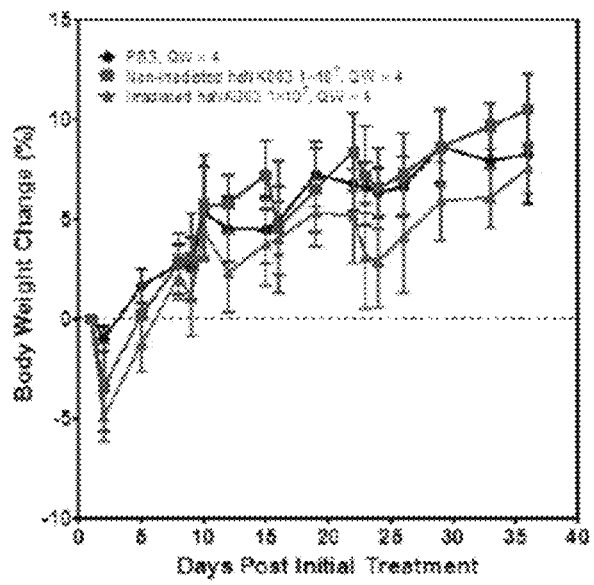
FIG. 12 is a graph showing the effect of haNK003 cells on animal body weight in NOD/SCID mice. NOD/SCID mice (3 male and 3 female per group) were treated with PBS, $1\times10^7$ of non-irradiated or irradiated haNK003 cells once weekly for 4 weeks, animal body weight was monitored twice weekly for 5 weeks. Values are mean±SEM, n=6.
Figure 13:
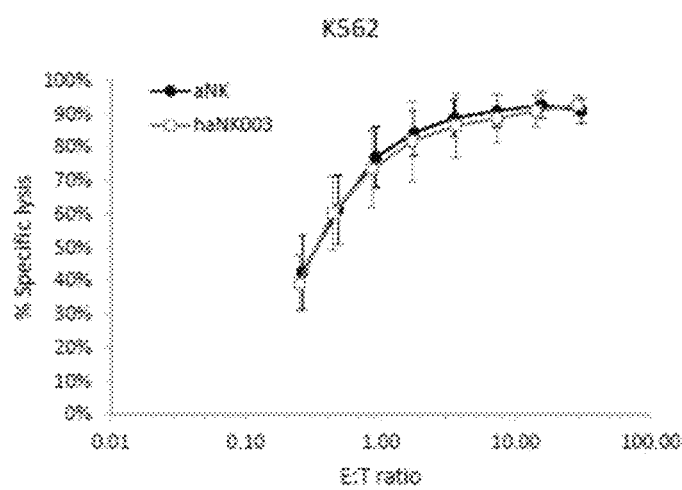
FIG. 13 is a graph showing the comparison of aNK vs. haNK003 cells with respect to natural cytotoxicity against K562 cells.
Figure 14:
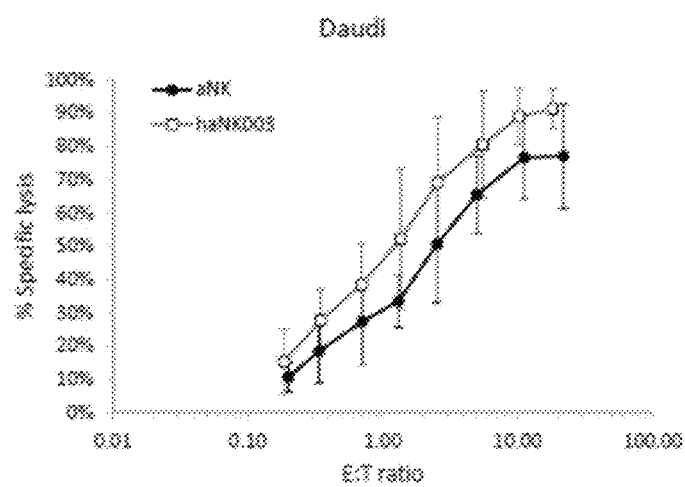
FIG. 14 is a graph showing the comparison of aNK vs. haNK003 cells with respect to natural cytotoxicity against Daudi cells.
Figure 15:
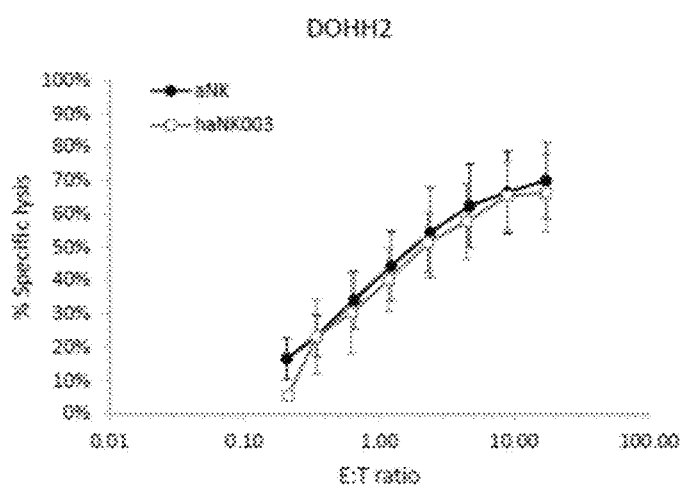
FIG. 15 is a graph showing the comparison of aNK vs. haNK003 cells with respect to natural cytotoxicity against DOHH2 cells.
Figure 16:
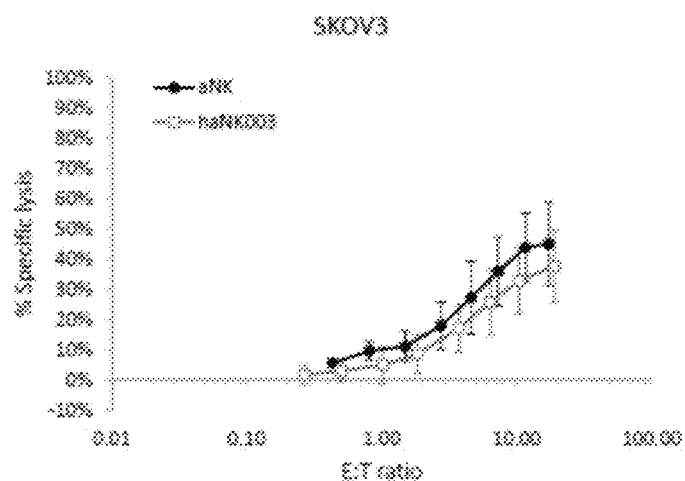
FIG. 16 is a graph showing the comparison of aNK vs. haNK003 cells with respect to natural cytotoxicity against SKOV-3 cells.
Figure 17:
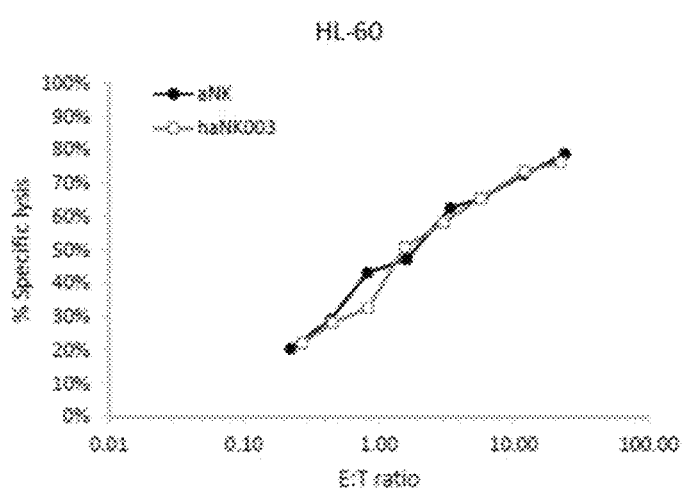
FIG. 17 is a graph showing the comparison of aNK vs. haNK003 cells with respect to natural cytotoxicity against HL-60 cells.
Figure 18:
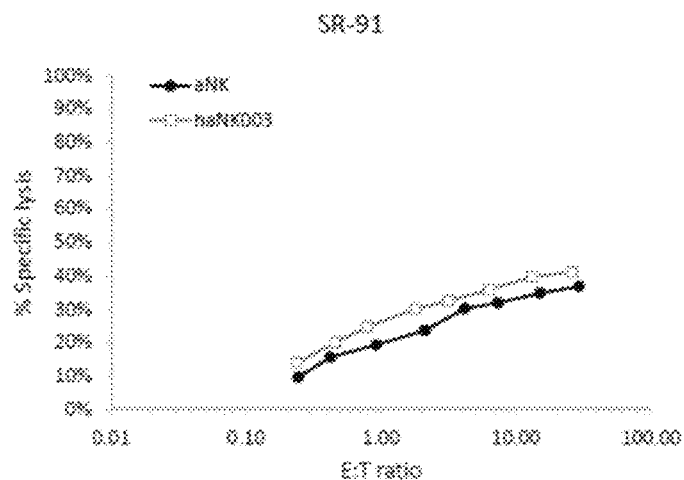
FIG. 18 is a graph showing the comparison of aNK vs. haNK003 cells with respect to natural cytotoxicity against SR-91 cells.

Non-irradiated or irradiated haNK003 cells as a single agent administered intravenously once weekly for 4 weeks, were well-tolerated with a maximum average body weight loss of 3.4% and 4.9%, respectively. Regardless male or female mice, there was no significant body weight loss in NOD/SCID mice when administered with either non-irradiated or irradiated haNK003 cells (1×10$^7$), compared to PBS-treated control group, as indicated in Table 9, FIG. 12. There was not any treatment related mortality that occurred over 5-week of observation in all treatment groups, as summarized in Table 9.

TABLE 9

Effect of haNK003 cells on animal body weight, mortality and tumorigenicity in NOD/SCID mice.

| Group | Treatment | Dose | Dosing Schedule | MWL[a] (%) | P value[b] | Mortality[c] (n/total) | Tumorigenicity |
|---|---|---|---|---|---|---|---|
| A | PBS | / | QW × 4 | 1.0 | / | 0/6 | NO |
| B | Non-irradiated haNK003 | 1 × 10$^7$ cells | QW × 4 | 3.4 | P > 0.05 | 0/6 | NO |

TABLE 9-continued

Effect of haNK003 cells on animal body weight, mortality and tumorigenicity in NOD/SCID mice.

| Group | Treatment | Dose | Dosing Schedule | MWL[a] (%) | P value[b] | Mortality[c] (n/total) | Tumori- genicity |
|---|---|---|---|---|---|---|---|
| C | Irradiated haNK003 | 1 × 10⁷ cells | QW × 4 | 4.9 | p > 0.05 | 0/6 | NO |

Note:
[a]MWL: maximum body weight loss;
[b]p-value (two-way ANOVA with repeated measures followed by Bonferroni test) vs. PBS treatment;
[c](n/total): number of treatment related animal deaths per total number of animals in an individual group.

Macropathological and histopathological examination of all the specimens obtained in this study, including brain, bone marrow, heart, liver, lung, kidney, spleen and thymus, indicated that there was not any significant haNK003 treatment related toxicities in these organs in either nonirradiated or irradiated haNK003 cell treated groups, compared to PBS-treated control group. There was no splenomegaly identified in all animals. There were no tumor masses found by gross findings in all treatment groups. Results from IHC using anti-CD56 antibody confirmed that there were not any haNK003 cell-related lymphoid aggregates in tissues and organs including bone marrow, brain, liver, lung, heart, kidney, spleen, thymus, etc, over 5-week of follow-up, suggesting that there was no irradiated or non-irradiated haNK003 cells related leukemia or tumor development in NOD/SCID mice over these 5 weeks.

There was no edema, no degeneration, and no necrosis present in all these tissues. Compared to PBS control group, very focal mild and minimum fatty changes in the liver tissues were noted in non-irradiated and irradiated haNK003 treatment groups, respectively. It is also noteworthy that the liver parenchyma in PBS, non-irradiated or irradiated haNK003 treatment groups showed rare minute foci of mixed inflammatory cells including neutrophils and mononuclear cells, since these small cluster cells were CD56 negative, suggesting these mixed inflammatory cells very likely resulted from repeated procedures (tail vein injection), not related with haNK003 treatment.

In summary, non-irradiated and irradiated HaNK003 cells were well-tolerated. There were not any significant haNK003 treatment related toxicities or tumorigenicity issues in NOD/SCID mice at this dosing regimen.

Example 6. Comparison of aNK and haNK003 Natural Cytotoxic Activity

A major mechanism by which Natural Killer (NK) cells kill target cells is through the formation of a cellular junction and the subsequent secretion of perforin and granzymes. This in turn induces an apoptotic process within the target cell leading to disintegration of the plasma membrane and cell death. Target cells can be recognized by the expression of stress antigens characteristic of virally infected cells and/or transformed cells. The recognition and subsequent killing of a target cell through engagement of stress antigens with activating receptors on NK cells is termed natural (or direct) cytotoxicity.

As natural cytotoxicity is a major functional characteristic of NK cells, an analysis of this functionality in cell variants and comparison to activated NK-92 cell (aNK) activity can help establish the impact of a particular genetic modification of aNK cells.

Materials and Methods

Six (6) cell lines representative of liquid and solid tumors were selected as targets. Targets were also selected so as to represent a range of sensitivities to aNK cell killing, with SR-91 being relatively insensitive to killing and K562 being highly sensitive to killing, and others falling somewhere in between. Targets and effector cells (haNK003 or aNK) were co-incubated for 4 hours at 37° C. and target cell killing was determined by flow cytometry using an in-house developed method to determine the specific cytotoxicity of effector cells against target cells loaded with PKH67 fluorescent dye staining. The PKH67 Fluorescent Cell Linker Kits use proprietary membrane labelling technology (Sigma-Aldrich) to stably incorporate a green fluorescent dye with long aliphatic tails (PKH67) into lipid regions of the cell membrane. Due to its longer aliphatic carbon tails, PKH67 exhibits reduced cell-cell transfer. PKH67 is well suited for cytotoxicity assays that use propidium iodide as viability probe. Staining with propidium iodide differentiates dead target cells (which will be doubly stained) from dead effector cells (aNK or haNK cells).

For cell culture, aNK cells were cultured in X-Vivo 10 medium supplemented with 5% heat inactivated human AB serum (from CMV-negative tested donors) and 500 IU/ml recombinant human IL-2. aNK cultures were passaged every 1-4 days in order to keep the cell density >10e5 cells/mL and <10e6 cells/mL. haNK003 cells were cultured in X-Vivo 10 medium supplemented with 5% heat inactivated human AB serum (from CMV-negative tested donors), without IL-2. haNK003 cultures were passaged every 1-4 days in order to keep the cell density >10e5 cells/mL and <10e6 cells/mL. K562, Daudi, DOHH2, HL-60, SR-91, and SKOV3 cells were cultured in RPMI-1640 supplemented with 10% heat inactivated fetal bovine serum (FBS) and a cocktail of antibiotics/antimycotic. Cells growing in suspension were passaged by simple dilution, while adherent cells (SKOV3) were passaged by trypsinization of the culture using TrypLE™. Passages were every 2-5 days (depending of the particular doubling time of the cell line), or whenever the culture medium appeared yellow (acidic) indicating spent medium.

For sample preparation, suspension-growing cell lines were resuspended by up and down pipetting of the cell cultures. Adherent target cell lines (SKOV3) were enzymatically detached from culture vessels using TrypLE™ and resuspended by up and down pipetting of the trypsinized cells pellet. Cells viability was determined by manual counting (trypan blue exclusion method). Dilutions of target and effector cells to the required cell concentrations were made in RPMI-1640 supplemented with 10% heat-inactivated FBS and antibiotics/antimycotic. Effector and target cells were mixed at different effector to target (E:T of 20:1, 10:1, 5:1, 2.5:1, 1.25:1, 0.62:1, 0.31:1, and 0.15:1) ratios in a 96-well plate and co-incubated for 4 hours in a 5% $CO_2$ atmosphere 37° C. incubator.

Samples were analyzed on a MACSQuant flow cytometer (Miltenyi), using the B1 (FITC) and B3 (PerCP-Vio700/PI) fluorescence channels. Targets alone −PI and +PI were used to determine the B1/B3 compensation parameters.

Cytotoxicity % was calculated by the formula=[(% FITC+/PI+ cells in samples)−(% FITC+/PI+ in Targets +PI only)]/[100−(% FITC+/PI+ in Targets+PI only)]

were obtained from Jackson Laboratory (610 Main Street Bar Harbor, Me. 04609 US).

MDA-MB-453 HER2− positive human breast carcinoma s.c. xenograft model was established in female NSG mice. Once the average size of tumors reached about 100 mm$^3$, treatment was initiated, and anti-tumor activity of haNK003 cells as a single agent were evaluated in this xenograft model. Other test articles were evaluated in parallel under the protocol LABC-X01612, but only the results of haNK003 in comparison to PBS are presented herein. The haNK003 treatment groups and dosing regimen design are described in Table 10.

TABLE 10

Study Design.

| Group | Treatment | Animal No. | Dose | Test Article Concentration | Dose Volume | Dosing Schedule | Dosing Route |
|---|---|---|---|---|---|---|---|
| A | PBS | 4 | / | / | 200 μl | Twice weekly × 4 | IV |
| F | Irradiated haNK003 | 4 | $2.5 \times 10^6$ cells | $1.25 \times 10^7$ cells/ml | 200 μl | Twice weekly × 4 | IV |
| G | Irradiated haNK003 | 4 | $1 \times 10^7$ cells | $5 \times 10^7$ cells/ml | 200 μl | Twice weekly × 4 | IV |

Results aNK and haNK003 cells used for this study were thawed on Jul. 22, 2016. All the target cell cultures used in this study were less than 8 weeks old. Target cells and effector cells cultures were passaged at most 48 hours before the assay.

The results shown in FIGS. 13-18 confirm the sensitivity of the target cell lines to killing by aNK with K562 being the most sensitive (75% specific lysis at low effector to target ratios of 1:1). Daudi, DOHH2 and HL-60 demonstrated intermediate sensitivity requiring a higher effector to target ratio (10:1) to achieve 65-80% specific lysis. SKOV3 and SR-91 were the most resistant requiring effector to target ratios in excess of 10:1 to achieve specific lysis of approximately 40%. In each case, the natural cytotoxic activity of haNK003 was comparable to that of aNK and generally followed the same activity profile within the error ranges of the experiment.

aNK and haNK003 cells show comparable cytotoxic activity against the six cancer cell lines tested demonstrating that the natural cytotoxic activity of aNK cells is essentially the same despite the genetic modification used to create the haNK003 cells. haNK003 cells and aNK cells are comparable in functionality with respect to natural cytotoxic activity.

Example 7. Evaluation of the Anti-Tumor Activity of haNK003 in MDA-MB-453 Human Breast Carcinoma Subcutaneous Mouse Model In this study, the anti-tumor activity of haNK003 cells as a single agent were evaluated in the MDA-MB-453 human breast carcinoma subcutaneous xenograft model in female NOD.Cg-Prkdc$^{scid}$ Il2rg$^{tm1Wjl}$/SzJ (NOD scid gamma, NSG) mice.

Materials and Methods

Twelve NOD.Cg-Prkdc$^{scid}$ Il2rg$^{tm1Wjl}$/SzJ (NOD scid gamma, NSG) mice were used to evaluate the anti-tumor activity of haNK003 in the MDA-MB-453 human breast carcinoma subcutaneous (s.c.) xenograft model. The mice For tumor cell culture, MDA-MB-453 human breast carcinoma cells (ATCC, Cat #HTB-131) were cultured in ATCC-formulated Leibovitz's L-15 medium (ATCC, Cat #30-2008) supplemented with 10% heat-inactivated FBS (GeneTex, Cat #GTX73252), 100 U penicillin/ml and 100 μg/ml streptomycin (Corning, Cat #30-002-CI).

For tumor cell injection, each animal was weighed, and then injected subcutaneously in the left and right flank area with 0.1 ml of $1.0 \times 10_8$ of MDA-MB-453 human breast cancer cells per mL in 50% Matrigel (Corning, Cat #354234) with 25-gauge needle. Cell viability was determined with Vi-CELL cell viability analyzer, and only cells with over 95% viability were used for this in vivo study.

For haNK003 cell culture, haNK003 cells were cultured in X-Vivo10 medium (Lonza, Cat #BE02-055Q) supplemented with 5% heat inactivated human AB serum (Innovative Research, Cat #IPLA-SERAB-HI), 100 U penicillin/ml and 100 μg/ml streptomycin.

For irradiation, haNK003 cells growing in an exponential growth phase were harvested and counted for viable cell number and viability. On the appropriate day, the haNK003 cells were irradiated with a dose of 1000 cGy using JL Shephard Mark 1 Model 68 $_{137}$Cs irradiator (service provided by the Department of Radiation Oncology, the University of California, Irvine, Calif. 92697).

For cell preparation for dosing, Irradiated haNK003 cells were kept on ice during the transportation to animal facility (1124 W. Carson Street, Torrance, Calif., 90502). Cells were washed twice with cold PBS, and then were re-suspended in appropriate amount of cold PBS and passed through 40 μm cell strainer (Corning, Cat #431750) to make single cell preparation with a final cell density of $1.25 \times 10_7$ or $5 \times 10_7$ cells/ml, respectively. Then these irradiated haNK003 cells were stored at RT for IV dosing for animals in an appropriate Group, respectively.

12 NSG mice were selected and randomly assigned to 3 study groups with 4 mice per group based on appropriate tumor sizes. Randomization was based on total tumor volume for each animal and animal body weight. For this efficacy study, once the average size of tumors reached about 100 mm$_3$, randomization was conducted and treatment was initiated.

The dosing volume was 200 µl, regardless of an individual animal body weight. The dosing route was IV injection via tail vein, and the dosing schedule was twice weekly for total 4 weeks, as indicated in the study protocol. On an appropriate day, each animal in Groups F and G received 2.5×10$_6$ and 1×10$_7$ irradiated haNK003 cells in 200 µl PBS, respectively. The dosing volume was 200 µl, the dosing route was IV injection via tail vein, and the dosing schedule was twice weekly for total 4 weeks.

Animals were observed once daily for general appearance. Clinical Observations were conducted twice daily and recorded. Animals were routinely monitored after treatment for effects on normal behavior such as mobility, food and water consumption (by visual estimation), and body weight (gain/loss).

Tumor size was measured twice weekly in three dimensions using a digital hand held caliper (once tumor emerges) prior to the first dosing and then twice weekly prior to euthanasia. The major endpoint was inhibition or reduction of tumor growth. The tumor volume was expressed in mm$_3$ using the formula: V=0.5×L×W×H where L, W and H are the length, width and height of the tumor, respectively. The tumor volume was then used for calculations of T/C values. T/C (%)=ΔT/ΔC×100, where the ΔT and ΔC are the changes in the mean tumor volumes between an observation day and the first day of measurement for the treatment and control groups, respectively.

Summary statistics, including mean and standard error of the mean (SEM), were provided for the tumor volume or animal body weight of each group at each time point. Statistical analyses of difference in tumor volume or animal body weight change among the groups were evaluated using two-way ANOVA with repeated measures followed by Bonferroni test. All the data were analyzed using GraphPad Prism software version 5. p<0.05 was considered to be statistically significant.

Results

Figure 19:
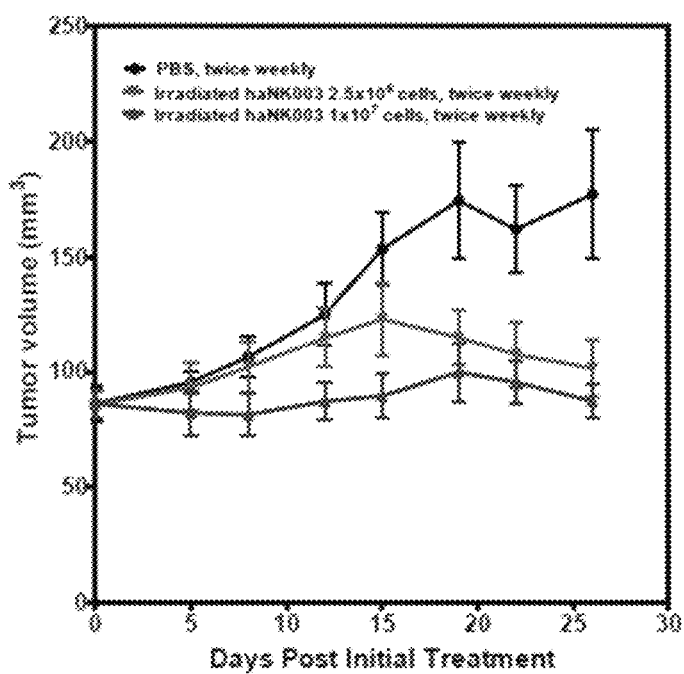
FIG. 19 is a graph showing antitumor activity of haNK003 cells in MDA-MB-453 s.c. xenograft model in female NSG mice. Female NSG mice bearing MDA-MB-453 human breast carcinoma tumors were treated by i.v. injection of PBS or irradiated haNK003 cells at the dose of $2.5\times10^6$ or $1\times10^7$ cells twice weekly for four weeks, respectively. Tumor volumes were monitored twice weekly. Values are mean±SEM; n=8.
Figure 20:
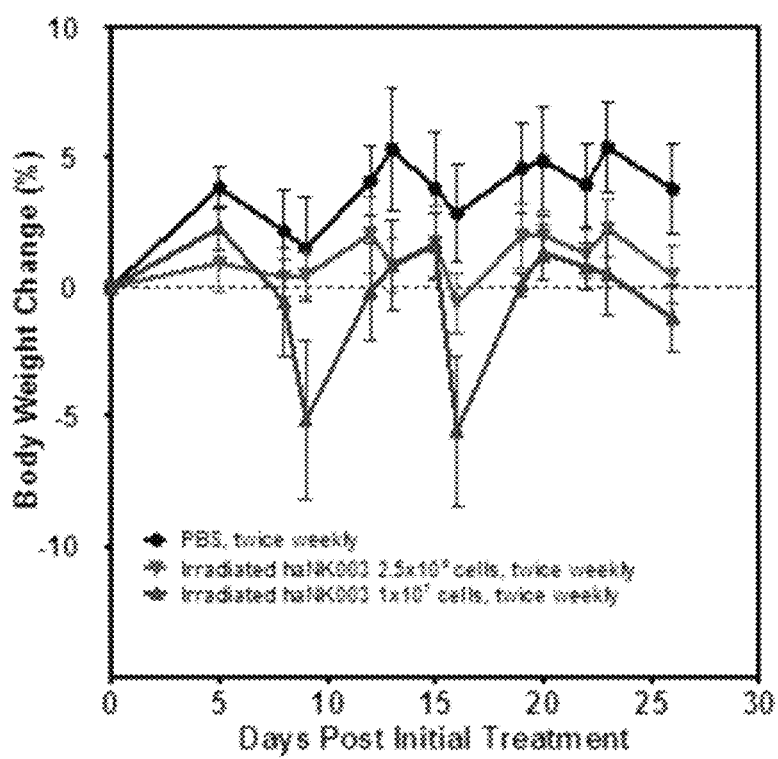
FIG. 20 is a graph showing effect of haNK003 cells on animal body weight in female NSG mice. Female NSG mice bearing MDA-MB-453 human breast carcinoma tumors were treated by i.v. injection of PBS or irradiated haNK003 cells at the dose of $2.5\times10^6$ or $1.0\times10^7$ cells twice weekly for four weeks, respectively. Mice body weights were monitored twice weekly. Values are mean±SEM; n=4.

Data on the antitumor activity of haNK003 as a single agent in s.c.MDA-MB-453 HER2− positive human breast carcinoma xenograft in female NSG mice is presented. A summary of the results is tabulated in Table 11. haNK003 cells, administered intravenously as a single agent at the dose of 2.5×10$^6$ or 1.0×10$^7$ cells twice weekly for 4 weeks, significantly inhibited tumor growth with T/C value of 17.4% and 1.3% (p=0.043 and p=0.006, compared to PBS Group), respectively, as shown in Table 11, FIG. 19. HaNK003 at the dose of 2.5×10$^6$ or 1.0×10$^7$ cells was well tolerated with a maximum average body weight loss of 0.6% and 5.6% (p=0.203 and p=0.085, compared to PBS Group), respectively, as indicated in Table 11, FIG. 20. There was not any haNK003 treatment related mortality that occurred in this study, as summarized in Table 11.

TABLE 11

Anti-tumor activity of haNK003 cells in MDA-MB-453 human breast carcinoma s.c. xenograft model in female NSG mice.

| Group | Animal No. | Treatment | Dose | T/C[a] (%) | P value[b] | MWL[a] (%) | Mortality[c] (n/total) |
|---|---|---|---|---|---|---|---|
| A | 4 | PBS | / | / | / | / | 0/4 |
| F | 4 | Irradiated haNK003 | 2.5 × 10$^6$ cells | 17.4 | P = 0.043 | 0.6 | 0/4 |
| G | 4 | Irradiated haNK003 | 1 × 10$^7$ cells | 1.3 | P = 0.006 | 5.6 | 0/4 |

Note:
[a]T/C (%) was calculated using the formula: T/C (%) = ΔT/ΔC × 100, where the ΔT and ΔC are the changes in the mean tumor volumes between day 26 and the first day of measurement for the treatment and control groups, respectively.
[b]MWL: maximum animal body weight loss.
[c]P-value (two-way ANOVA with repeated measures followed by Bonferroni test) vs. PBS treatment Group.

Irradiated haNK003 cells as a single agent at the dose of 2.5×10$^6$ or 1.0×10$^7$ cells significantly inhibited tumor growth in MDA-MB-453 HER2− positive human breast carcinoma xenograft model in female NSG. Irradiated haNK003 cells at both doses were well-tolerated. There was not any haNK003 treatment related mortality that occurred.

Example 8. Expression of Genes Associated with Hypoxia is not Reduced in haNK Cells Natural Killer (NK) cell lytic activity is suppressed in hypoxic environments in vitro (1% O$_2$) and is associated with downregulation of NKG2D, perforin and granzyme. There is some variability with NK sensitivity to hypoxia (1% O$_2$) from normal donors. However, NK cell lytic activity can be partially rescued by exogenous IL-2 activation in vitro (16 h, 1000 IU/ml). Further, NK cells retain ADCC capacity at under 1% oxygen conditions.

Figure 21:
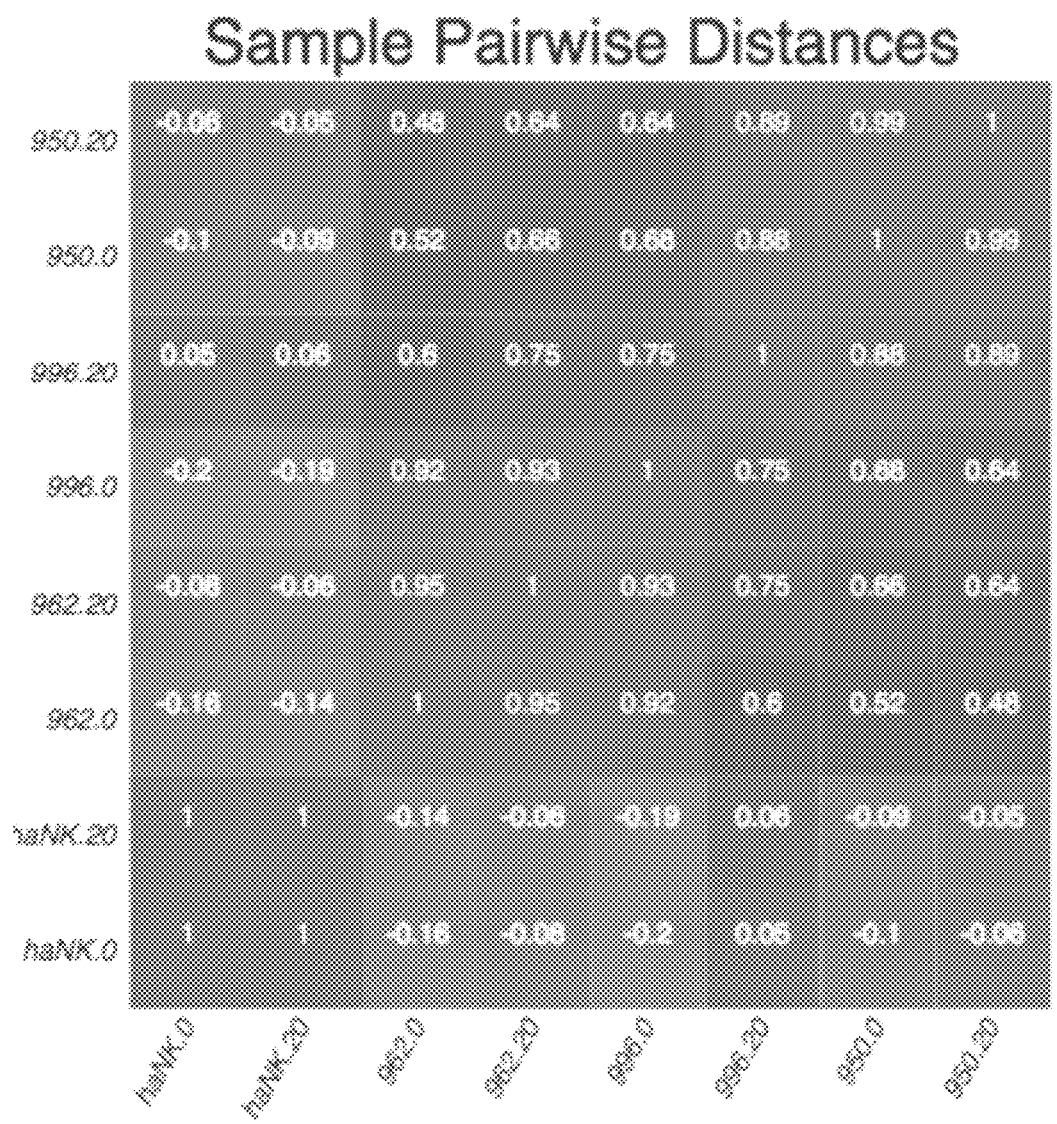
FIG. 21 is a table showing sample pairwise distances for gene expression in normal NK cells 950, 962, and 996 as well as for haNK cells under 20% oxygen and 0% oxygen (hypoxic) conditions.
Figure 22:
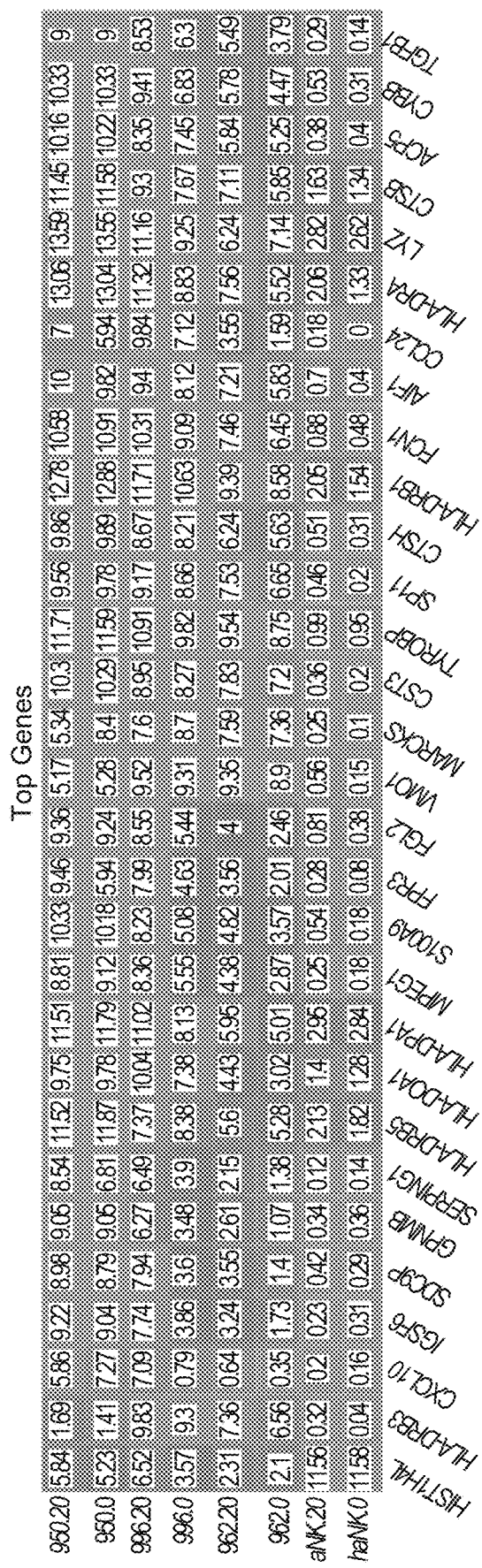
FIG. 22 is a table showing the genes exhibiting the most variability in expression between 20% oxygen conditions and 0% oxygen conditions in 950, 962, 996 and haNK cells.
Figure 23:
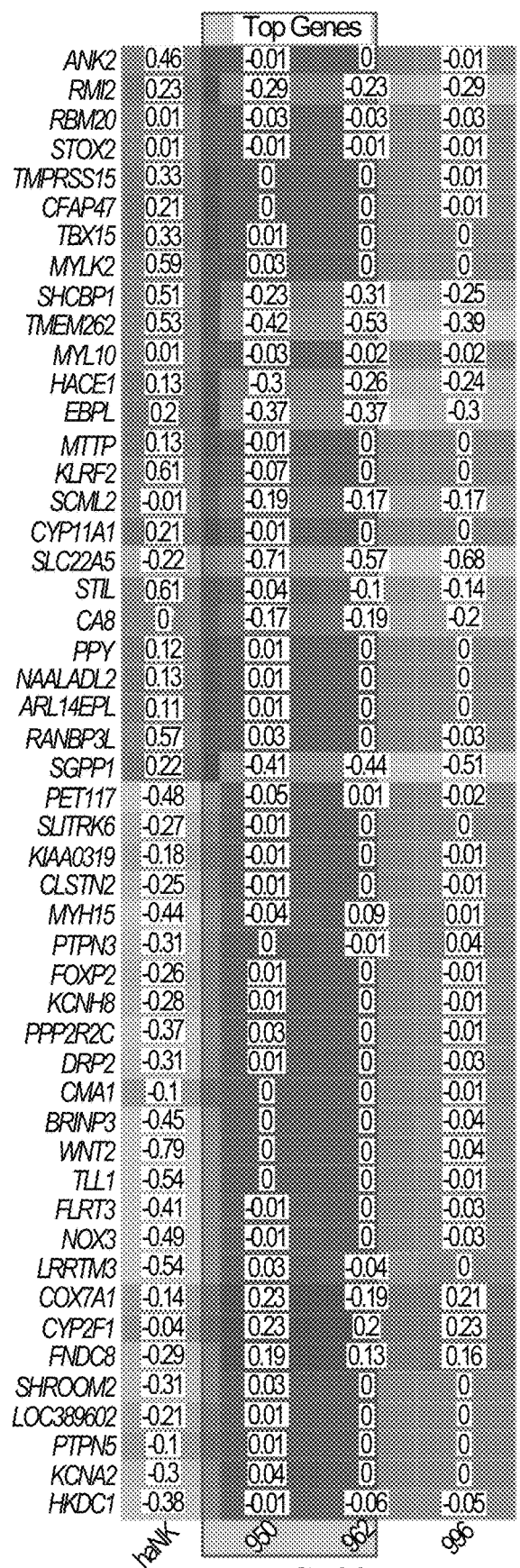
FIG. 23 is a table showing the change in expression in the genes exhibiting the most change between 20% oxygen conditions and 0% oxygen conditions in 950, 962, 996 and haNK cells.
Figure 24:
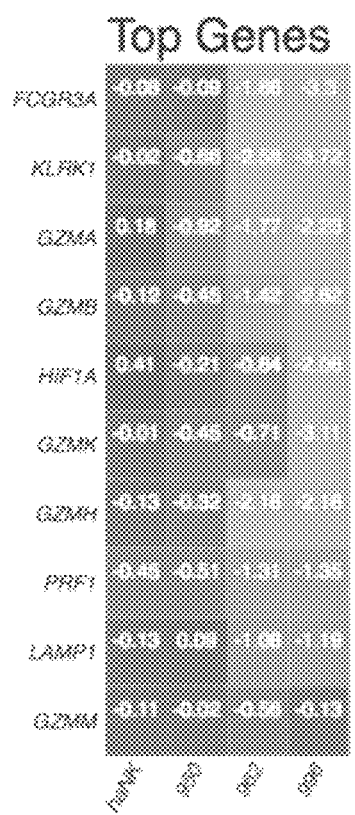
FIG. 24 is a table showing the change in expression in genes associated with hypoxia in haNK cells and NK cells 950, 962 and 996 between 20% oxygen conditions and 0% oxygen conditions.

To determine whether hypoxic conditions alters gene expression in haNK cells, RNA expression was determined in 3 normal donor NK cell populations and haNK cells exposed for 5 hours to 20% or 0% O$_2$. Three Patient Donors NK cell populations (950, 962, 996) were compared to haNK cells under two conditions, 0% oxygen and 20% oxygen. Pairwise sample clustering reveals distinct clusters separating haNK from donor NK cells (See FIG. 21). One patient sample appears to have very little change in expression under hypoxic or pre-hypoxic conditions. Specifically, expression in 962 under 20% oxygen conditions looks very similar to 996 0% oxygen and 962 0% oxygen conditions. See FIG. 21. The genes exhibiting the most variability across the samples are shown in FIG. 22. The genes exhibiting the most change between 20% oxygen conditions and 0% oxygen conditions are shown in FIG. 23. Genes associated with hypoxia showing no change in expression in haNK cells between 20% oxygen conditions and 0% oxygen conditions are shown in FIG. 24. These same genes associated with hypoxia are shown to have reduced expression in 950, 962, and 996 samples albeit less so for the 950 sample. See FIG. 24.

Example 9. CD16 Expression is More Stable in hank003 Cells

It is desirable to have stable expression of CD16 for endowing superior cytotoxicity by serial killing of the target cells during antibody dependent cellular toxicity (ADCC). HaNK-003 (with ER-IL-2) expresses CD16 at a high level following activation with PMA (phorbol-12-myristate 13-acetate) or upon stimulation with K562 target cells compared to peripheral blood NK cells (donor NK cell). Further CD16 levels in hank003 cells were not considerably affected during and after ADCC by measuring CD16 levels by f low cytometry, following the ADCC.

Figure 25:
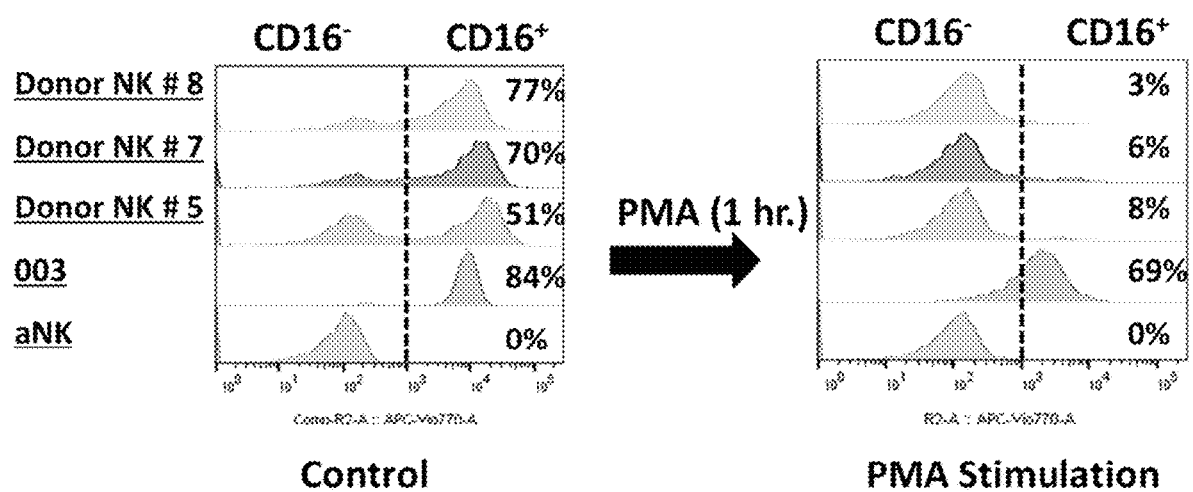
FIG. 25 are graphs showing flow cytometric analysis of CD16 expression in haNK003 cells and donor NK cells before and after PMA treatment. Down regulation of CD16 expression is 94.36%±3 in donor NK cells and 30%±0.04 in haNK003 cells. aNK (NK-92 cells without CD16) were used as a control.

It is known that PMA/ionomycin activation in NK cells leads to activation of CD16-specific protease and cleavage of CD16, resulting in downregulation of CD16 expression level in the NK cells. To determine the effect of PMA/ionomycin, both haNK003 cells and donor NK cells were contacted with 40 nM PMA and 669 nM ionomycin for 1 hour and then checked for CD16 expression level. The PMA/ionomycin treatment resulted in 94.36%±3.00 downregulation of CD16 expression in donor NK cells, whereas in haNK003 cells, the treatment resulted in only 30%±0.04 down-regulation, i.e. three fold less CD16 down regulation than in donor NK cells (FIG. 25).

Figure 26:
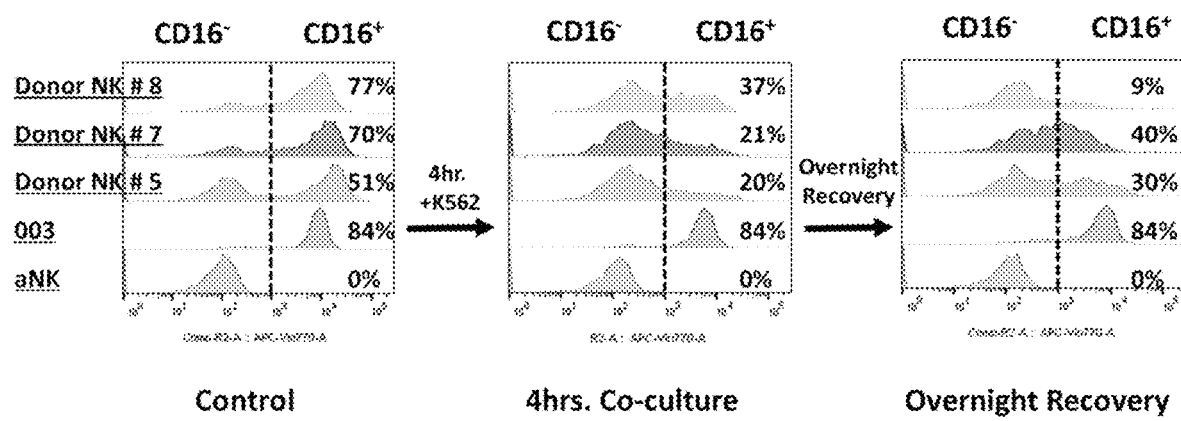
FIG. 26 are graphs showing flow cytometry analysis of CD16 expression level in haNK003 cells and donor NK cells co-cultured with K562 cells (E:T=1:1). After 4 hours haNK003 cells showed stable CD16 expression in comparison to donor NK cells. The CD16 down regulation in donor NK cells after 4 hour of co-culture with K562 was 60.25%±09 and 4.9%±2.57 for haNK003 cells. After overnight recovery, there was still a 57.54%±26.82 downregulation of CD16 expression in donor NK cells, whereas in haNK003 cells the CD16 level recovered to close to normal, with only 2.78%±3.5 of down regulation. aNK (NK-92 cells without CD16) were used as a control.

It is also known that co-culturing of NK cells with K562 cells stimulates the CD16 cleavage protease which leads to shedding of CD16 surface expression in NK cells. Therefore, both the donor NK cells and haNK003 cells were cultured with K562 cells and then measured for CD16 expression after 4 hours of co-culture. Normal co-culture conditions of haNK003 cells with K562 (effectors:targets=1:1) leads to complete cytotoxic killing of target cells within 4 hours. CD16 expression was measured again after another 24 hours to allow for recovery of CD16 expression in haNK003 cells and donor NK cells to determine the percentage of CD16 recovery in haNK003 cells and donor NK cells. It was observed that CD16 expression levels were down regulated by 60.25%±09 in donor NK cells after 4 hours of co-culture. However, in hank003 cells CD16 expression was down regulated by only 4.9%±2.57. After 24 hours, the downregulation of CD16 in donor NK cells was 57.54%±26.82, whereas in haNK003 cells it was only 2.78%±3.5, i.e. close to the original CD16 level (FIG. 26).

Figure 27A:
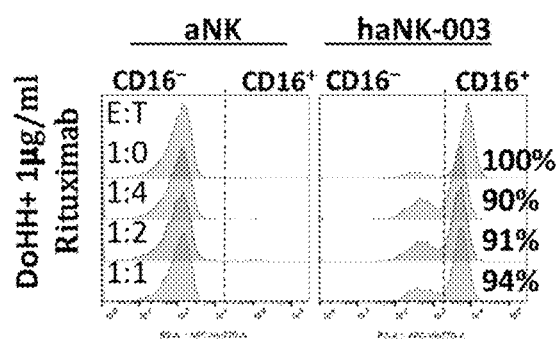
FIGS. 27A and 27B are graphs showing CD16 expression level in haNK003 cells after ADCC. ADCC was performed by co-culturing haNK003 cells and DoHH in presence of 1 µg/ml Rituximab for 4 hours at E:T ratio of 1:0 (effectors alone) to 1:4. CD16 expression level was measured at 4 hours and after 24 hours by flow cytometry.
Figure 27B:
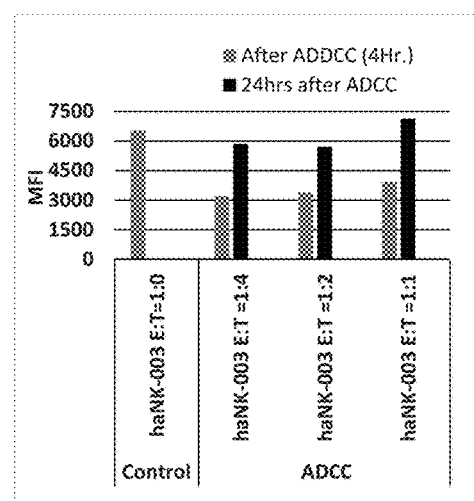

CD16 expression level in haNK003 cells was also measured after antibody-dependent cell-mediated cytotoxicity (ADCC). ADCC was performed by incubating haNK003 cells with DOHH-2 (CD20+ human lymphoma B-cell line) in the presence of Rituximab (CD20-directed cytolytic monoclonal antibody) followed by measurement of CD16 expression. After ADCC, CD16 expression was down regulated by less than 10% in haNK003 cells (FIGS. 27A and 27B). The presence of high levels of CD16 even after ADCC indicated that CD16 expression in haNK003 cells is highly stable.

What is claimed is:

1. A method of treating cancer in a subject in need thereof, the method comprising:
   (a) administering to the subject a population of modified NK-92 cells, wherein the modified NK-92 cells comprise a polypeptide with at least 90% identity to SEQ ID NO:4 (CD16) and a polypeptide with at least 90% identity to SEQ ID NO:6 (IL-2) and wherein the cells comprise SEQ ID NO:1 on chromosome 17, wherein greater than 90% of the cells in the population of cells express CD56, CD16, CD54, and NKp30 and wherein fewer than 5% of the cells in the population of cells express CD3; and
   (b) administering to the subject an antibody.

2. The method of claim 1, wherein the cells comprise a polypeptide with at least 98% identity to SEQ ID NO:4 and a polypeptide with at least 98% identity to SEQ ID NO:6.

3. The method of claim 1, wherein the mean doubling time of the cells is between 55 and 70 hours.

4. The method of claim 3, wherein the population of cells maintains the mean doubling time from 10 days.

5. The method of claim 4, further comprising passaging the population of cells every 1, 2, 3, or 4 days before administration.

6. The method of claim 5, wherein the cells secrete IL-2 at a concentration of 10 to 60 pg/hour per million cells.

7. The method of claim 1, wherein the cells are irradiated cells.

8. The method of claim 7, wherein the cells comprise a polypeptide according to SEQ ID NO:4 and a polypeptide according to SEQ ID NO:6.

9. The method of claim 3, wherein the antibody is a monoclonal antibody.

10. The method of claim 9, wherein the cancer is a cancer of the brain, breast, cervix, colon, head & neck, liver, kidney, lung, non-small cell lung, or stomach.

11. The method of claim 10, wherein the population of cells and the antibody are administered separately.

12. The method of claim 10, wherein the population of cells and the antibody are administered in the same formulation.

13. The method of claim 1, wherein the population of cells and the antibody are administered in separate formulations.

14. The method of claim 10, wherein the antibody is selected from the group consisting of alemtuzumab, bevacizumab, ibritumomab tiuxetan, ofatumumab, rituximab, and trastuzumab.

15. The method of claim 14, wherein the population of cells and the antibody are administered on the same day.

16. The method of claim 15, wherein between $1 \times 10^9$ and $1 \times 10^{10}$ cells are administered per dose.

17. The method of claim 16, wherein multiple doses of cells are administered to the subject.

18. The method of claim 1, wherein the cells are capable of secreting IL-2 at a concentration of 10 to 40 pg/hour per million cells.

* * * * *